(12) United States Patent
Jain et al.

(10) Patent No.: US 10,654,873 B2
(45) Date of Patent: May 19, 2020

(54) CYTOTOXIC AGENTS AND CONJUGATES THEREOF

(71) Applicant: POLYTHERICS LIMITED, Cambridge (GB)

(72) Inventors: Nareshkumar Jain, Ringoes, NJ (US); Sanjeevani Ghone, Plainsboro, NJ (US); Sean Smith, Hamilton, NJ (US); Ian Glassford, King of Prussia, PA (US); Sylvia J. Degrado, Newtown, PA (US); Fu-an Kang, Collegeville, PA (US); Senzhi Zhao, Bensalem, PA (US)

(73) Assignee: POLYTHERICS LIMITED, Cambridge (GB)

( * ) Notice: Subject to any disclaimer, the term of this patent is extended or adjusted under 35 U.S.C. 154(b) by 0 days.

(21) Appl. No.: 16/332,797

(22) PCT Filed: Sep. 15, 2017

(86) PCT No.: PCT/GB2017/052731
§ 371 (c)(1),
(2) Date: Mar. 13, 2019

(87) PCT Pub. No.: WO2018/051109
PCT Pub. Date: Mar. 22, 2018

(65) Prior Publication Data
US 2019/0202839 A1    Jul. 4, 2019

(30) Foreign Application Priority Data
Sep. 15, 2016    (GB) .................................. 1615725.7

(51) Int. Cl.
| C07D 498/18 | (2006.01) |
| A61K 31/537 | (2006.01) |
| A61P 35/00 | (2006.01) |
| A61K 47/68 | (2017.01) |
| A61K 47/69 | (2017.01) |

(52) U.S. Cl.
CPC .......... *C07D 498/18* (2013.01); *A61K 31/537* (2013.01); *A61K 47/6803* (2017.08); *A61K 47/6851* (2017.08); *A61K 47/6903* (2017.08); *A61P 35/00* (2018.01)

(58) Field of Classification Search
CPC ............................ C07D 498/18; A61K 31/537
See application file for complete search history.

(56) References Cited

U.S. PATENT DOCUMENTS

| 4,137,230 A | 1/1979 | Hashimoto et al. |
| 4,190,580 A | 2/1980 | Hashimoto et al. |
| 4,260,608 A | 4/1981 | Miyashita et al. |
| 5,208,020 A | 5/1993 | Chari et al. |
| 2012/0121615 A1 | 5/2012 | Flygare et al. |
| 2014/0179917 A1 | 6/2014 | Deng |

FOREIGN PATENT DOCUMENTS

| CN | 103483357 A | * | 1/2014 | .......... A61K 31/537 |
| EP | 0004466 A1 | | 10/1979 | |
| EP | 0425235 A2 | | 5/1991 | |
| EP | 2103618 A1 | | 9/2009 | |
| WO | 2004060965 A2 | | 7/2004 | |
| WO | 2004103272 A2 | | 12/2004 | |
| WO | 2005007197 A2 | | 1/2005 | |
| WO | 2010100430 A1 | | 9/2010 | |
| WO | 2010126551 A1 | | 11/2010 | |
| WO | 2011073391 A1 | | 6/2011 | |
| WO | 2012061590 A1 | | 5/2012 | |
| WO | 2013090590 A1 | | 6/2013 | |
| WO | 2014064424 A1 | | 5/2014 | |
| WO | 2016059377 A1 | | 4/2016 | |
| WO | 2016063006 A1 | | 4/2016 | |

OTHER PUBLICATIONS

International Search Report and Written Opinion issued in corresponding International Patent Application No. PCT/GB2017/052731 dated Oct. 23, 2017 (12 pages).
Cassady et al., "Recent Developments in the Maytansinoid Antitumor Agents," Chem. Pharm. Bull, 2004, 52(1), pp. 1-26.
Harmrolfs et al., "Preparation of new alkyne-modified ansamitocins by mutasynthesis," Beilstein Journal of Organic Chemistry, 2014, 10, pp. 535-543.
Kawai et al., "Chemical Modification of Ansamitocins. III. Synthesis and Biological Effects of 3-Acyl Esters of Maytansinol," Chem. Pharm. Bull, 1984, 32(9), pp. 3441-3451.
Taft et al., "Highly Active Ansamitocin Derivatives: Mutasynthesis Using an AHBA-Blocked Mutant," ChemBioChem, 2008, 9, pp. 1057-1060.
Taft et al., "Combined Muta- and Semisynthesis: A Powerful Synthetic Hybrid Approach to Access Target Specific Antitumor Agents Based on Ansamitocin P3," Chemistry, A European Journal, 2012, vol. 18, No. 3, pp. 880-886.

* cited by examiner

*Primary Examiner* — Karen Cheng
(74) *Attorney, Agent, or Firm* — Kilyk & Bowersox, P.L.L.C.

(57) ABSTRACT

Provided herein are novel maytansinoid compounds of general formula I. Also provided herein are conjugates comprising the compounds linked to a binding protein via a linker, and conjugating reagents comprising the compounds attached via a linker to at least one functional group capable of reacting with a binding protein. Also provided herein are pharmaceutical compositions comprising the compounds and conjugates, therapeutic methods and uses involving the compounds and conjugates, for example in cancer therapy, and novel synthetic processes.

32 Claims, 3 Drawing Sheets

CYTOTOXIC AGENTS AND CONJUGATES THEREOF

FIELD OF INVENTION

This invention relates to novel cytotoxic agents, novel conjugates, particularly antibody-drug conjugates, and intermediates for making the conjugates, including novel conjugating reagents. It also relates to a novel process for making cytotoxic agents.

BACKGROUND TO THE INVENTION

Much research has been devoted in recent years to the conjugation of therapeutic agents as payloads to peptides and proteins for a wide range of applications. The protein or peptide itself may have therapeutic properties, and/or it may be a binding protein. In addition, conjugation to polymers has been used to improve the properties of certain therapeutic agents. For example, water soluble, synthetic polymers, particularly polyalkylene glycols, are widely used to conjugate therapeutically active peptides or proteins. These therapeutic conjugates have been shown to alter pharmacokinetics favourably by prolonging circulation time and decreasing clearance rates, decreasing systemic toxicity, and in several cases, displaying increased clinical efficacy. The process of covalently conjugating polyethylene glycol, PEG, to proteins and other payloads is commonly known as "PEGylation".

Binding proteins (i.e. proteins or peptides capable of binding to a binding partner on a target), particularly antibodies or antibody fragments, are frequently used in conjugates. For example, they may be conjugated to cytotoxic agents and chemotherapy drugs to produce antibody-drug conjugates (ADCs), allowing targeted delivery of such agents to specific tissues or structures, for example particular cell types or growth factors, minimising the impact on normal, healthy tissue and significantly reducing the side effects associated with chemotherapy treatments. Such conjugates have extensive potential therapeutic applications in several disease areas, particularly in cancer.

Kupchan et al., J. Am. Chem. Soc., 94, 1354 (1972) first isolated Maytansine from the bark of the African shrub *Maytenus ovatus*, where it was noted for its anti-leukemic properties. Maytansinoids, such as maytansinol and C-3 esters of maytansinol were found to be made by microbes (U.S. Pat. No. 4,151,042), mosses (Sakai et al, J. Nat. Prod., 51(5), 845-850, 1988), and could also be generated by synthetic routes (Kupchan et al., J. Med. Chem., 21, 31-37, 1978, Higashide et al., Nature 270, 721-722, 1977). Maytansine and maytansinol have the structures:

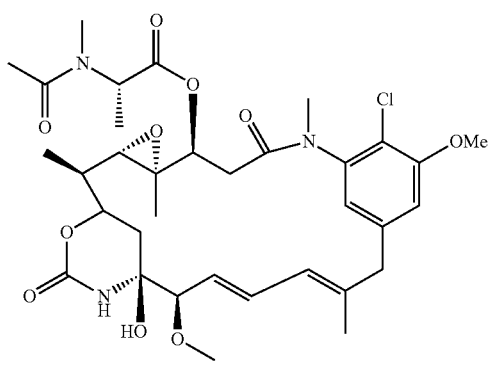

Maytansine

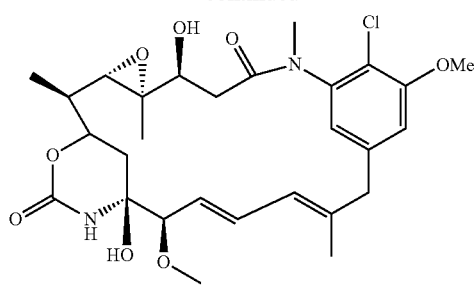

Maytansinol

U.S. Pat. No. 4,190,580 described a method of synthesis of maytansinoids, while U.S. Pat. No. 4,260,608 identified a number of maytansine derivative compounds with potent anti-microbial and anti tumour activities as a result of their anti-mitotic effects upon cells. U.S. Pat. No. 4,260,608 disclosed maytansine derivatives with an optionally substituted alkyl group at the R3 position. Since then numerous structure-activity relationship studies have been performed to determine other potent structures of maytansinoids. Kawai et al., Chem. Pharm. Bull. 32(9), 3441-3451 (1984) published a number of structures that were modified at the C3 position of Maytansinol, which displayed potent anti-tumour effects in vivo. EP 0 004 466, U.S. Pat. No. 4,137,230 and WO 2012/061590 all describe novel maytansinoids. Various modifications of maytansinoids are described in US 2009/258870, Taft et al, Chem. Eur. J. 2012, 18, 880-886, and Harmrolfs et al, Beilstein J. Org. Chem. 2014, 10, 535-543.

Well-known maytansinoids include those known as DM1 and DM4 as described within U.S. Pat. No. 5,208,020 and WO2004/103272. These have the structures:

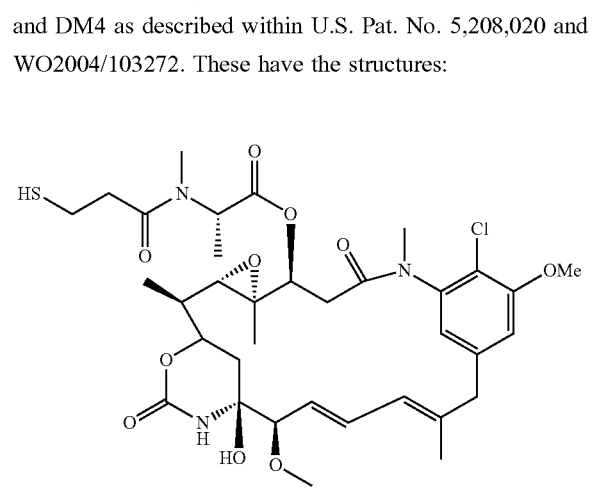

DM1 or Mertansine

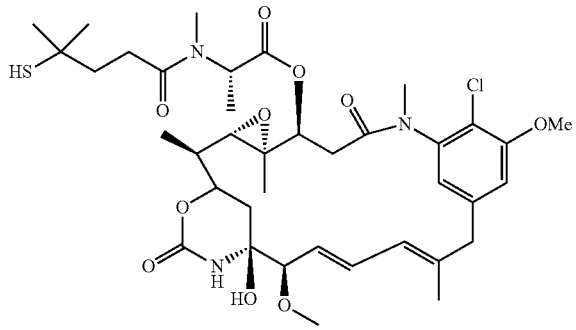

Ansamitocins are a sub-group of maytansinoids, the synthesis of which is described by Taft et al, ChemBioChem 2008, 9, 1057-1060. A well-known ansamitocin is AP-3, which has the structure:

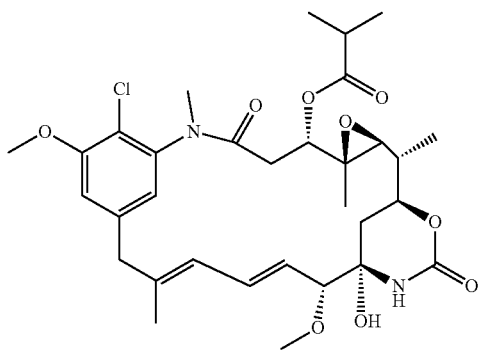 [SMILES: COc1cc2cc(c1Cl)N(C)C(=O)C[C@H](OC(=O)C(C)C)[C@]1(C)O[C@H]1[C@H](C)[C@@H]1C[C@@](O)(NC(=O)O1)[C@H](OC)/C=C/C=C(\C)C2]

Maytansinoids and maytansinoid esters were subsequently used as a cytotoxic payload within an ADC context within EP 0 425 235 and have been used extensively since, see for example Liu et al, Proc. Natl. Acad. Sci. USA, 93, 8618-8623 (1996); and Kieda et al, Clin. Cancer Res., 15(12), 2009. Widdison et al, J. Med. Chem. 49, 4392-4408 (2006) described the thiol-linked DM1 and DM4 maytansinoid payloads. These payloads were conjugated via a two-step process in which first a heterobifunctional, thiol-containing linker was reacted with lysine residues within the antibody, followed by conjugation of the thiol-containing payloads to the linker by disulfide exchange. An alternative means of producing ADCs by this two-step process is by use of a succinimidyl trans-4-(maleimidylmethyl)cyclohexane-1-carboxylate (SMCC) heterobifunctional linker, which has a succinimide group at one end to react with lysine residues within the antibody and a maleimide group at the other end to react with the thiol group of the maytansinoid. The commercially-available pharmaceutical Kadcyla® is an example of an ADC produced using an SMCC linker with a DM1 maytansinoid payload. Kadcyla® is currently one of the leading ADCs in the clinic and is used for the treatment of HER2-positive breast cancer.

WO 2014/064424 describes ADCs based on maytansines using a different specific technology to bind the drug to the antibody. Exemplified are conjugates derived from the reagent AHX-DM1 available commercially from Levena (Concortis), and having the structure:

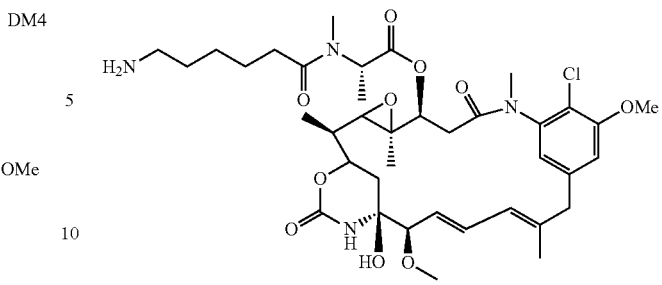

There is still a need for novel, potent cytotoxic molecules that may be used within an ADC context. These payloads need to be conjugated efficiently with an antibody using a conjugation technology which allows more stable ADCs to be generated. There is also a need for ADCs which show greater efficacy or potency in relevant cell or animal models of cancers, or alternatively, show a similar level of efficacy/potency but a reduced amount of non-specific toxicity within the cell or test subject.

We have now found that certain novel maytansinoid compounds possess improved cytotoxic activity, and are particularly suited for inclusion in conjugates with binding proteins. The maytansinoids further have improved stability compared with comparator compounds. We have also found a novel method of synthesis which enables efficient preparation of these novel compounds as well as a novel and improved method of synthesis of other maytansinoids.

SUMMARY OF THE INVENTION

The invention provides a compound of the general formula (I) or a salt thereof:

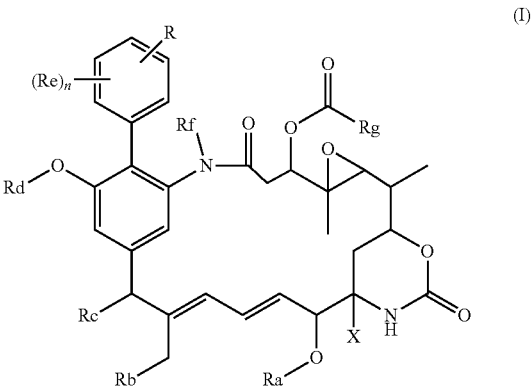

in which R represents a group —Y—OH, —Y—O—$R^x$, —Y—SH, —Y—S—$R^x$, —Y—S(O)$_2$NH—$R^x$, —Y—NHS(O)$_2$—$R^x$, —Y—C(O)H, —Y—CO$_2$H, —Y—C(O)—$R^x$, —Y—C(O)NH—$R^x$, —Y—NHC(O)—$R^x$, —Y—NH$R^y$, —Y—N$R^x R^y$, —Y—N$R^y$—NH$^z$, —Y—C$R^y$=NOH, —Y—C(NH$_2$)=NOH, —Y—C(O)NH$_2$, —Y—C(O)NH—NH$_2$, or —Y—S(O)$_2$NH$_2$, in which either Y is not present or Y represents a C$_{1-6}$alkylene, C$_{2-6}$alkenylene, C$_{2-6}$alkynylene or C$_{1-6}$alkyleneoxy group which may be interrupted by an oxygen atom and/or which may optionally be substituted by —OH or —OC$_{1-4}$alkyl, or Y represents a phenylene or C$_{5-10}$heteroarylene group; $R^x$ represents a C$_{1-6}$alkyl, C$_{2-6}$alkenyl, C$_{2-6}$alkynyl, phenyl, C$_{5-10}$heteroaryl or benzyl group which is substituted by —OH, —SH, —NH$R^y$, or —CO$_2$H; each of R$^y$ and R$^z$ independently represents a hydrogen atom, a C$_{1-4}$alkyl group, phenyl, C$_{5-10}$heteroaryl or a benzyl group; X represents OH, OC$_{1-4}$alkyl, SH, S$_{1-4}$alkyl, or CN; Ra represents a hydrogen atom or a C$_{1-4}$alkyl group; Rb represents hydrogen, OH, C$_{1-4}$alkoxy or C$_{1-4}$alkylC(O)O—; Rc represents hydrogen, OH, C$_{1-4}$alkoxy or C$_{1-4}$alkylC(O)O—; Rd represents a hydrogen atom or a C$_{1-4}$alkyl group; each Re independently represents a halogen atom, an optionally substituted C$_{1-6}$alkyl, C$_{2-6}$alkenyl, C$_{2-6}$alkynyl or C$_{1-6}$alkoxy group each of which may be optionally interrupted by an oxygen atom, an optionally substituted phenyl or C$_{5-10}$heteroaryl group, —OH, —CO$_2$R$^v$, —C(O)NR$^v$R$^w$, —NR$^v$C(O)R$^w$, NR$^v$R$^w$, —SR$^v$, —S(O)—R$^v$, S(O)$_2$—R$^v$, —S(O)$_2$NR$^v$R$^w$, a —CN group, or a —NO$_2$ group; R$^v$ and R$^w$ are each independently selected from the group consisting of hydrogen, phenyl, benzyl, and an optionally substituted C$_{1-6}$alkyl, C$_{2-6}$alkenyl or C$_{2-6}$alkynyl group each of which may be optionally interrupted by an oxygen atom; and n is 0, 1, 2, 3 or 4; Rf represents a hydrogen atom or a C$_{1-4}$alkyl group; and Rg represents a hydrogen atom or an optionally substituted alkyl, cycloalkyl, alkenyl, alkynyl, aryl, or heteroaryl group.

The invention also provides a compound of the general formula (I') or a salt thereof:

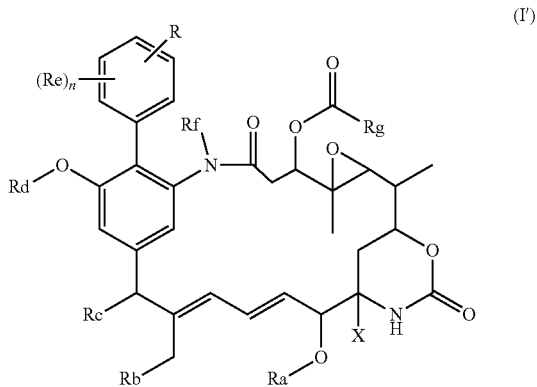

(I')

in which R represents a group —Y—OH, —Y—O—R$^x$, —Y—SH, —Y—S—R$^x$, —Y—CO$_2$H, —Y—CO—R$^x$, —Y—NHR$^y$, —Y—NR$^y$—NHR$^z$, or —Y—CR$^y$=NOH, in which either Y is not present or Y represents a C$_{1-6}$alkylene or C$_{1-6}$alkyleneoxy group either of which may be interrupted by an oxygen atom, R$^x$ represents a C$_{1-4}$alkyl group substituted by —OH, —SH, —NHR$^y$, or —CO$_2$H, and each of R$^y$ and R$^z$ independently represents a hydrogen atom or a C$_{1-4}$alkyl group; X represents OH, OC$_{1-4}$alkyl, SH, S$_{1-4}$alkyl, or CN; Ra represents a hydrogen atom or a C$_{1-4}$alkyl group; Rb represents hydrogen, OH, C$_{1-4}$alkoxy or C$_{1-4}$alkylC(O)O—; Rc represents hydrogen, OH, C$_{1-4}$alkoxy or C$_{1-4}$alkylC(O)O—; Rd represents a hydrogen atom or a C$_{1-4}$alkyl group; each Re independently represents a halogen atom, a CF$_3$ group, or a C$_{1-4}$alkyl or C$_{1-4}$alkoxy group, and n is 0, 1, 2, 3 or 4; Rf represents a hydrogen atom or a C$_{1-4}$alkyl group; and Rg represents a hydrogen atom or an optionally substituted alkyl, cycloalkyl, alkenyl, alkynyl, aryl, or heteroaryl group.

The invention also provides a conjugate comprising a compound of the general formula (I) or (I') or a salt thereof linked to a binding protein via a linker, said linker being connected to said compound via the group R of the general formula (I) or (I').

The invention further provides a conjugating reagent which comprises a compound of the general formula (I) or (I') or a salt thereof attached via a linker to at least one functional group capable of reacting with a binding protein, said linker being connected to said compound via the group R of the general formula (I) or (I').

The invention further provides a pharmaceutical composition which comprises a compound or a conjugate according to the invention, together with a pharmaceutically acceptable carrier, and optionally together with an additional therapeutic agent. Also provided is a method of treating a patient in need of treatment for a proliferative, autoimmune, or infectious disease or disorder which comprises administering a pharmaceutically-effective amount of a compound, conjugate or composition according to the invention to the patient. Also provided is a compound, conjugate or composition according to the invention for use in therapy, particularly for use in the treatment of a proliferative, autoimmune, or infectious disease or disorder. Further, a compound or conjugate according to the invention may be used in the manufacture of a medicament for use in the treatment of a proliferative, autoimmune or infectious disease or disorder.

The invention also provides a process for the preparation of the compounds according to the invention, and novel intermediates useful for preparing the compounds according to the invention.

DETAILED DESCRIPTION OF THE INVENTION

The Compounds

The compounds of the invention are of the general formula (I). The compounds of the invention are a new class of biphenyl-containing compounds having unexpected biological activity. Compounds of the invention also find utility in the production of new antibody-drug conjugates and conjugating reagents.

In some embodiments the compounds are of the formula (I').

In the compounds of the invention, preferably any group R$^y$ or R$^z$ present in R is a methyl group or, especially, a hydrogen atom. In one preferred embodiment, Y is not present. If Y is present, it is preferably a C$_{1-4}$alkylene or C$_{1-4}$alkyleneoxy group, which may be interrupted by an oxygen atom, as in, for example, —CH$_2$—O—CH$_2$—. An alkylene group may for example be a methylene, ethylene or n-propylene group, while an alkyleneoxy group may for example be a methyleneoxy, ethyleneoxy or n-propyleneoxy group. In some embodiments R is —Y—OH, —Y—SH, —Y—S(O)$_2$NH—R$^x$, —Y—NHS(O)$_2$—R$^x$, —Y—CO$_2$H, —Y—C(O)NH—R$^x$, —Y—NHC(O)—R$^x$, —Y—NHR$^y$ or —Y—S(O)$_2$NH$_2$, wherein Y is not present or Y represents a C$_{1-6}$alkylene group, and wherein R$^x$ represents a C$_{1-6}$ alkyl group which is substituted by —OH, —SH, —NH$_2$ or CO$_2$H. In some preferred embodiments R is Y—NHC(O)—R$^x$, more preferably R is Y—NHC(O)—R$^x$ in which Y is absent, still more preferably R is Y—NHC(O)—R$^x$ in which Y is absent and R$^x$ represents C$_{1-6}$alkyl substituted by —SH. In some preferred embodiments, R is —OH, —NH$_2$, —SH, —CONH$_2$, —SO$_2$NH$_2$, —CO$_2$H, CH$_2$OH, or —NHC(O)—C$_{1-6}$alkylene-SH, particularly —NH$_2$ or —NH—C(O)—C$_{1-6}$alkylene-SH, and especially —NH—C(O)—C$_{1-6}$alkylene-SH. When R is —NH—C(O)—C$_{1-6}$alkyl wherein said alkyl is substituted by —SH (i.e. —NH(C(O)—C$_{1-6}$ alkylene-SH), the C$_{1-6}$alkyl moiety may be straight chain or branched and, for example, R may include the following:

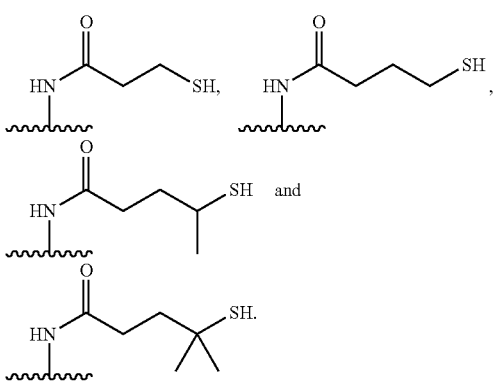

In some embodiments, R is an —OH, —NH$_2$, —CONH$_2$ or —CO$_2$H group, or a C$_{1-4}$alkylene group, especially a methylene, ethylene or n-propylene group, substituted by an —OH, —NH$_2$, —CONH$_2$ or —CO$_2$H group. The R group may be at any position of the phenyl ring. The group R is preferably in the 3- or 4-position of the phenyl ring (i.e. relative to the position of the phenyl ring forming a bond to the phenyl ring which forms part of the maytansinoid core structure)

Where present, each Re independently represents a halogen atom, an optionally substituted C$_{1-6}$alkyl, C$_{2-6}$alkenyl, C$_{2-6}$alkynyl or C$_{1-6}$alkoxy group each of which may be optionally interrupted by an oxygen atom, an optionally substituted phenyl or C$_{5-10}$heteroaryl group, —OH, —CO$_2$R$^v$, —C(O)NR'R$^w$, —NR'C(O)R$^w$, NR'R$^w$, —S(O)—R$^v$, S(O)$_2$—R$^v$, —S(O)$_2$NR'R$^w$, a —CN group, or a —NO$_2$ group. In some embodiments, Re is either absent or where present each Re independently represents a halogen atom, a CF$_3$ group, a C$_{1-4}$alkyl group, a C$_{1-4}$alkoxy group, a —CN group, or a —NO$_2$ group. In some embodiments, any Re group present is independently selected from the group consisting of a halogen atom, a methoxy group, a —CN group or a —NO$_2$ group. In some preferred embodiments, any Re group present is selected from the group consisting of chlorine, fluorine, a methoxy group, a —CN group and a —NO$_2$ group. In some preferred embodiments, any Re group present is preferably a halogen atom, for example a chlorine, bromine or fluorine atom, or a methyl or methoxy group. Preferably n is 0, 1 or 2, especially 0 or 1, especially 0. Where present, the or each Re group may be at any position of the phenyl group other than the position at which the phenyl ring is substituted by the R group.

Preferably X represents OH. Preferably Ra represents C$_{1-4}$alkyl, especially methyl. Preferably Rb represents hydrogen. Preferably Rc represents hydrogen or methoxy, more preferably hydrogen. Preferably Rd represents C$_{1-4}$alkyl, especially methyl. Preferably Re represents chlorine or hydrogen, especially chlorine. Preferably Rf represents C$_{1-4}$alkyl, especially methyl.

The nature of the substituent Rg is not believed to be crucial to the present invention, a very wide range of substituents at this position in the maytansine core having been reported in the literature. Any alkyl, alkenyl or alkynyl group preferably has up to 10, for example up to 6, carbon atoms. A cycloalkyl group preferably has 5, 6 or 7 ring carbon atoms, and may for example be substituted by one or more C$_{1-4}$ alkyl groups. An aryl group is preferably a phenyl group. A heteroaryl group may for example have 5, 6 or 7 ring atoms including at least one O, S and/or N atom. It may for example be a thiophene, pyrrole, pyrrolidone, oxazole, thiazole, imidazole, pyrazole, pyrazoline, isoxazole, triazole, pyran, pyridine, piperidine, dioxane, morpholine, pyridazine, pyrimidine, pyrazine, or piperazine group. Optional substituents which may be present on an aryl or heteroaryl group Rg include halogen atoms and alkyl, haloalkyl, hydroxy, amino, alkylamino, dialkylamino and alkoxy groups, in which any alkyl moiety has from 1 to 4 carbon atoms. An alkyl group Rg may for example be substituted by one or more halogen atoms and/or hydroxy, alkoxy, amino, alkylamino, or dialkylamino groups, in which any alkyl moiety has from 1 to 4 carbon atoms. An alkyl group Rg may also be substituted by one or more amino acids, for example N-methylalanine or N-methylcysteine. In some embodiments where Rg is a substituted alkyl group, the group —C(O)—R$_g$ may be amino acid-derived. For example, an alkyl group Rg may be substituted by a group N(R$^i$)(R$^{ii}$), in which R$^i$ represents hydrogen or a C$_{1-4}$alkyl group, and in which R$^{ii}$ represents a C$_{1-4}$alkyl group, a —C(O)—C$_{1-6}$alkyl group, a —C(O)—C$_{2-6}$alkenyl group, or a —C(O)—C$_{3-6}$cycloalkyl group wherein said C$_{3-6}$cycloalkyl group may be unsubstituted or substituted by up to 2 methyl groups. In some preferred embodiments Rg represents C$_{1-4}$alkyl which is unsubstituted or substituted by N(R$^i$)(R$^{ii}$); R$^i$ represents a C$_{1-4}$alkyl group; and R$^{ii}$ represents a —C(O)—C$_{1-6}$alkyl group. Examples of such Rg groups include

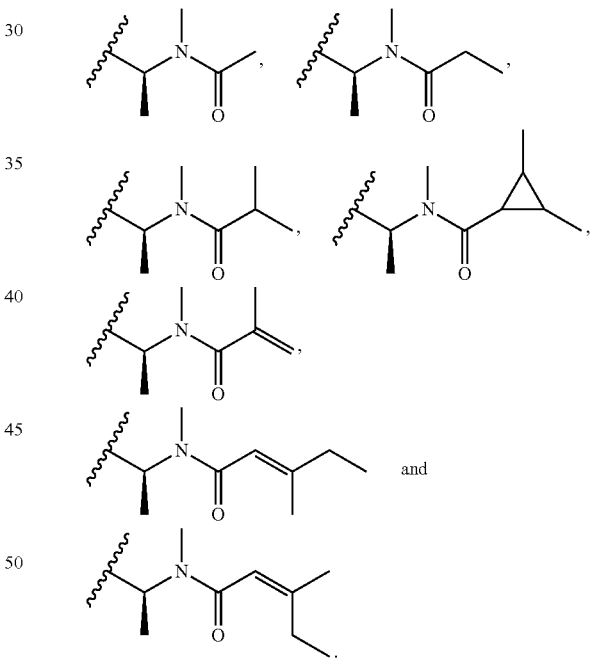

In some embodiments where Rg is a substituted alkyl group, in addition to being substituted by a group N(R$^i$)(R$^{ii}$) as discussed above, the alkyl group may optionally be substituted by a substituent selected from the group consisting of —OH, —SH, —SMe, a C$_{6-10}$ aromatic carbocycle which is optionally substituted by hydroxyl, and a C$_{5-10}$ aromatic heterocycle. As discussed above, the group —C(O)—R$_g$ may be amino acid-derived. For example, the group —C(O)—Rg may comprise an amino acid residue, e.g. such as L-alanine or L-methionine.

In some preferred embodiments, Rg represents a substituted or, especially, unsubstituted, C$_{1-6}$alkyl group, for example methyl, ethyl, propyl, isopropyl, butyl, isobutyl, pentyl, hexyl, or an optionally substituted phenyl group. Most preferably Rg represents $C_{1-4}$alkyl, especially isopropyl.

In some preferred embodiments, Ra represents $C_{1-4}$alkyl; Rb represents hydrogen; Rc represents hydrogen or methoxy; Rd represents $C_{1-4}$alkyl; Re is absent or where present represents fluorine, chlorine, methoxy, —CN, or —$NO_2$; n=0 or 1; Rf represents $C_{1-4}$alkyl; and Rg represents $C_{1-4}$alkyl.

In some preferred embodiments, Ra represents $C_{1-4}$alkyl; Rb represents hydrogen; Rc represents hydrogen or methoxy; Rd represents $C_{1-4}$alkyl; Re is absent or where present represents chlorine; Rf represents $C_{1-4}$alkyl; and Rg represents $C_{1-4}$alkyl.

Preferably the compound is a compound of formula (I'), or a salt thereof:

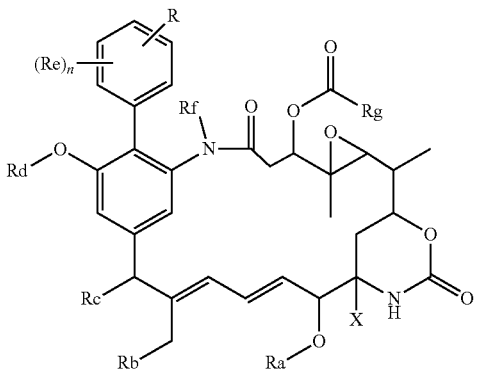
(I')

in which R represents a group —Y—OH, —Y—O—$R^x$, —Y—SH, —Y—S—$R^x$, —Y—$CO_2H$, —Y—C(O)—$R^x$, —Y—$NHR^y$, —Y—$NR^y$—$NHR^z$, or —Y—$CR^y$=NOH, in which either Y is not present or Y represents a $C_{1-6}$alkylene or $C_{1-6}$alkyleneoxy group either of which may be interrupted by an oxygen atom, $R^x$ represents a $C_{1-4}$alkyl group substituted by —OH, —SH, —$NHR^y$, or —$CO_2H$, and each of $R^y$ and $R^z$ independently represents a hydrogen atom or a $C_{1-4}$alkyl group; X represents OH, $OC_{1-4}$alkyl, SH, $S_{1-4}$alkyl, or CN; Ra represents a hydrogen atom or a $C_{1-4}$alkyl group; Rb represents hydrogen, OH, $C_{1-4}$alkoxy or $C_{1-4}$alkylC(O)O—; Rc represents hydrogen, OH, $C_{1-4}$alkoxy or $C_{1-4}$alkylC(O)O—; Rd represents a hydrogen atom or a $C_{1-4}$alkyl group; each Re independently represents a halogen atom, a $CF_3$ group, or a $C_{1-4}$alkyl or $C_{1-4}$alkoxy group, and n is 0, 1, 2, 3 or 4; Rf represents a hydrogen atom or a $C_{1-4}$alkyl group; and Rg represents a hydrogen atom or an optionally substituted alkyl, cycloalkyl, alkenyl, alkynyl, aryl, or heteroaryl group.

Preferably, the compound of the invention is a compound of the general formula (Ia) or a salt thereof:

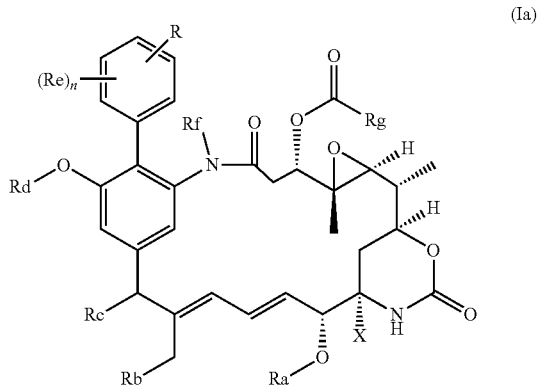
(Ia)

in which R, X, n and Ra-Rg have the meanings and preferred meanings set out above, e.g. for the compound of formula (I) or formula (I'). The compound of formula (Ia) may also be represented as follows:

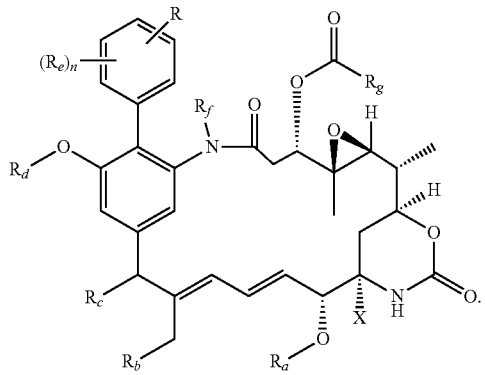
(Ia)

More preferably, the compound of the invention is a compound of the general formula (Ib) or a salt thereof:

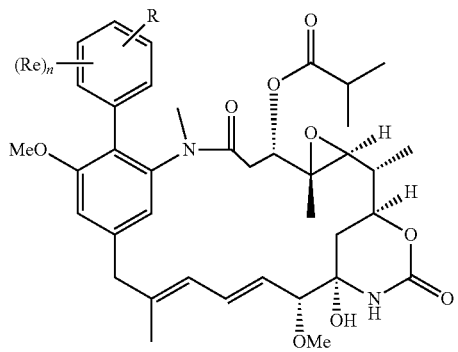
(Ib)

in which R, Re and n have the meanings and preferred meanings set out above, e.g. for the compound of formula (I) or formula (I').

In some embodiments the compound is a compound of formula (Ib) in which n is 0 or 1; Re where present is chlorine, fluorine, methoxy, —CN or $NO_2$; and R is —$NH_2$ or —NH—C(O)—$C_{1-6}$alkylene-SH; or a salt thereof.

In some embodiments the compound is a compound of formula (Ic)

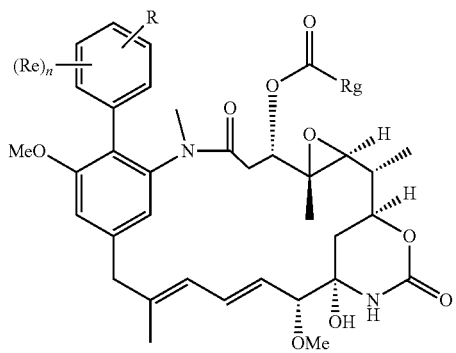

in which Rg is

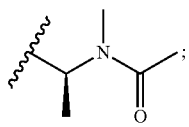 [SMILES: *[C@H](C)N(C)C(C)=O]

n is 0 or 1; Re where present is chlorine, fluorine, methoxy, —CN or —NO$_2$; and R is —NH$_2$ or —NH—C(O)—C$_{1-6}$alkylene-SH; or a salt thereof.

Compounds of the formula (I) (and (I'), (Ia), (Ib) and (Ic)) may form salts. Suitable salts according to the invention include those formed with organic or inorganic acids. In particular, suitable salts formed with acids include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as (C$_1$-C$_4$)-alkyl- or aryl-sulfonic acids which are unsubstituted or substituted, for example by halogen.

Pharmaceutically acceptable acid addition salts include those formed from hydrochloric, hydrobromic, sulphuric, nitric, citric, tartaric, acetic, phosphoric, lactic, pyruvic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Compounds of the formula (I) (and (I'), (Ia), (Ib) and (Ic)) and salts thereof may also exist in the form of solvates, for example hydrates.

The compounds of the invention contain chiral (asymmetric centres). Individual stereoisomers (enantiomers and diastereoisomers) are within the scope of the present invention. Compounds of the invention may also exist as atropisomers, which are stereoisomers that arise due to hindered rotation about a single bond (for example a biaryl bond). In some cases the barrier to interconversion between atropisomers may be sufficiently high such that individual atropisomers are stable and may be isolable. Accordingly, individual atropisomers are also within the scope of the present invention. In some circumstances, compounds may exist in tautomeric forms, and such tautomeric forms of the compounds are also encompassed by the present invention.

The payloads of the present invention may be formed into conjugates, and as such, they may be regarded as intermediates useful for the preparation of conjugates. Their structure allows connection to a linker at the C-19 position (see Higashide et al 1977, supra, for nomenclature). Maytansinoid payloads which are connected to linkers via an ester bond to the C-3 position are known to be subject to cleavage/hydrolysis by esterases or beta elimination. Esterases are known to reside within the blood and both of these hydrolysis mechanisms may result in premature release of the maytansinoid payload before it has entered the cell, which can cause non-specific toxicities and/or reduced potency of the anti-tumour drug. It is however understood by the present inventors that the presence of a C-3 ester substituent in a maytansinoid is associated with improved potency. Although when conjugation is via the C-19 position beta elimination and/or hydrolysis by esterases are still possible, the payload and therefore the ADC will still retain activity and unlike payloads conjugated at C-3, will not undergo premature release following these reactions. Furthermore, the present inventors have carried out comparative in vitro serum stability experiments which surprisingly indicate that a comparator compound which is suitable for conjugation via a C-3 ester substituent, is less stable than a compound which is suitable for conjugation via the C-19 position but which also still contains a C-3 ester substituent. Thus, the compounds of the invention, as well as the conjugates incorporating those compounds, are considered to possess good stability properties.

Process Aspects of the Invention

It is a key feature of the compounds of the present invention that the phenyl group present in the maytansine core structure carries a further phenyl group substituted by a group R, and this group R can be used to conjugate the compound to a binding protein. The core structure of maytansine contains a phenyl group carrying a chlorine atom. The inventors have discovered a novel method which displaces this chlorine atom to produce the phenyl-containing compounds of the invention. Accordingly, the present invention also provides a process for the preparation of a compound of the invention which comprises reacting a compound of the general formula:

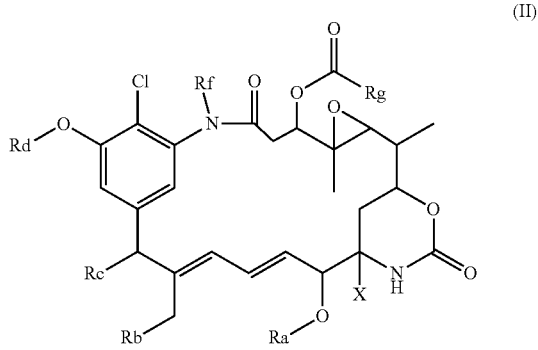

in which X, Ra-Rd, Rf and Rg have the meanings and preferred meanings given above for the compound of formula (I), (I'), (Ia), (Ib) or (Ic), with an aryl-organometallic reagent in which the aryl moiety is a phenyl group which is substituted by (Re)$_n$ and R or a protected version of R, and in which R and (Re)$_n$ have the meanings given for the general formula (I), (I'), (Ia), (Ib) or (Ic), the reaction being carried out in the presence of a transition metal catalyst.

The aryl-organometallic reagent may for example be an aryl zinc, aryl tin, aryl magnesium, or aryl silicon reagent. More preferably, the aryl-organometallic reagent is an aryl boron reagent; especially an aryl boronic acid of the general formula

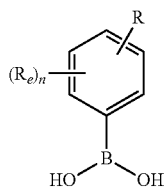

(III)

in which R and (Re)$_n$ have the meanings given for the general formula (I), (I'), (Ia), (Ib) or (Ic), and in which R may be present in protected form.

The transition metal catalyst may for example be derived from copper, nickel or, especially, palladium, and the metal is generally in the oxidation state I or II. The metal is present together with a bidentate or, especially, monodentate ligand. This ligand may for example be based on nitrogen or, especially, phosphorus. An especially preferred catalyst is (2-dicyclohexylphosphino-2',6'-dimethoxybiphenyl)[(2-(2'-amino-1,1'-biphenyl)palladium(II) methanesulfonate, commercially available as Sphos Pd G3 from Sigma Aldrich.

The reaction will generally be carried out in the presence of a solvent, for example an ether solvent such as THF, 2-methyl-THF, 1,4-dioxane, methyl tert-butyl ether or dimethoxyethane, a hydrocarbon such as toluene, or an alcohol such as n-butanol. The use of THF is preferred. Basic conditions are usually suitable. The reaction is generally carried out at room temperature or elevated temperature. The reaction temperature may for example be from 20 to 120° C., for example from 30 to 100° C., especially from 40-60° C.

Preferably the compound of the formula (II) has the formula:

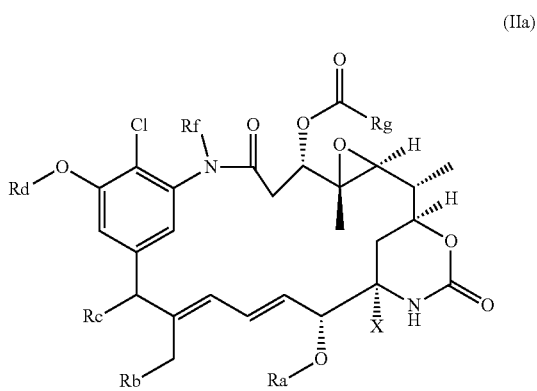

(IIa)

in which Ra, Rb, Rc, Rd, Rf, Rg and X are as defined above, e.g. as for the compound of formula (I), (I'), (Ia), (Ib) or (Ic), or

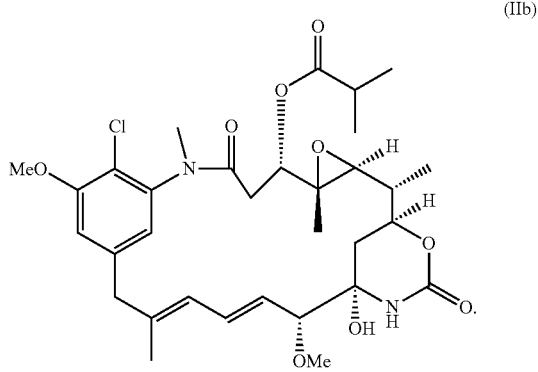 [SMILES: COc1cc2cc(c1Cl)N(C)C(=O)C[C@H](OC(=O)C(C)C)[C@]1(C)O[C@H]1[C@H](C)[C@@H]1C[C@@](O)(NC(=O)O1)[C@H](OC)/C=C/C=C(\C)C2]

(IIb)

It will be understood that in the aryl-organometallic reagents, especially reagents of the formula (III) (and (IIIc), (IIIb), (IIIc) and (IIId), discussed below), the group R may be present in protected form. Suitable groups for protecting a carboxy group include methyl, ethyl, t-butyl, benzyl, p-methoxybenzyl, 9-fluorenylmethyl, trimethylsilyl, t-butyldimethylsilyl, and diphenylmethyl. Suitable groups for protecting an amino group include t-butoxycarbonyl (BOC), trityl, benzyloxycarbonyl, 9-fluorenylmethoxycarbonyl, formyl, trimethylsilyl, and t-butyldimethylsilyl (TBDMS), phthalimide and succinimides, and analogous groups may be used to protect a hydrazine or hydroxylamine group. Suitable groups for protecting a hydroxy group include silyl groups including triC$_{1-6}$alkylsilyl groups, such as trimethylsilyl, triethylsilyl, t-butyldiphenylsilyl and t-butyldimethylsilyl; acyl groups including C$_{1-6}$alkanoyl groups, such as formyl, acetyl, and pivaloyl, and aromatic acyl groups such as benzoyl; arylmethyl groups such as benzyl, p-methoxybenzyl, 9-fluorenylmethyl, and diphenylmethyl; acetal groups such as tetrahydropyran (THP); ethers such as allyl ether and t-Bu ether; methoxymethyl ether (MOM) and 2-methoxyethoxymethyl ether (MEM). Numerous examples of suitable protecting groups may be found in, for example, "Greene's Protective Groups in Organic Synthesis", Wiley-Blackwell, 2014.

Where the aryl-organometallic reagent contains a group R in protected form, the immediate product of the process of the invention will be a compound of the formula (I), (I'), (Ia), (Ib) or (Ic), or a salt thereof, in which the group R is also present in that protected form, thus:

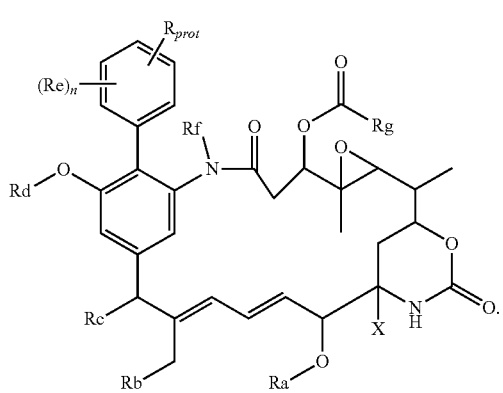

These protected compounds are converted into the corresponding compound of the general formula (I), (I'), (Ia), (Ib) or (Ic) or salt thereof by removal of the protecting group, and as such, the protected compounds are useful as intermediates for the preparation of the compounds of the general formula (I), (I'), (Ia), (Ib) or (Ic) or salt thereof. These protected compounds, which are themselves expected to have biological activity, are novel, and form a further aspect of the present invention. Especially preferred are compounds in which the protecting group is one of those mentioned above.

In some preferred embodiments, the process comprises reacting a compound of formula (II) with an aryl-boron reagent in which the aryl moiety is a phenyl group substituted by (Re)$_n$ and by R or a protected version of R, in which R and (Re)$_n$ have the meanings given for the general formula (I), (I'), (Ia), (Ib) or (Ic), in the presence of a palladium catalyst. Palladium-catalysed reactions between aryl halides and aryl boron reagents are often referred to in the art as Suzuki reactions, Suzuki couplings, Suzuki-Miyaura reactions, or Suzuki-Miyaura couplings. Where the process comprises a Suzuki reaction, in some embodiments, the aryl boron reagent is an aryl-boronic acid, an aryl-boronate ester, or an aryl trifluoroborate salt. Preferably the aryl boron reagent is either an aryl-boronic acid, e.g. of the formula (III)

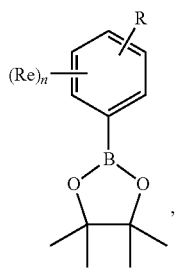

or an aryl-boronate ester, e.g. a pinacol ester of the formula (IIIa), a 1,3-propanediol ester of formula (IIIb), a neopentylglycol ester of formula (IIIc), or an N-methyliminodiacetic ester of formula (IIId):

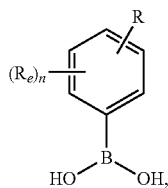

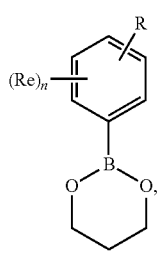

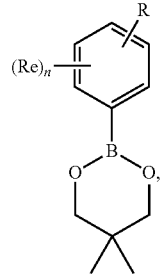

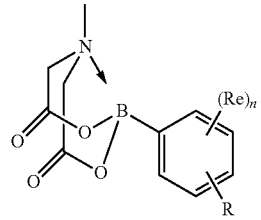

in which R and (Re)$_n$ have the meanings given for the general formula (I), (I'), (Ia), (Ib) or (Ic), and in which R may be present in protected form; especially an aryl boronic acid of the general formula

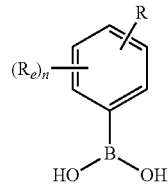

in which R and (Re)$_n$ have the meanings given for the general formula (I), (I'), (Ia), (Ib) or (Ic), and in which R may be present in protected form. Where R and/or Re groups present in the aryl boron reagents may form salts (e.g. in the case of an aryl boron reagent containing an R group which is —NH$_2$), suitable salt forms of the reagents may be used (such as the hydrochloride salt in the case where R is —NH$_2$).

Where the process comprises carrying out a Suzuki reaction (i.e. a coupling involving an aryl boron reagent and the use of a palladium catalyst), the reaction is typically carried out in the presence of a suitable base, such as an inorganic potassium base, e.g. potassium phosphate, potassium carbonate, potassium hydroxide or potassium fluoride. Preferably, the reaction is carried out in the presence of potassium phosphate.

Suitable palladium catalysts for Suzuki reactions involving a compound of formula (III) and the appropriate aryl boron reagent include those based on sterically hindered phosphine ligands containing cyclohexyl groups, such as (2-dicyclohexylphosphino-2',6'-dimethoxybiphenyl)[(2-(2'-amino-1,1'-biphenyl)palladium(II) methanesulfonate, commercially available as SPhos Pd G3 from Sigma Aldrich, as mentioned above, and (2-Dicyclohexyl phosphino-2',4',6'-triisopropyl-1,1'-biphenyl)[2-(2'-amino-1,1'-biphenyl)]palladium(II) methanesulfonate, commercially available as XPhos Pd G3 from Sigma Aldrich, or a mixture of the two. Other examples include the catalysts sold by Sigma Aldrich under the commercial names SPhos Pd G4 and XPhos Pd G4. The structures of these catalysts are provided below:

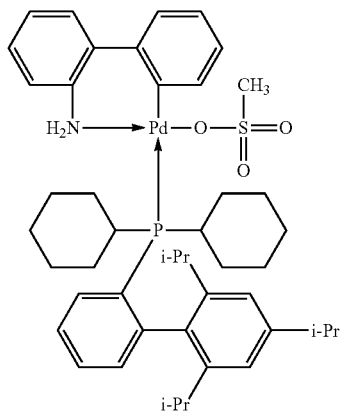
XPhos Pd G3

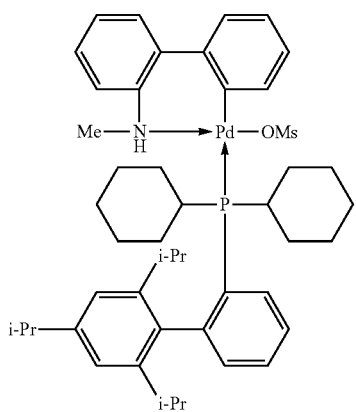
XPhos Pd G4

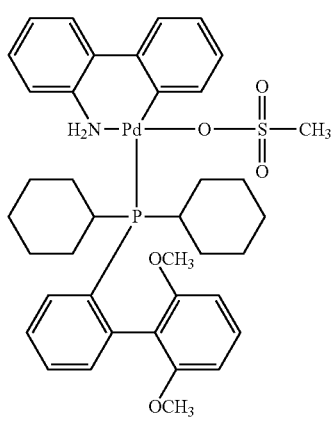
SPhos Pd G3

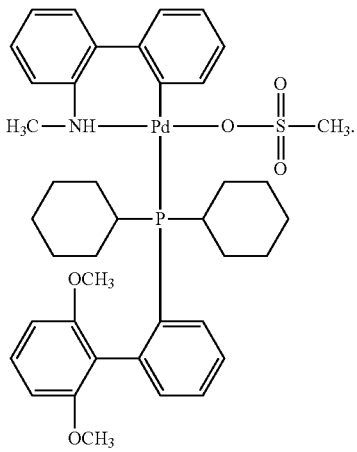
SPhos Pd G4

A further example of a suitable catalyst is palladium(II) acetate in combination with the XPhos ligand (2-dicyclohexylphosphino-2',4',6'-triisopropylbiphenyl), which are again available from Sigma Aldrich.

Where the process comprises carrying out a Suzuki reaction (i.e. a coupling involving an aryl boron reagent and the use of a palladium catalyst), the reaction may for example be carried out at elevated temperature (at a temperature for example in the range of from 30 to 100° C., or from 40-60° C.) or, more preferably, at ambient temperature (for example at a temperature in the range of from 15 to 40° C., depending on local ambient conditions).

Where the process comprises carrying out a Suzuki reaction (i.e. a coupling involving an aryl boron reagent and the use of a palladium catalyst), the reaction is typically carried out in the presence of water. The addition of water has been found to facilitate and accelerate the reaction. Accordingly, in preferred embodiments, the process comprises reacting a compound of formula (II) with an aryl-boron reagent in which the aryl moiety is a phenyl group substituted by $(Re)_n$ and by R or a protected version of R, in which R and $(Re)_n$ have the meanings given for the general formula (I), (I'), (Ia), (Ib) or (Ic), in the present of a palladium catalyst, and in the presence of water, e.g. an aqueous solvent system is used. Examples of suitable aqueous solvent systems include ether:water solvent systems, such as THF:water, 2-methyl THF:water, diethyl ether:water, diisopropyl ether:water, methyl tert-butyl ether:water, dimethoxyethane:water and 1,4-dioxane:water. Further examples include alcohol:water solvent systems, such as n-butanol:water, and toluene:water systems. In some preferred embodiments, the solvent system is THF:water, for example in a volume ratio of from 5:1 to 20:1, especially about 10:1.

It has also been found that the palladium-catalysed reaction between the aryl boron reagent and the compound of formula (II) proceeds particularly well in the absence or substantial absence of oxygen. Typically, reactions are run under an inert atmosphere, such as argon or nitrogen, following purging of air from the system. Multiple purge-refill cycles may be carried out to minimise the levels of oxygen remaining in the system. Thus, in some preferred embodiments, the Suzuki reaction is carried out in the absence or substantial absence of oxygen.

The Suzuki reaction has been found to work particularly well in the presence of water and in the substantial absence of oxygen. Thus in some preferred embodiments, the aryl-organometallic reagent is an aryl-boronic acid or aryl-boronate ester, and the reaction is carried out in the presence of a palladium catalyst in the presence of water and in the absence or substantial absence of oxygen.

The process of the invention unexpectedly provides access to a wide range of biaryl motifs comprising various functionality, and also provides direct access to certain compounds of formula (I), (I'), (Ia), (Ib) and (Ic) in high yield. The successful use of mild conditions in preparing the compounds of the invention is particularly surprising in view of the perceived reactivity of the sterically hindered electron-rich aryl chloride moiety in the compound of formula (II), and in view of the complex and sensitive chemical structure of the maytansinoid compound. The effectiveness of the process of the invention is surprising, particularly so as the use of a palladium catalyst might be expected to result in the degradation of the diene and/or epoxide portion of the maytansinoid core structure. This does not in fact happen.

It will be appreciated that, following the biaryl coupling step, the resulting compound may be subjected to further chemical transformation. For example, as described above, where the aryl-organometallic reagent contains a group R in protected form, the immediate product of the process will be in protected form also, and may be subjected to a deprotection step in which the protecting group is removed. As another example, where the product of the biaryl coupling step is a compound of formula (I), (I'), (Ia), (Ib) or (Ic), it may be converted into a further compound of formula (I), (I'), (Ia), (Ib) or (Ic) by subsequent chemical transformation (e.g. a compound in which R is —$NH_2$ may be converted into a compound in which R is —NH—C(O)—$C_{1-6}$alkyl-SH, or a compound in which R is —$CH_2OH$ may be converted by oxidation into a compound in which R is —$CO_2H$). As a further example, the compounds of formula (I), (I'), (Ia), (Ib) or (Ic) are useful for producing conjugating agents and conjugates, and the process may also comprise one or more further steps in which the compound of formula (I), (I'), (Ia), (Ib) or (Ic) is converted into a conjugating reagent of the invention, or into a conjugate of the invention.

Conjugates and Conjugating Reagents

The conjugates and reagents of the present invention contain a linker which, via the group R of the formula (I), (I'), (Ia), (Ib) or (Ic), connects the compound of formula (I), (I'), (Ia), (Ib) or (Ic) or a salt thereof, referred to herein as a payload or as drug D, to the binding protein in the conjugates of the invention or to the functional grouping in conjugating reagents of the invention. The conjugates and reagents may be represented schematically by:

D~linker~F' or

D~linker~F respectively, where D is the drug and F is the functional grouping of the reagent, which on reaction with a binding protein gives rise to the grouping F including the binding protein present in the conjugate.

Whilst in some embodiments, the linker may be a bond, for example in the case of conjugates comprising a compound of formula (I), (I'), (Ia), (Ib) or (Ic) which contains a pendant R group which can act as a spacer between the core maytansinoid structure and the binding protein, in other, preferred, embodiments the linker is other than a bond, e.g. the linker comprises a group which acts as a spacer between the drug and the binding protein, or between the drug and the functional group of the reagent which reacts with the binding protein.

In some preferred embodiments, the conjugate comprises a compound of formula (I').

The compounds of the invention can be made into conjugates, particularly antibody drug conjugates (ADCs) by linking the compound via the group R to an appropriate binding protein (e.g. antibody, antibody fragment, and the like) using linking chemistries known in the art. Exemplary linking chemistries include those based on maleimides or N-hydroxysuccinimides as disclosed within WO 2004/060965 and WO 2013/090590 respectively, and those disclosed in WO2014/064424A1.

As used herein, the term "binding protein" is meant to include both binding proteins and peptides, and except where the context specifically requires otherwise, should be understood to include peptides as well as proteins. Binding proteins that can be used in the conjugates of the invention include any protein, polypeptide or peptide that can serve as a binding agent for a binding partner on a target. The target may be for example a micro-organism, a virus, or a cell, for example a cancer or immune cell. The binding protein thus acts to target the compounds of the invention, the payload in a conjugate according to the invention, to the particular target. Examples of such binding proteins include full length antibodies, antibody fragments, immunoglobulin (Ig) and non-Ig protein scaffolds/antibody mimetics obtained by rational or combinatorial protein engineering techniques, and lectins. The most common binding proteins used in protein-drug conjugates are antibodies, and any reference to a binding protein should, except where the context specifically requires otherwise, be understood to include a specific reference to an antibody.

As used herein, "antibody" means an immunoglobulin molecule that recognizes and specifically binds to a target antigen, such as a protein, polypeptide, peptide, carbohydrate, polynucleotide, lipid, or combination thereof through at least one antigen recognition site within the variable region of the immunoglobulin molecule. The term "antibody" encompasses polyclonal antibodies, monoclonal antibodies, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can include any of the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. In one embodiment, the antibody is IgG1 or IgG4.

Further, except where the context requires otherwise, the term "antibody" should be understood to encompass full length antibodies and antibody fragments comprising an antigen-binding region of the full length antibody. Antibody fragments may for example be Fab, Fab', F(ab')$_2$, scFv, Fv, diabodies, minibodies or multispecific antibodies formed from antibody fragments, for example minibodies composed of different permutations of scFv fragments or diabodies, and optionally Fc fragments or CH domains, such as scFv-Fc, scFv-Fc-scFv, Fab-scFv, (Fab'ScFv)$_2$, scDiabodies, scDiabody-Fc, scDiabody-$C_H3$, scFv-$C_H3$, and SCFV-$C_H2$-$C_H3$ fusion proteins. An antibody fragment can be produced by enzymatic cleavage, synthetic or recombinant techniques.

A binding protein can serve as a binding agent for a receptor, antigen or other moiety on the surface of a target, for example a cell or virus associated with a proliferative, autoimmune or infectious disease. For example, the binding protein may be an antibody that specifically binds to a cell surface antigen on a cancer cell. Methods of identification and validation of cell surface antigens for antibody targeting of cancer cells are known, for example in Carter P, et al., Endocr. Relat. Cancer. 2004 December; 11(4):659-87, and a number of antibody-drug conjugates for treating cancer are currently in clinical development. Examples of antibodies available for the treatment of cancer, and tumor markers of specific cancers, are also well known in the art and can be used. Alternatively, the target may be an immune cell, for example a cell that is responsible for producing autoimmune antibodies, or an activated lymphocyte that is associated with an autoimmune disease. In other embodiments, the target may be a micro-organism or virus associated with a microbial or viral infection or disease.

An example of an antibody useful in the conjugates of the invention is an anti-CD30 antibody, for example a chimeric monoclonal antibody cAC10, e.g. brentuximab. A further example of an antibody useful in the conjugates of the invention is an anti-HER2 antibody, e.g. trastuzumab.

A conjugating reagent according to the invention comprises a compound according to the invention attached through the group R via a linker to a functional group F capable of reacting with a binding protein.

As mentioned above, any type of known conjugation reaction may be used to form the conjugates of the invention. For example, the reaction may be carried out using the known methods of thiol bonding, amine conjugation, or click chemistry. For example, the reagent may contain a maleimide group, an N-hydroxysuccinimide group, a click-chemistry group, for example an azide or alkyne group, an amine group, a carboxyl group, or an active ester group. Other possible approaches include the use of binding proteins that have been recombinantly engineered with an amino acid specifically for conjugation such as engineered cysteines or non-natural amino acids, and enzymatic conjugation through a specific enzymatic reaction such as with transglutaminase. Enzymatic conjugation can also be achieved using a Sortase enzyme which can, for example, conjugate linker-drug moieties to the sequence LPXTG that has been engineered into the binding protein. The reaction site on the binding protein may be either nucleophilic or electrophilic in nature. Common conjugation sites are at lysine or cysteine amino acid residues or carbohydrate moieties. Alternatively, conjugation may occur at a polyhistidine tag which has been attached to the binding protein.

Preferably the conjugating reagent comprises a functional group capable of reacting with at least one electrophile or, especially, nucleophile, present in the binding protein, and hence becoming chemically bonded thereto. As such the conjugating reagent typically includes at least one leaving group which is lost on reaction with a nucleophile. The conjugating reagent may, for example, include two or more leaving groups, and preferably the conjugating reagent according to the invention is capable of reacting with two nucleophiles. If two or more leaving groups are present, these may be the same or different. Alternatively, a conjugating reagent may contain a single group which is chemically equivalent to two leaving groups and which single group is capable of reacting with two nucleophiles.

Nucleophilic groups include sulfur atoms and amine groups, and nucleophilic groups in binding proteins are for example provided by cysteine, lysine or histidine residues.

In one preferred embodiment of the invention, a nucleophilic group is a sulfur atom present in a cysteine residue present in the binding protein. Such structures may be obtained by reduction of a disulfide bond present in the binding protein. In another embodiment, a nucleophilic group may be an imidazole group present in a histidine residue present in a polyhistidine tag attached to the binding protein.

One group of reagents is based on the bis-halo- or bis-thio-maleimides and derivatives thereof as described in Smith et al., *J. Am. Chem. Soc.*, 2010, 132, 1960-1965, and Schumacher et al., *Bioconj. Chem.*, 2011, 22, 132-136. These reagents contain the functional grouping:

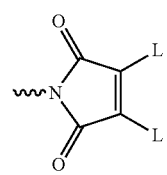

in which each L is a leaving group. The nitrogen atom of the maleimide ring is connected to the linking group.

Similarly, maleimides containing a single leaving group L:

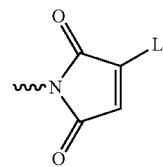

may be used. Again, the nitrogen atom of the maleimide ring is connected to the linking group.

Also, maleimides lacking a leaving group:

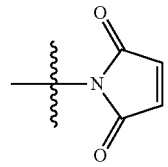 [SMILES: *N1C(=O)C=CC1=O]

may be used. Again, the nitrogen atom of the maleimide ring is connected to the linking group. For example, maleimide-based reagents may be reacted with a thiol moiety present in a binding protein, e.g. following reduction of a disulfide bond that may be present in the binding protein.

Another group of reagents are those described within WO2011/73391. An example of these reagents comprises the functional grouping:

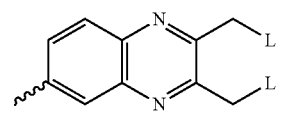

in which each L is a leaving group.

A further group of conjugating reagents are those based on activated acyl groups such as N-hydroxysuccinimide esters, i.e. which contain a functional group having the formula:

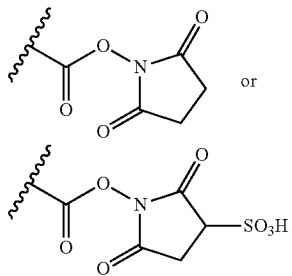

or a salt thereof. Functional groups of this type can be used to conjugate to binding proteins by, for example, an amidation reaction with a nucleophilic amine group present in the binding protein.

Another example of conjugating reagents are those containing a pyridyl disulfide group

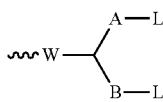

in which R' is either absent or represents an electron-withdrawing group, such as a —$NO_2$ group. Functional groups of this type can be used to conjugate to binding proteins by, for example, reaction with thiol moieties present in binding proteins (e.g. resulting from reduction of a disulfide bridge in the binding protein), resulting in a conjugate which itself contains a disulfide linkage.

In an especially preferred embodiment of the invention, the conjugating reagent contains the functional grouping F:

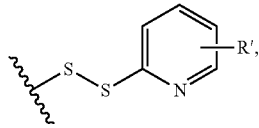

(V)

in which W represents an electron-withdrawing group, for example a keto group, an ester group —O—CO—, or a sulfone group —$SO_2$—; each of A and B independently represents a $C_{1-5}$alkylene or alkenylene chain; and either each L independently represents a leaving group, or both Ls together represent a leaving group. When reagents containing such groups react with proteins, a first leaving group L is lost to form in situ a conjugating reagent containing a functional grouping of formula:

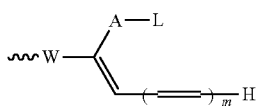

(VI)

in which m is 0 to 4, which reacts with a first nucleophile. The second leaving group L is then lost, and reaction with a second nucleophile occurs. As an alternative to using a reagent containing the functional grouping (V) as starting material, reagents containing the functional grouping (VI) may be used, as the functional groupings (V) and (VI) are chemical equivalents of each other.

These conjugating reagents of the invention are of the general type disclosed in WO 2005/007197 and WO 2010/100430. Such reagents may for example be used to target two sulfur atoms obtained by reduction of a disulfide bond, or imidazole groups present in histidine residues present in a polyhistidine tag.

A leaving group L may for example be —SP, —OP, —$SO_2$P, —$OSO_2$P, —$N^+PR^{13}R^{14}$, halogen, or —OØ, in which P represents a hydrogen atom or an alkyl (preferably $C_{1-6}$alkyl), aryl (preferably phenyl), or alkyl-aryl (preferably $C_{1-6}$alkyl-phenyl) group, or is a group which includes a portion —$(CH_2CH_2O)_q$— in which q is a number of six or more, and each of $R^{13}$ and $R^{14}$ independently represents a hydrogen atom, a $C_{1-4}$ alkyl group, or a group P, and Ø represents a substituted aryl, especially phenyl, group, containing at least one substituent, for example —CN, —$CF_3$, —$NO_2$, —$CO_2R^{aa}$, —COH, —$CH_2OH$, —$COR^{aa}$, —OC-$OR^{aa}$, —$OCO_2R^{aa}$, —$SR^{aa}$, —$SOR^{aa}$, —$SO_2R^{aa}$, —NHC-$OR^{aa}$, —$NR^{aa}_2$, $COR^{aa}$, —$NHCO_2R^{aa}$, —$NPCO_2R^{aa}$, —NO, —NHOH, —$NR^{aa}OH$, —CH=N—$NHCOR^{aa}$, —CH=N—$NR^{aa}COR^{aa}$, —$N^+R^{aa}_3$, —$N^+HR^{aa}_2$, —$N^+H_2R^{aa}$, halogen, especially chlorine or, especially, fluorine, —C≡$CR^{aa}$, —CH=$CR^{aa}_2$ and —CH=$CHR^{aa}$, in which each $R^{aa}$ represents a hydrogen atom or an alkyl (preferably $C_{1-6}$alkyl), aryl (preferably phenyl), or alkyl-aryl (preferably $C_{1-6}$alkyl-phenyl) group. The presence of electron withdrawing substituents is preferred.

Conjugating reagents in which P represents a group which includes a portion —$(CH_2CH_2O)_q$— in which q is a number of six or more are described in WO 2016/059377, and reagents including such leaving groups form one preferred embodiment of the invention. Such reagents may for example include —$(CH_2CH_2O)_q$—$R^1$ where $R^1$ is a capping group. $R^1$ may for example be a hydrogen atom, an alkyl group, especially a $C_{1-4}$alkyl group, particularly a methyl group, or an optionally substituted aryl group, for example an optionally substituted phenyl group, for example a tolyl group. Alternatively, the capping group may include a functional group such as a carboxyl group or an amine group. Such capping groups may for example have the formula —$CH_2CH_2CO_2H$ or —$CH_2CH_2NH_2$, and may be prepared by functionalising the terminal unit of a —$(CH_2CH_2O)_q$— chain. Alternatively, rather than being terminated by a capping group, the —$(CH_2CH_2O)_q$— group may have two points of attachment within the conjugating reagent such that chemically the equivalent of two leaving groups is present, capable of reacting with two nucleophiles.

The —$(CH_2CH_2O)_q$— portion of the leaving group is based on PEG, polyethylene glycol. The PEG may be straight-chain or branched, and it may be derivatised or functionalised in any way. q is a number of 6 or more, for example 6, 7, 8, 9 or 10, or more. For example, q may be from 6 to 9. There is no particular upper limit for q. q may for example be 150 or less, for example 120 or less, for example 100 or less. For example q may be from 6 or 7 to 150, for example from 6 or 7 to 120.

An especially preferred leaving group L present in a novel conjugating reagent according to the present invention is —SP or —$SO_2$P, especially —$SO_2$P. Within this group, one preferred embodiment is where P represents a phenyl or, especially, a tolyl group. Another preferred embodiment is where P represents a group which includes a portion —(CH$_2$CH$_2$O)$_q$—, especially one in which q has one of the values mentioned above, especially 7. Especially preferred leaving groups L are —SO$_2$—(CH$_2$CH$_2$O)$_q$—H and —SO$_2$—(CH$_2$CH$_2$O)$_q$-Me, especially —SO$_2$—(CH$_2$CH$_2$O)$_7$—H and —SO$_2$—(CH$_2$CH$_2$O)$_7$-Me. Throughout this Specification, any reference to a leaving group L should be understood to include a specific reference to these preferred groups, especially —SO$_2$—(CH$_2$CH$_2$O)$_q$—H and —SO$_2$—(CH$_2$CH$_2$O)$_q$-Me, and especially —SO$_2$—(CH$_2$CH$_2$O)$_7$—H and —SO$_2$ (CH$_2$CH$_2$O)$_7$-Me.

Preferably W represents a keto group. Preferably each of A and B represents —CH$_2$—, and m is 0.

Reagents of the formula V and VI above form conjugates which include the grouping F':

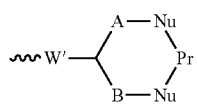
(VII)

in which W' represents an electron withdrawing group or a group obtained by reduction of an electron withdrawing group, and Pr represents the binding protein bonded to A and B via nucleophiles Nu. The immediate product of the conjugation process (as described in more detail below) is a conjugate which contains an electron-withdrawing group W. However, the conjugation process is reversible under suitable conditions. This may be desirable for some applications, for example where rapid release of the binding protein is required, but for other applications, rapid release of the binding protein may be undesirable. It may therefore be desirable to stabilise the conjugates by reduction of the electron-withdrawing moiety to give a moiety which prevents release of the binding protein. Accordingly, the conjugation process may comprise an additional optional step of reducing the electron withdrawing group in the conjugate. The use of a borohydride, for example sodium borohydride, sodium cyanoborohydride, potassium borohydride or sodium triacetoxyborohydride, as reducing agent is particularly preferred. Other reducing agents which may be used include for example tin(II) chloride, alkoxides such as aluminium alkoxide, and lithium aluminium hydride.

Thus, for example, a moiety W containing a keto group may be reduced to a moiety containing a CH(OH) group; an ether group CH.OR$^{aa}$ may be obtained by the reaction of a hydroxy group with an etherifying agent; an ester group CH.O.C(O)R$^{aa}$ may be obtained by the reaction of a hydroxy group with an acylating agent; an amine group CH.NH$_2$, CH.NHR$^{aa}$ or CH.NR$^{aa}{}_2$ may be prepared from a ketone by reductive amination; or an amide CH.NHC(O)R$^{aa}$ or CH.N(C(O)R$^{aa}$)$_2$ may be formed by acylation of an amine. A sulfone may be reduced to a sulfoxide, sulfide or thiol ether.

Preferably the groupings F' and F have the formula:

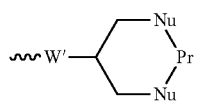
(VIIa)

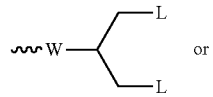
(Va)

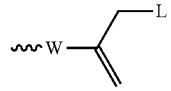
(VIa)

especially

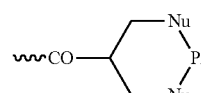
(VIIb)

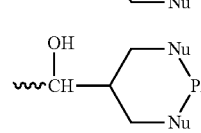
(VIIc)

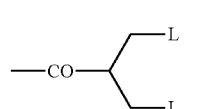
(Vb)

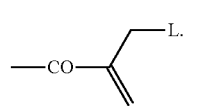
(VIb)

In the above formulae, preferred leaving groups are as described above. Preferably each Nu is a sulfur atom.

Another preferred group of conjugating reagents contains the functional grouping:

(VIII)

in which W has the meaning and the preferred meanings given above, and either:
each R$^{15}$ represents a hydrogen atom or a C$_{1-4}$alkyl group, R$^{15'}$ represents a hydrogen atom, and either each L and L' independently represents a leaving group, or both L and L' together represent a leaving group; or
each R$^{15}$ represents a hydrogen atom or a C$_{1-4}$alkyl group, L represents a leaving group, and R$^{15'}$ and L' together represent a bond.

Another group of conjugating reagents includes the functional grouping F:

(IX) or

(X)

in which W has the meaning and preferred meanings given above and p represents 0 or an integer of from 1 to 4, preferably 0. An especially preferred reagent of this type includes the functional grouping:

(IXa) or

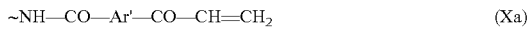
(Xa)

in which Ar' represents an optionally substituted aryl, especially phenyl, group.

In all cases, preferred meanings for leaving groups L and L' are as mentioned above.

Conjugating reagents according to the invention may contain more than one functional grouping for reaction with a binding protein. For example, a reagent may contain a functional grouping, preferably of formula (V) or (VI), at one end of the molecule, and one or more additional functional groupings, elsewhere in the molecule. Such structures are described in for example Belcheva et al, J. Biomater. Sci Polymer Edn. 9(3), 207-226 and are useful in the synthesis of conjugates containing multiple binding proteins and/or multiple payloads.

The novel conjugating reagents of the present invention may be prepared by methods analogous to known methods. It is a common feature of all the possible groups R in the formula (I) that they can readily be reacted with a complementary group on a linker. Thus, for example, a hydroxyl or thiol group may be reacted with an acid group on a linker to form an ester bond; an amino group may be reacted with an acid group (including an activated acid group such as DCC) to form an amide bond; a carboxyl group may be reacted with an amine group to form an amide bond, if desired by first activating the carboxyl group; a hydrazine may be reacted with an aldehyde or ketone to form a hydrazone or with a carboxylic acid to form a hydrazide, if desired by first activating the carboxyl group; an oxyamine group may be reacted with an aldehyde or ketone to form an oxime.

Conjugating reagents according to the invention may be reacted with a binding protein to form a conjugate according to the invention, and such a reaction forms a further aspect of the invention. Thus, a conjugating reagent including a suitable functional grouping, especially the functional grouping V or VI, is reacted with a binding protein, particularly with an antibody or antibody fragment, to form a conjugate, especially one including the grouping (VII).

A key feature of using conjugating reagents of the formulae (V) or (VI) is that an α-methylene leaving group and a double bond are cross-conjugated with an electron withdrawing function that serves as a Michael activating moiety. If the leaving group is prone to elimination in the cross-functional reagent rather than to direct displacement and the electron-withdrawing group is a suitable activating moiety for the Michael reaction then sequential intramolecular bis-alkylation can occur by consecutive Michael and retro Michael reactions. In reagents containing the functional grouping (V), a leaving group serves to mask a latent conjugated double bond that is not exposed until after the first alkylation has occurred to give a reagent including the functional grouping (VI) and bis-alkylation results from sequential and interactive Michael and retro-Michael reactions. The cross-functional alkylating agents may contain multiple bonds conjugated to the double bond or between the leaving group and the electron withdrawing group.

Where bonding to the binding protein is via two sulfur atoms derived from a disulfide bond in the protein, the process may be carried out by reducing the disulfide bond following which the reduced product reacts with the reagent according to the invention. Preferably the disulfide bond is reduced and any excess reducing agent is removed, for example by buffer exchange, before the conjugating reagent is introduced. The disulfide bond can be reduced, for example, with dithiothreitol, mercaptoethanol, or tris-carboxyethylphosphine using conventional methods.

In the case of conjugating agents comprising a group of formula (V) or (VI) for example, conjugation reactions may be carried out under similar conditions to known conjugation processes, including the conditions disclosed in WO 2005/007197, WO 2009/047500, WO 2014/064423 and WO 2014/064424.

Where conjugations are carried out using a conjugating reagent having an N-hydroxysuccinimide esters, e.g. by amidation reaction with a nucleophilic amine group present in the binding protein, conjugation reactions may be also carried out under similar conditions to known conjugation processes, including the conditions disclosed in, for example, Widdison et al, J. Med. Chem., 2006, 49 (14), p 4392-4408, WO2004/103272, WO2012/061590 or WO2013/090590. Similarly, for maleimide linking chemistries, conditions such as those disclosed in WO2004/010957 or WO2004/060965 may be used.

The process may for example be carried out in a solvent or solvent mixture in which all reactants are soluble. For example, the binding protein may be allowed to react directly with the polymer conjugating reagent in an aqueous reaction medium. This reaction medium may also be buffered, depending on the pH requirements of the nucleophile. The optimum pH for the reaction will generally be at least 4.5, typically between about 5.0 and about 8.5, preferably about 6.0 to 7.5. The optimal reaction conditions will of course depend upon the specific reactants employed.

Reaction temperatures between 3-40° C. are generally suitable when using an aqueous reaction medium. Reactions conducted in organic media (for example THF, ethyl acetate, acetone, acetonitrile, DMF, DMA) are typically conducted at temperatures up to ambient. In one preferred embodiment, the reaction is carried out in aqueous buffer which may contain a proportion of organic solvent, for example up to 50% by volume of organic solvent, typically from 5 to 20% by volume of organic solvent.

The binding protein can be effectively conjugated using a stoichiometric equivalent or a slight excess of conjugating reagent. However, it is also possible to conduct the conjugation reaction with an excess stoichiometry of conjugating reagent, and this may be desirable for some proteins, or if conjugates containing a higher average ratio of drug to antibody (higher DAR) are desired. The excess reagent can easily be removed, for example by ion exchange chromatography or HPLC, during subsequent purification of the conjugate.

Of course, it is possible for more than one conjugating reagent to be conjugated to a binding protein, where the protein contains sufficient suitable attachment points. For example, in a binding protein which contains two different disulfide bonds, or in a binding protein which contains one disulfide bond and also carries a polyhistidine tag, it is possible to conjugate two molecules of reagent per molecule of binding protein using a conjugating reagent of formula (V) or (VI), and such conjugates form part of the present invention.

The Linker

The linker which connects the payload, via the group R of the general formula (I), (I'), (Ia), (Ib) or (Ic) to the binding protein in a conjugate according to the invention or to the functional grouping capable of reaction with a binding protein in a conjugating reagent according to the invention may contain any desired groups, for example any of the conventional groups commonly found in this field.

Linker Subsection (i).

In one embodiment, the linker between the payload and the grouping of formula F'/F, and particularly that portion of the linker immediately adjacent the grouping of formula F'/F in conjugates or reagents of the formulae (V), (VI), (VII), (VIII), (IX) and (X), may include an alkylene group (preferably a $C_{1-10}$ alkylene group), or an optionally-substituted aryl or heteroaryl group, any of which may be terminated or interrupted by one or more oxygen atoms, sulfur atoms, —NR$^{aa}$ groups (in which R$^{aa}$ represents a hydrogen atom or an alkyl (preferably C$_{1-6}$alkyl), aryl (preferably phenyl), or alkyl-aryl (preferably C$_{1-6}$alkyl-phenyl) group), keto groups, —O—CO— groups, —CO—O— groups, —O—CO—O—, —O—CO—NR$^{aa}$—, —NR—CO—O—, —CO—NR$^{aa}$— and/or —NR$^{aa}$.CO— groups. Suitable aryl groups include phenyl and naphthyl groups, while suitable heteroaryl groups include pyridine, pyrrole, furan, pyran, imidazole, pyrazole, oxazole, pyridazine, pyrimidine and purine. Especially preferred as that portion of the linker immediately adjacent the group F/F' are aryl groups, especially phenyl groups. Further especially preferred as that portion of the linker immediately adjacent the group F/F' are heteroaryl groups, for example one of those mentioned above.

The aryl or heteroaryl group may be adjacent a further portion of the linking group which is, or contains, a —NR$^{aa}$.CO— or —CO.NR$^{aa}$— group, for example an —NH.CO— or —CO.NH— group. Here and elsewhere throughout this Specification, where a group R$^{aa}$ is present, this is preferably a C$_{1-4}$alkyl, especially a methyl group or, especially, a hydrogen atom.

Substituents which may be present on an optionally substituted aryl, especially phenyl, or heteroaryl group include for example one or more of the same or different substituents selected from alkyl (preferably C$_{1-4}$alkyl, especially methyl, optionally substituted by OH or CO$_2$H), —CF$_3$, —NR$^{aa}$$_2$, —CN, —NO$_2$, —CO$_2$R$^{aa}$, —COH, —CH$_2$OH, —COR$^{aa}$, —OR$^{aa}$, —OCOR$^{aa}$, —OCO$_2$R$^{aa}$, —SR$^{aa}$, —SOR$^{aa}$, —SO$_2$R$^{aa}$, —NHCOR$^{aa}$, —NR$^{aa}$COR$^{aa}$, —NHCO$_2$R$^{aa}$, —NR$^{aa}$.CO$_2$R$^{aa}$, —NO, —NHOH, —NR$^{aa}$.OH, —CH=N—NHCOR$^{aa}$, —CH=N—NR$^{aa}$.COR$^{aa}$, —N$^+$R$^{aa}$$_3$, —N$^+$HR$^{aa}$$_2$, —N$^+$H$_2$R$^{aa}$, halogen, for example fluorine or chlorine, —C≡CR$^{aa}$, —CH=CR$^{aa}$$_2$ and —CH=CHR$^{aa}$, in which each R$^{aa}$ independently represents a hydrogen atom or an alkyl (preferably C$_{1-6}$alkyl), aryl (preferably phenyl), or alkyl-aryl (preferably C$_{1-6}$alkyl-phenyl) group. The presence of electron withdrawing substituents is especially preferred. Preferred substituents include for example CN, NO$_2$, —OR$^{aa}$, —OCOR$^{aa}$, —SR$^{aa}$, —NHCOR$^{aa}$, —NHOH and —NR$^{aa}$.COR$^{aa}$.

Preferably the linker includes one of the above groups adjacent the grouping F'/F. Especially preferred are conjugates and conjugating reagents which include the grouping:

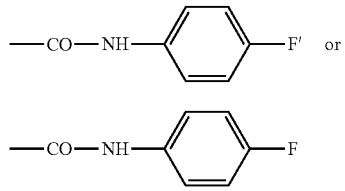

(XI)

(XII)

or, especially:

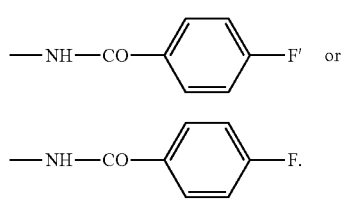

(XIII)

(XIV)

Also suitable are conjugates and conjugating reagents of the formulae: —CO—NH-Het-F', —CO—NH-Het-F, —NH—CO-Het-F', and —NH—CO-Het-F, in which Het represents a heteroaryl group, for example one of those mentioned above.

Any of the above structures may be adjacent to any of the structures mentioned in subsections (ii) and (iii) below.

In all the above formulae, especially the formulae (XI), (XII), (XIII) and (XIV), preferably F' has the formula (VII), for example (VIIa), (VIIb) or (VIIc) above, and preferably F has the formula (V) or (VI), for example (Va), (Vb), (VIa) or (VIb) above.

Linker Subsection (ii).

In one embodiment, the linker may contain a degradable group, i.e. it may contain a group which breaks under physiological conditions, separating the payload from the protein to which it is, or will be, bonded. Alternatively, it may be a linker that is not cleavable under physiological conditions. Where a linker breaks under physiological conditions, it is preferably cleavable under intracellular conditions. Where the target is intracellular, preferably the linker is substantially insensitive to extracellular conditions (i.e. so that delivery to the intracellular target of a sufficient dose of the therapeutic agent is not prohibited).

Where the linker contains a degradable group, this is generally sensitive to hydrolytic conditions, for example it may be a group which degrades at certain pH values (e.g. acidic conditions). Hydrolytic/acidic conditions may for example be found in endosomes or lysosomes. Examples of groups susceptible to hydrolysis under acidic conditions include hydrazones, semicarbazones, thiosemicarbazones, cis-aconitic amides, orthoesters and ketals. Examples of groups susceptible to hydrolytic conditions include:

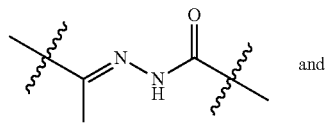 and

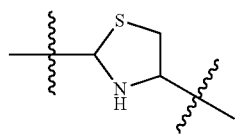

In a preferred embodiment, the linker includes

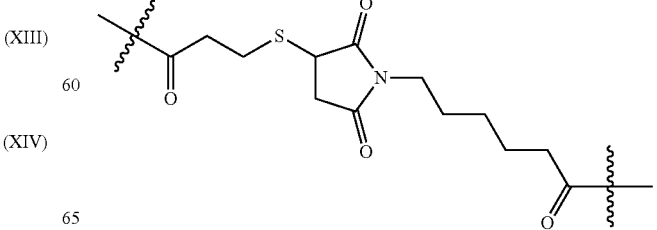

For example, it may include:

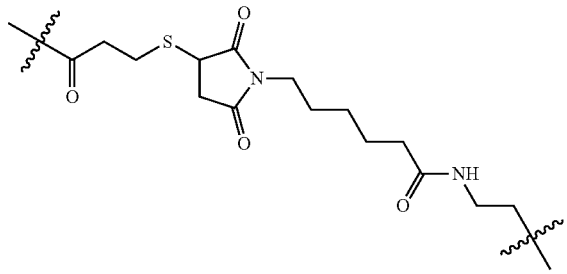

The linker may also be susceptible to degradation under reducing conditions. For example, it may contain a disulfide group that is cleavable on exposure to biological reducing agents, such as thiols. Examples of disulfide groups include:

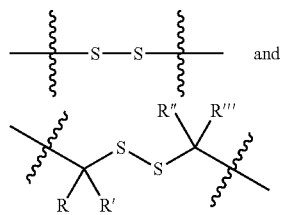

in which R, R', R" and R'" are each independently hydrogen or $C_{1-4}$alkyl. In a preferred embodiment the linker includes

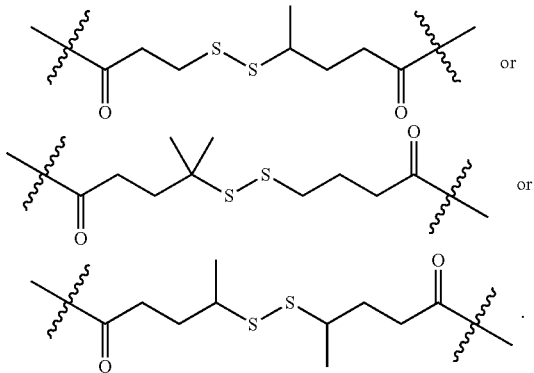

For example, it may include

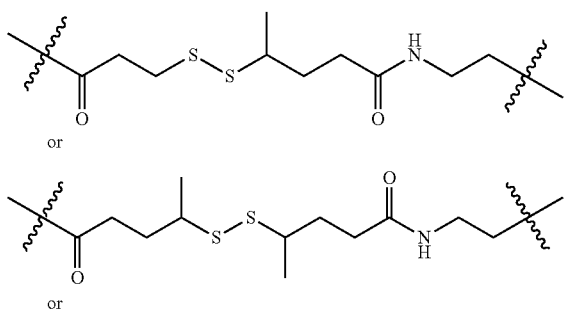

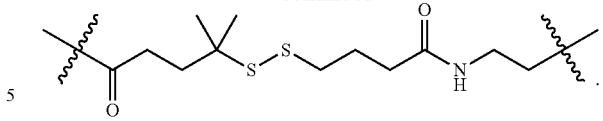

The linker may also contain a group which is susceptible to enzymatic degradation, for example it may be susceptible to cleavage by a protease (e.g. a lysosomal or endosomal protease) or peptidase. In an especially preferred embodiment of the invention, a portion of the linker contains a peptidyl group comprising at least one, for example at least two, at least three, at least four or at least five amino acid residues, specifically naturally-occurring alpha amino acids. For example, that portion of the linker may contain the sequence Phe-Leu, Gly-Phe-Leu-Gly, Val-Ala, Val-Cit, Phe-Lys, or Glu-Glu-Glu, and presence of a Val-Cit peptidyl group is preferred. Linkers containing the sequence Val-Cit-PAB, as discussed below, are especially preferred.

A particularly preferred example of a group susceptible to enzymatic degradation is:

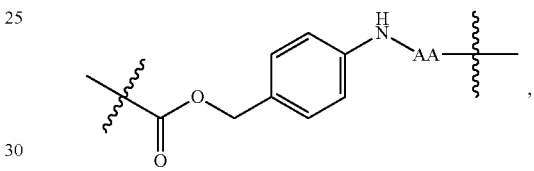

wherein AA represents a protease-specific amino acid sequence, such as one of those mentioned above, especially Val-Cit. In other words, in a preferred embodiment the linker includes:

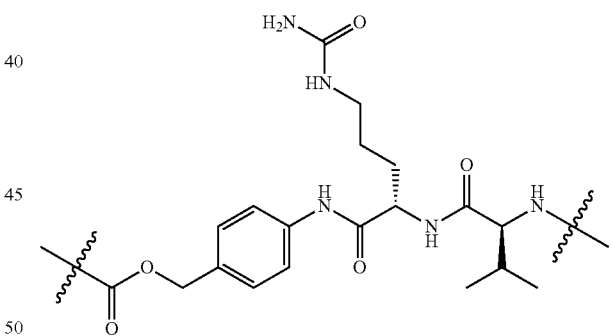

For example, it may include

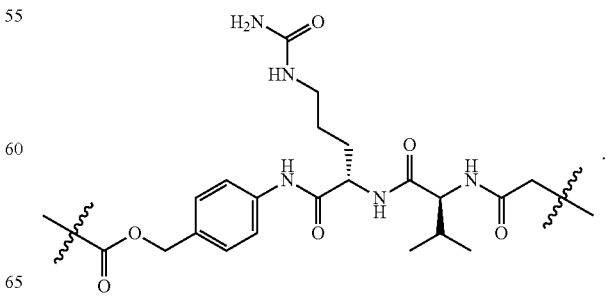

In some preferred embodiments, the PAB portion of the linker (i.e. the benzyloxycarbonyl portion) may be directly linked to the R group of the drug moiety (e.g. to the residue of an —NH$_2$ group thus forming a carbamate moiety, in the case where R is —NH$_2$ in the compounds of formula (I), (I'), (Ia), (Ib) or (Ic), and the nitrogen of the Val group may be connected to the remainder of the linker.

As discussed above, in some embodiments the compound of formula (I), (I'), (Ia), (Ib) or (Ic) may contain an R group of the formula —NH—C(O)—C$_{1-6}$alkylene-SH. When incorporated into a conjugate or conjugating reagent of the invention, this may be achieved by use of a disulfide linkage, e.g.:

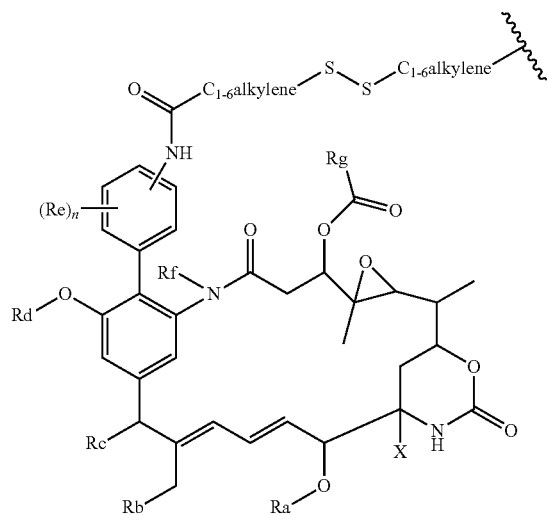

In such cases, the linker portion of the conjugate or conjugating reagent may be considered to contain an —S—C$_{1-6}$alkylene- group, which can be cleaved by reduction of the disulfide bond to release the compound of formula (I) containing the R group of the formula —NH—C(O)—C$_{1-6}$alkylene-SH. For example, in some embodiments the linker comprises an —S—C$_{1-6}$alkylene-group selected from the following:

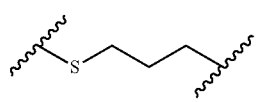

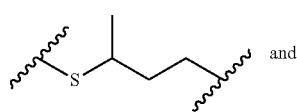 and

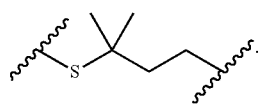

Conjugates of this type may, for example, by synthesized from a compound of formula (I), (I'), (Ia), (Ib) or (Ic) in which the R group is an —NH$_2$ group, e.g. by an amidation reaction with a suitable carboxylic acid or carboxylic acid derivative. As a result, the linker group may instead be considered to contain a group:

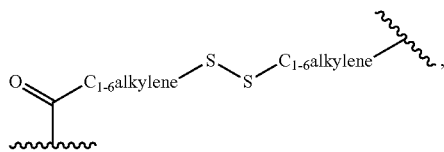

e.g. a linker group containing a disulfide group that is cleavable on exposure to biological reducing agents, as described above.

The conjugates of the invention comprise a binding protein conjugated to the drug D via the residue of the R group (e.g. via an —NH— group in the case of a compound of formula (I) in which R is —NH$_2$, or via a group —NHC(O)C$_{1-6}$alkylene-S—, in the case of a compound of formula (I) in which R is —NHC(O)C$_{1-6}$alkylene-SH).

The linker may carry a single payload D, or more than one group D. Multiple groups D may be incorporated by the use of a branching linker, which may for example incorporate an aspartate or glutamate or similar residue. This introduces a branching element of formula:

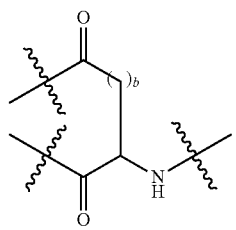

where b is 1, 2, 3 or 4, b=1 being aspartate and b=2 being glutamate, and b=3 representing one preferred embodiment. Each of the acyl moieties in the above formula may be coupled to a group D. The branching group above may incorporate a —CO.CH$_2$— group, thus:

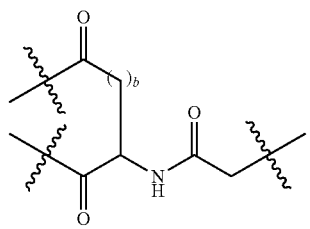

If desired, the aspartate or glutamate or similar residue may be coupled to further aspartate and/or glutamate and/or similar residues, for example:

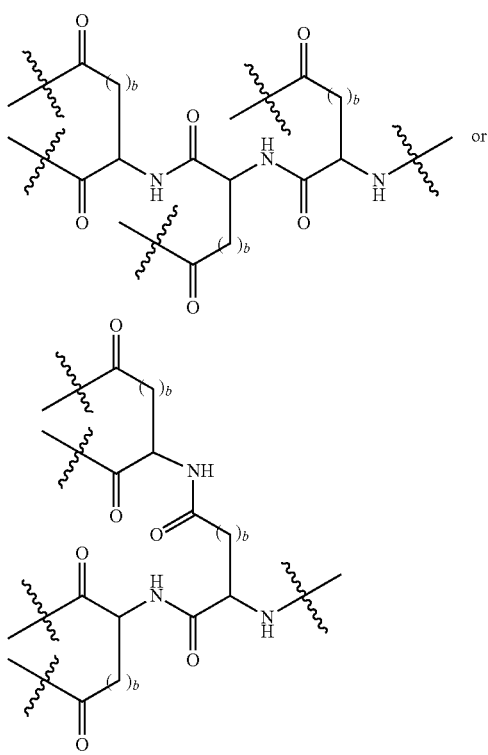

and so on.

In a similar way, the amino acids lysine, serine, threonine, cysteine, arginine or tyrosine or similar residues (e.g. lysine or serine) may be introduced to form a branching group, thus:

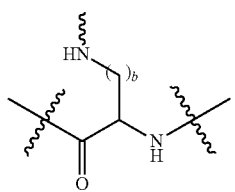

in which b is 4 for lysine, and

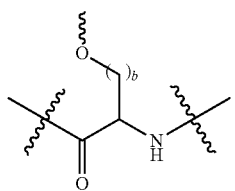

in which b is 1 for serine.

Linker Subsection (iii).

The linker of the reagents and conjugates of the present invention may if desired contain an oligomer or polymer (jointly referred to herein as "polymer" for convenience). A polymer may for example be a polyalkylene glycol, a polyvinylpyrrolidone, a polyacrylate, for example polyacryloyl morpholine, a polymethacrylate, a polyoxazoline, a polyvinylalcohol, a polyacrylamide or polymethacrylamide, for example polycarboxymethacrylamide, or a HPMA copolymer. Additionally, the polymer may be a polymer that is susceptible to enzymatic or hydrolytic degradation. Such polymers, for example, include polyesters, polyacetals, poly (ortho esters), polycarbonates, poly(imino carbonates), and polyamides, such as poly(amino acids). A polymer may be a homopolymer, random copolymer or a structurally defined copolymer such as a block copolymer, for example it may be a block copolymer derived from two or more alkylene oxides, or from poly(alkylene oxide) and either a polyester, polyacetal, poly(ortho ester), or a poly(amino acid). Polyfunctional polymers that may be used include copolymers of divinylether-maleic anhydride and styrene-maleic anhydride.

Naturally occurring polymers may also be used, for example polysaccharides such as chitin, dextran, dextrin, chitosan, starch, cellulose, glycogen, poly(sialylic acid), hyaluronic acid and derivatives thereof. Polymers such as polyglutamic acid may also be used, as may hybrid polymers derived from natural monomers such as saccharides or amino acids and synthetic monomers such as ethylene oxide or methacrylic acid.

A polymer is preferably a water soluble, synthetic polymer, particularly polyalkylene glycol. If the polymer is a polyalkylene glycol, this is preferably one containing $C_2$ and/or $C_3$ units, and is especially a polyethylene glycol. A polymer, particularly a polyalkylene glycol, may contain a single linear chain, or it may have branched morphology composed of many chains either small or large. Substituted, or capped, polyalkylene glycols, for example methoxypolyethylene glycol, may be used.

A polymer may optionally be derivatised or functionalised in any desired way. Reactive groups may be linked at the polymer terminus or end group, or along the polymer chain through pendant linkers.

If PEG is present in the linker, the optimal number of $-(CH_2-CH_2-O-)-$ units present in the linker of the conjugates and reagents of the invention will of course depend on the intended application. For some applications, high molecular weight PEGs may be used, for example the number average molecular weight may be up to around 75,000, for example up to 50,000, 40,000 or 30,000 g/mole. For example, the number average molecular weight may be in the range of from 500 to around 75,000 g/mole. However, smaller PEG portions may be preferred for some applications. For example a PEG portion of the linker may have a molecular weight up to 3,000 g/mole. However, PEG groups containing as few as 2 repeat units, for example from 2 to 50 repeat units, are useful for some applications. PEG-containing portions with 2, 3, 4, 5, 6, 7, 8, 9 or 10 repeat units, or 12, 20, 24, 36, 40 or 48 repeat units, may for example be present in the linker.

WO 2016/063006 describes reagents and conjugates having PEG-containing linkers of a particular structure, and reagents and conjugates including such linkers form one preferred embodiment of the invention.

In such reagents and conjugates, there is a PEG portion which is or includes a pendant PEG chain which has a terminal end group of formula $-CH_2CH_2OR''$ in which $R''$ represents a hydrogen atom, an alkyl group, for example a $C_{1-4}$alkyl group, especially a methyl group, or an optionally substituted aryl group, especially a phenyl group, especially an unsubstituted phenyl group.

Conjugates of this type may be represented schematically by the formula:

in which D represents the novel payload of the present invention, F' represents the binding protein, and PEG represents the pendant polyethylene glycol chain having a terminal end group of formula —$CH_2CH_2OR^r$.

Reagents of this type may be represented schematically by the formula:

 (IV)

in which D represents the payload of the present invention, F represents the functional grouping capable of reacting with a binding protein, and PEG represents the pendant polyethylene glycol chain having a terminal end group of formula —$CH_2CH_2OR^r$. The functional grouping F is preferably capable of reacting with two nucleophiles present in a protein or peptide as explained above, and is preferably of the formula (V), (VI), or (VIII), especially (V) or (VI).

In one preferred embodiment, all of the PEG in the PEG portion of the linker is present in the pendant PEG chain. In another embodiment, PEG may also be present in the backbone of the conjugate or reagent.

As with the overall PEG portion, the size of the pendant PEG chain will depend on the intended application. For example said pendant PEG chain may have a molecular weight up to 3,000 g/mole. However, very small oligomers, consisting of discrete PEG chains with, for example, as few as 2 repeat units, for example from 2 to 50 repeat units, are useful for some applications, and are present as said PEG chain in one preferred embodiment of the invention. The pendant PEG chain may be straight-chain or branched. PEG chains, for example straight-chain or branched chains with 12, 20, 24, 36, 40 or 48 repeat units may for example be used.

Conjugates and reagents in which the linker includes at least two ~($CH_2$—$CH_2$—O—)~ units within a ring are also contemplated. For example, the ring may be attached via a single tethering atom within the ring to the rest of the linker, or the ring may be attached via two or more tethering atoms within the ring to the rest of the linker at a single point.

Conjugates of this type may be represented schematically by the formula:

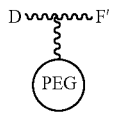

in which D represents the payload of the present invention, F' represents the protein or peptide bonded to the remainder of the conjugate via a protein or peptide bonding portion of the linker, and 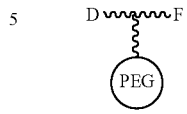 represents a ring which includes at least two ethylene glycol, ~($CH_2$—$CH_2$—O—)~, units.

Reagents of this type may be represented schematically by the formula:

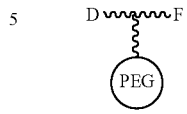

in which D represents the payload of the present invention, F represents a functional grouping capable of bonding to a protein or peptide, and 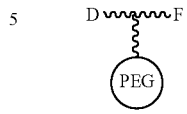 represents a ring which includes at least two ethylene glycol, ~($CH_2$—$CH_2$—O—)~, units. The functional grouping F is capable of reacting with a protein or peptide as explained in more detail below.

Tethering atoms may for example be nitrogen, carbon, phosphorus or silicon atoms, especially nitrogen and/or carbon atoms, and the atoms present at the point of attachment to the rest of the linker may for example be nitrogen or carbon atoms.

The following are schematic drawings of possible forms of attachment of the ring to the rest of the linker in conjugates or reagents of the invention, T representing a tethering atom in the ring, and PEG representing at least two ~($CH_2$—$CH_2$—O—)~ units:

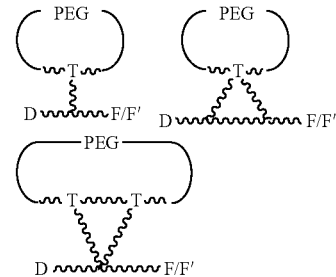

Specific examples of suitable rings include the following, where the symbol ~ indicates a point of incorporation of the ring into the linker:

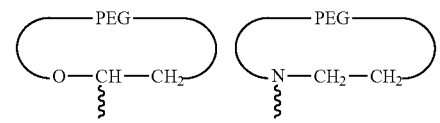

Preferably the ring is attached to the rest of the linker at a single point, and most preferably the ring is attached via a single tethering atom in the ring to the rest of the linker at a single point.

The ring may for example consist of ~($CH_2$—$CH_2$—O—)$_x$~ units in which x is at least 2, preferably from 2 to 20. Alternatively, the ring may contain ~($CH_2$—$CH_2$—O—)$_x$~ units in which x is at least 2, preferably from 2 to 50, especially from 2 to 20, but may also include one or more additional atoms as mentioned above, or may be derivatised in some other way. PEG-containing rings with 2, 3, 4, 5, 6, 7, 8, 9, 10, 11, 12, 13, 14, 15, 16, 17, 18, 19 or 20 repeat units, or 24, 36, 40 or 48 repeat units, may for example be used.

Conjugates and reagents may be readily synthesised from crown ethers. Crown ethers are cyclic oligomers of ethylene glycol, and many different crown ethers are known, some of which consist entirely of ethylene glycol units, and some of which contain additional atoms within the ring. For example, aza-crown ethers contain a nitrogen atom, while diaza-crown ethers contain two nitrogen atoms. Many crown ethers are commercially available, and these provide convenient starting points for synthesis of the conjugates and reagents according to the invention. Crown ethers carrying functional groups through which they may be reacted with other compounds are known, for example crown ethers carrying carboxy, hydroxy, amino, or aldehyde groups are known, as are crown ethers fused to a benzene ring optionally carrying a functional group such as a carboxy, hydroxy, amino, isocyanate, nitro or aldehyde group.

Typical crown ethers which can be incorporated into the conjugates and reagents according to the invention include the structures shown below.

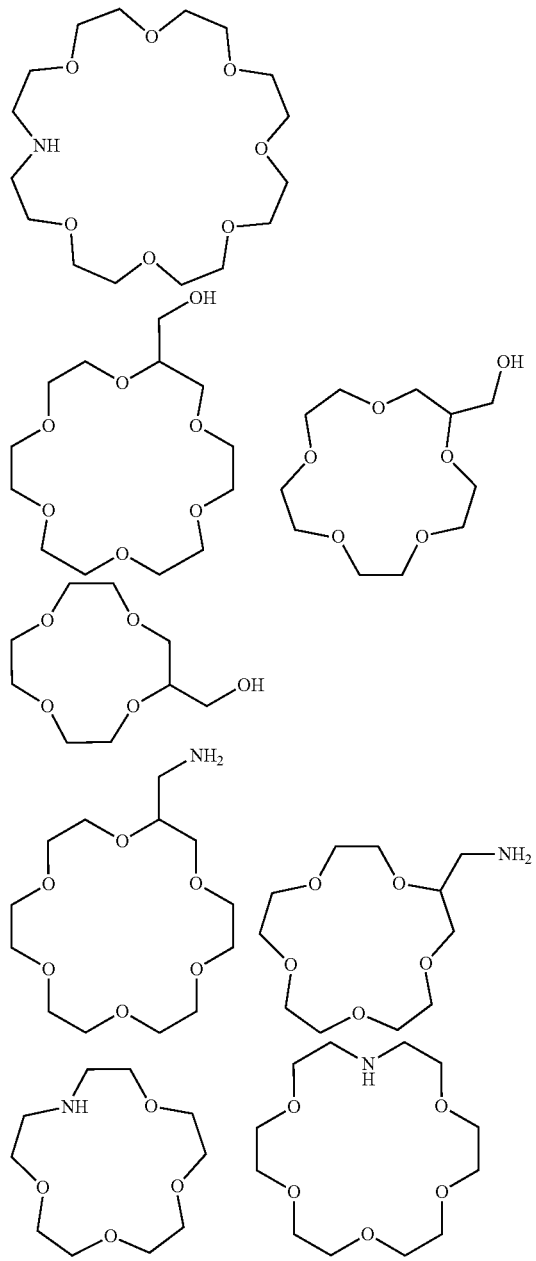

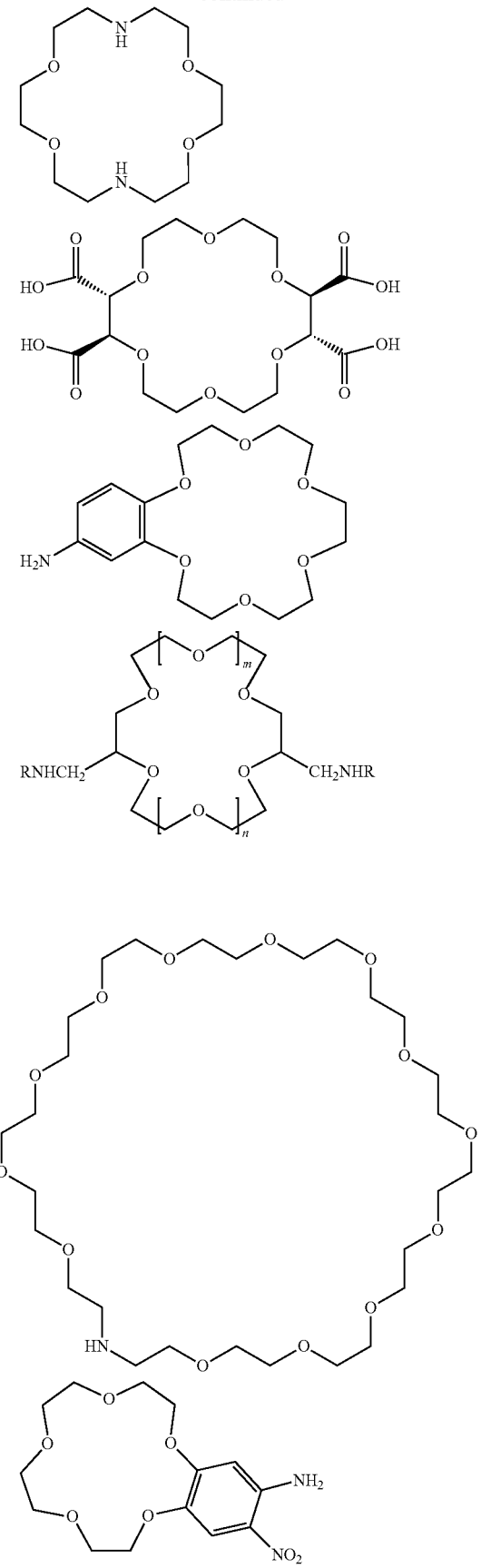

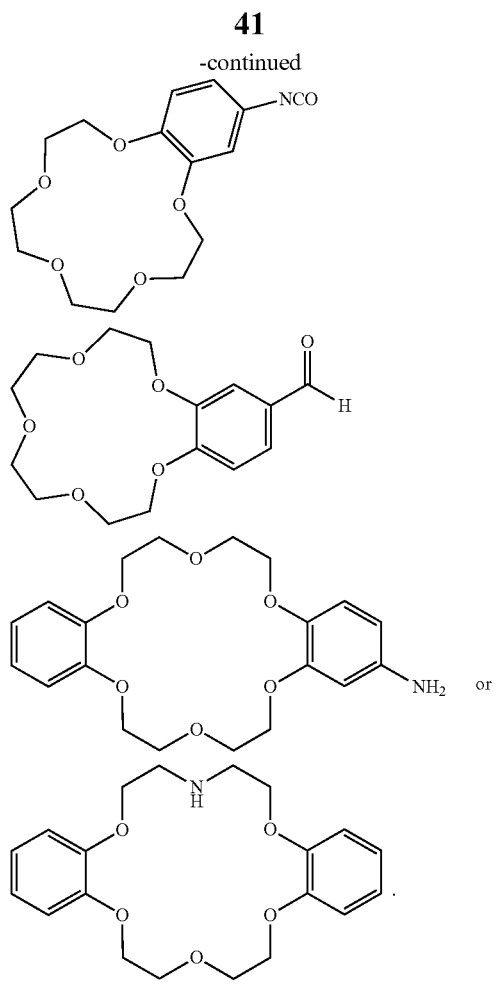

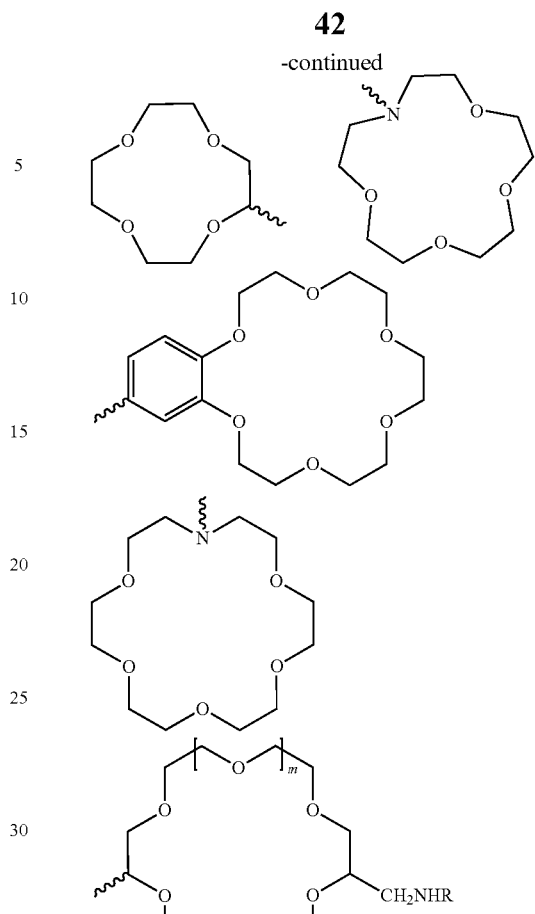

These may be attached to the backbone of the linker of the conjugates and reagents of the invention by reaction through atoms, especially nitrogen atoms, present within the ring, or via groups, for example hydroxy, amino, carboxy, aldehyde, isocyanate or nitro groups, present on a side-chain. Typical linkages are as shown below:

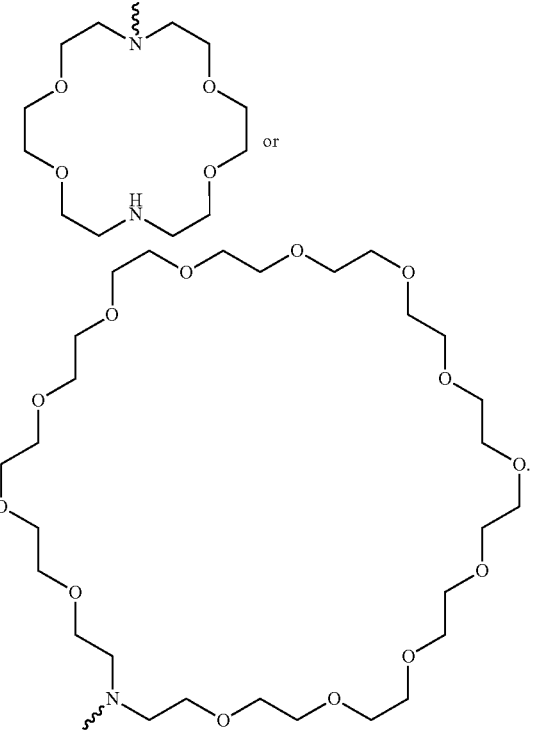

Conjugates and reagents are also contemplated in which the linker includes a cyclodextrin. For example, the cyclodextrins may be an α-cyclodextrin, β-cyclodextrin, or γ-cyclodextrin. In conjugates comprising a cyclodextrin, the cyclodextrin may for example be bonded to the rest of the linker via the 3- or the 6-position, for example via an amino functionalised cyclodextrin. In some embodiments of conjugates and reagents of this type, the cyclodextrins may be monocyclic. In some embodiments of conjugates and reagents of this type, the cyclodextrin may be present as a pendant group which is tethered to the backbone of the linker.

In some embodiments, the conjugating reagent may be represented schematically by the formula

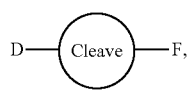

and/or the conjugate may be represented schematically by the formula

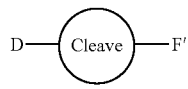

in which D represents the payload of the present invention, for example a group of formula:

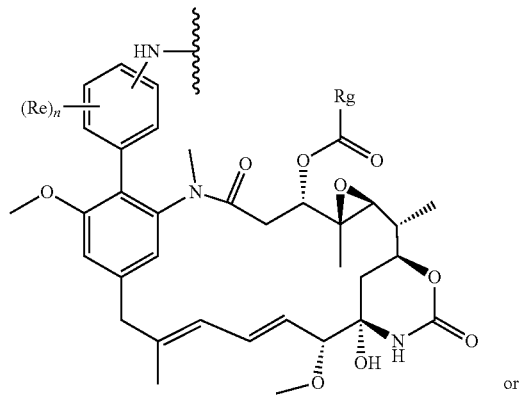

or

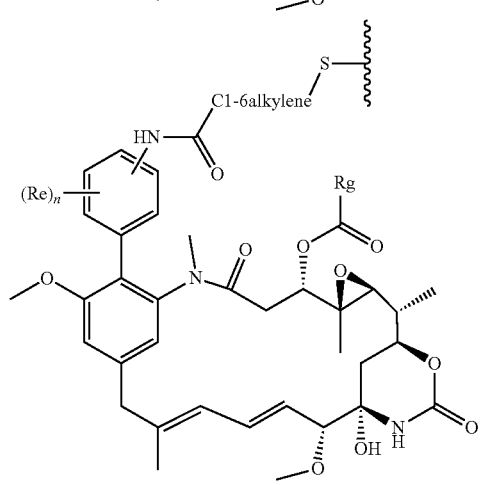

in which Rg is —C(CH$_3$)$_2$ or

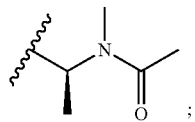 [SMILES: *[C@H](C)N(C)C(C)=O]

n is 0 or 1; Re is either absent or where present is chlorine, fluorine, methoxy, —CN or NO$_2$;

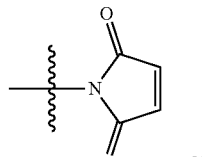 represents a group including a moiety which, when present in a conjugate of the invention, facilitates degradation of the conjugate under physiological conditions, such as an -Ala-Val- or -PAB-Cit-Val- group in the case where D is conjugated via a —NH— group, or a sulfur-containing group which is covalently bound to another sulfur atom present in the conjugate (i.e. resulting in a disulfide —S—S— moiety being present in the conjugate), such as a group containing a —S—C$_{1-6}$alkylene- moiety in the case where D is conjugated via a —NH—C(O)—C$_{1-6}$alkylene-S— group;

F represents the functional grouping capable of reacting with a binding protein, such as

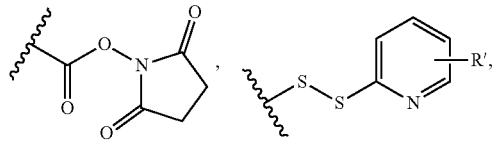

in which R' is either absent or represents an electron-withdrawing group, such as a —NO$_2$ group, or F represents

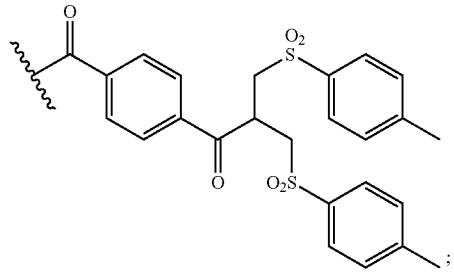

and F' represents the protein or peptide bonded to the remainder of the conjugate via the residue of the functional group.

For example, conjugating reagents of this type may have the structure:

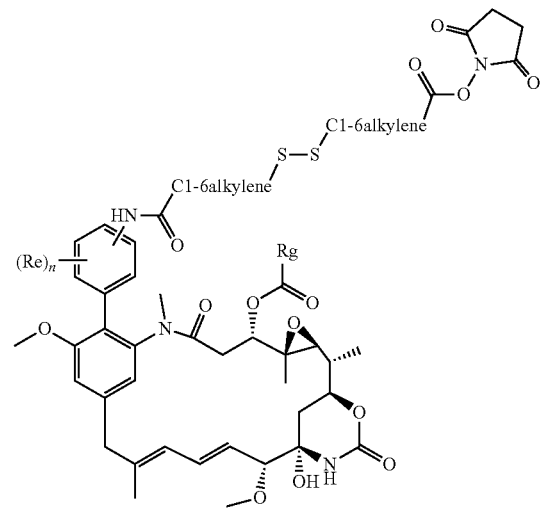

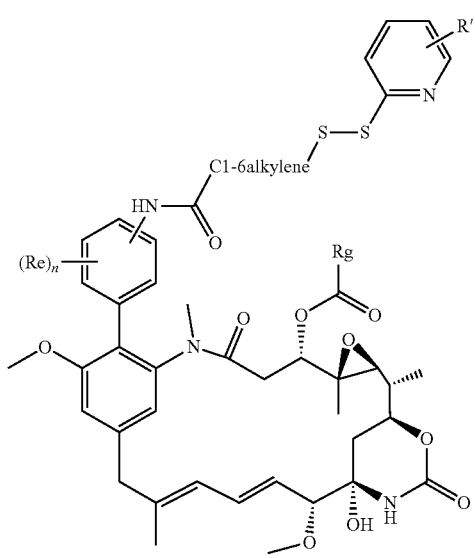

in which Rg is —C(CH₃)₂ or

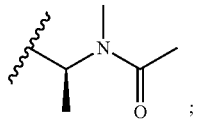 [SMILES: *[C@H](C)N(C)C(C)=O]

n is 0 or 1; Re is either absent or where present is chlorine, fluorine, methoxy, —CN or —NO₂, and R' is either absent or represents an electron-withdrawing group, such as a —NO₂ group; and conjugates may have the corresponding structure resulting from reaction of the protein or peptide bonding portion of the linker with the protein or peptide.

In some embodiments, the conjugating reagent may be represented schematically by the formula

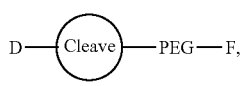

and/or the conjugate may be represented schematically by the formula

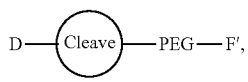

in which D represents the payload of the present invention, for example a group of formula:

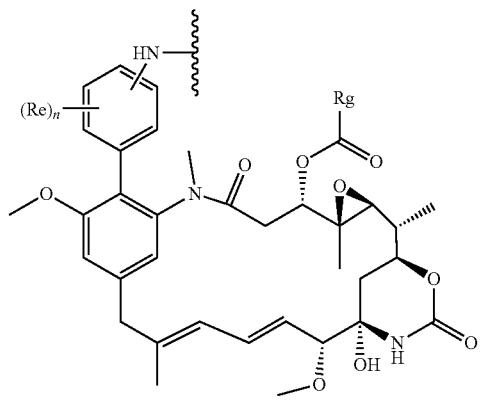

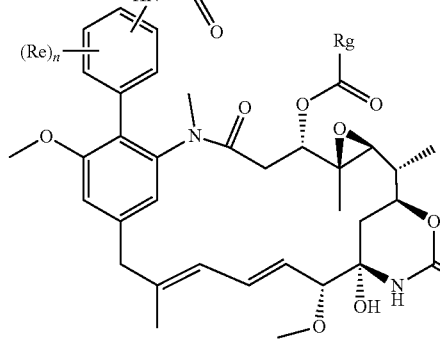

in which Rg is —C(CH$_3$)$_2$ or

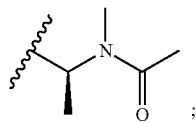 [SMILES: *[C@H](C)N(C)C(C)=O]

n is 0 or 1; Re is either absent or where present is chlorine, fluorine, methoxy, —CN or —NO$_2$;

(Cleave) represents a group including a moiety which, when present in a conjugate of the invention, facilitates degradation of the conjugate under physiological conditions, such as an -Ala-Val- or -PAB-Cit-Val- group in the case where D is conjugated via a —NH— group, or a sulfur-containing group which is covalently bound to another sulfur atom present in the conjugate (i.e. resulting in a disulfide —S—S— moiety being present in the conjugate), such as a group containing a —S—C$_{1-6}$alkylene- moiety in the case where D is conjugated via a —NH—C(O)—C$_{1-6}$ alkylene-S— group; PEG represents a polyethylene glycol-containing group; and F represents the functional grouping capable of reacting with a binding protein, such as

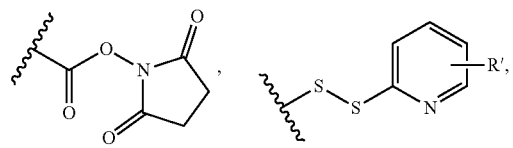

in which R' is either absent or represents an electron-withdrawing group, such as a —NO$_2$ group, or F represents

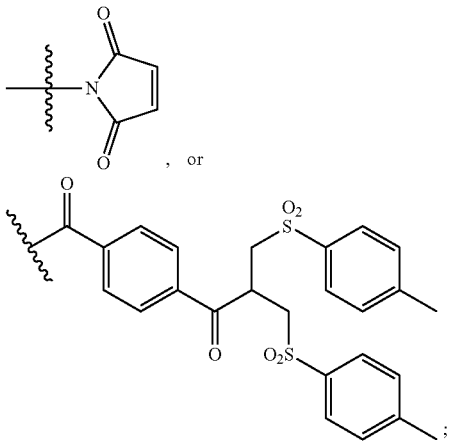

and F' represents the protein or peptide bonded to the remainder of the conjugate via the residue of the functional group.

For example, conjugating reagents of this type may have the structure:

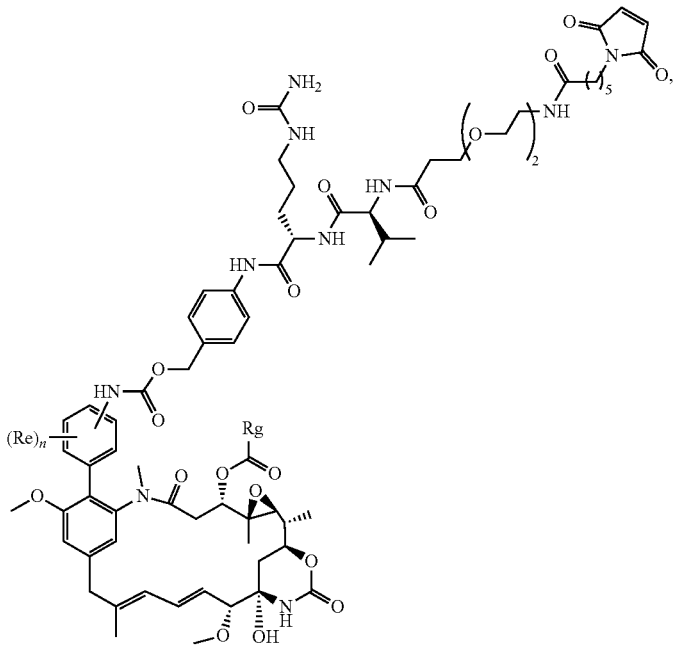

in which Rg is —C(CH$_3$)$_2$ or

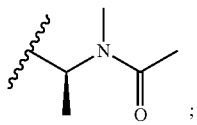 [SMILES: *[C@H](C)N(C)C(C)=O]

n is 0 or 1; Re is either absent or where present is chlorine, fluorine, methoxy, —CN or —NO$_2$;

and conjugates may have the corresponding structure resulting from reaction of the protein or peptide bonding portion of the linker with the protein or peptide.

In some embodiments, the conjugating reagent may be represented schematically by the formula:

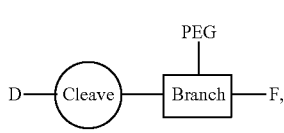

and/or the conjugate may be represented schematically by the formula

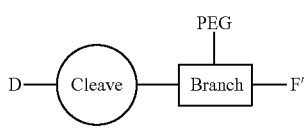

in which D represents the payload of the present invention, for example a group of formula:

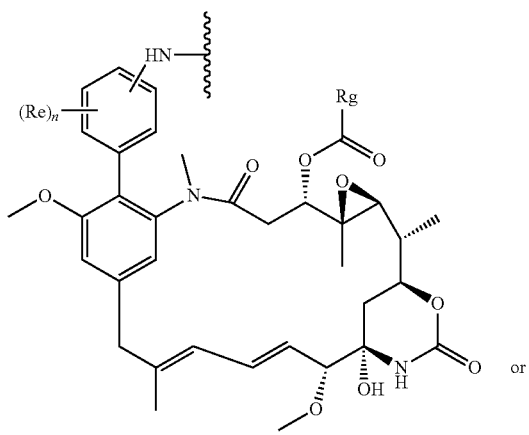

or

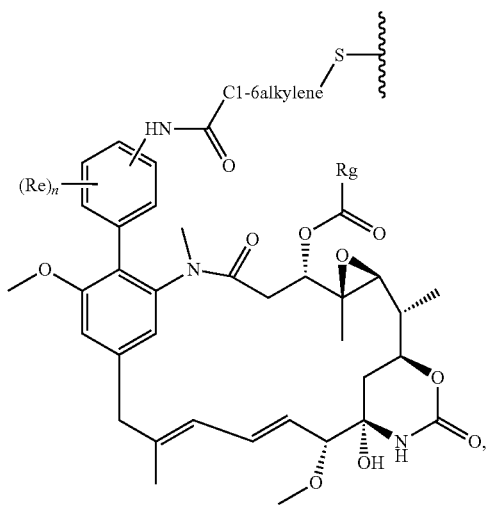

in which Rg is —C(CH$_3$)$_2$ or

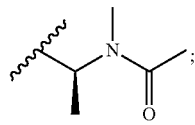 [SMILES: *[C@H](C)N(C)C(C)=O]

n is 0 or 1; Re is either absent or where present is chlorine, fluorine, methoxy, —CN or NO$_2$;

(Cleave) represents a group including a moiety which, when present in a conjugate of the invention, facilitates degradation of the conjugate under physiological conditions, such as an -Ala-Val- or -PAB-Cit-Val- group in the case where D is conjugated via a —NH— group, or a sulfur-containing group which is covalently bound to another sulfur atom present in the conjugate (i.e. resulting in a disulfide —S—S— moiety being present in the conjugate), such as a group containing a —S—C$_{1-6}$alkylene- moiety in the case where D is conjugated via a —NH—C(O)—C$_{1-6}$alkylene-S— group;

(Branch) represents a group containing a branching moiety, such as a Glu, Asp, Lys, Ser, Thr, Cys, Arg, Tyr or similar residue;

PEG represents a pendant polyethylene glycol chain having a terminal end group of formula —CH$_2$CH$_2$OR$^r$, wherein R$^r$ represents a hydrogen atom, an alkyl group, for example a C$_{1-4}$alkyl group, especially a methyl group, or an optionally substituted aryl group, especially a phenyl group, especially an unsubstituted phenyl group;

F represents the functional grouping capable of reacting with a binding protein, such as

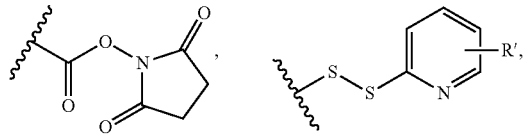

in which R' is either absent or represents an electron-withdrawing group, such as a —NO$_2$ group,
or F represents

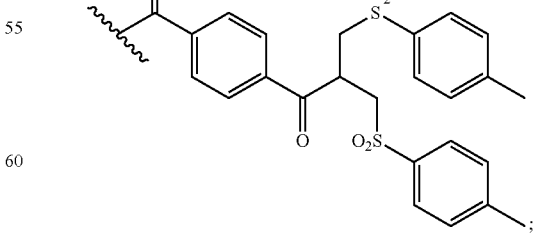

and F' represents the protein or peptide bonded to the remainder of the conjugate via the residue of the functional group.

For example, conjugating reagents of this type may have the structure:
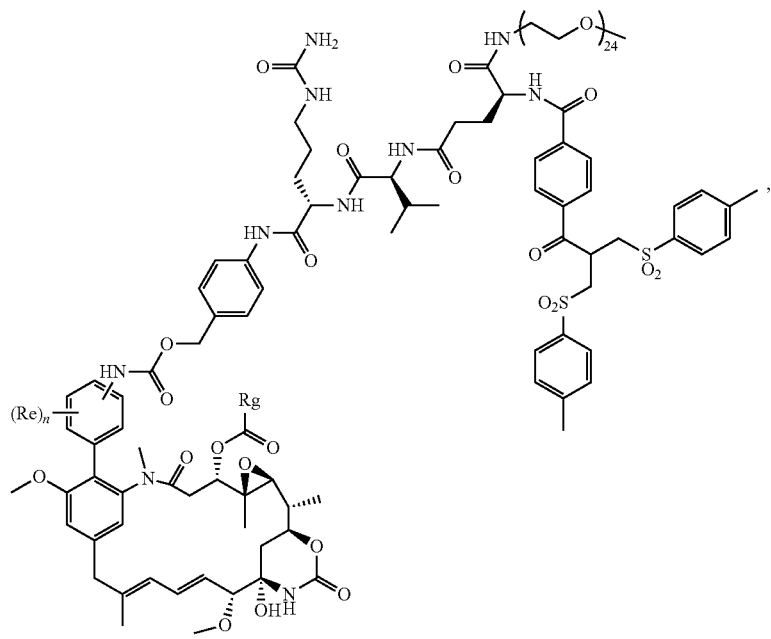
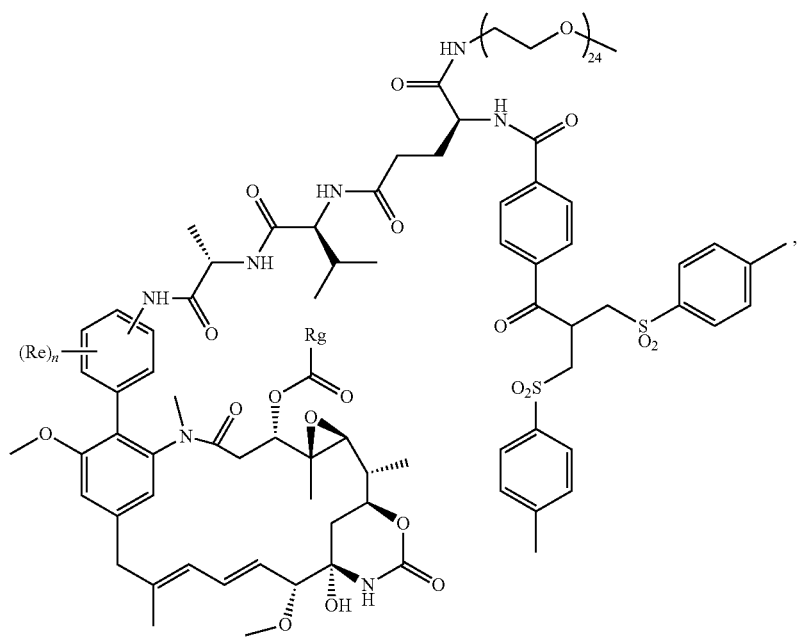

-continued
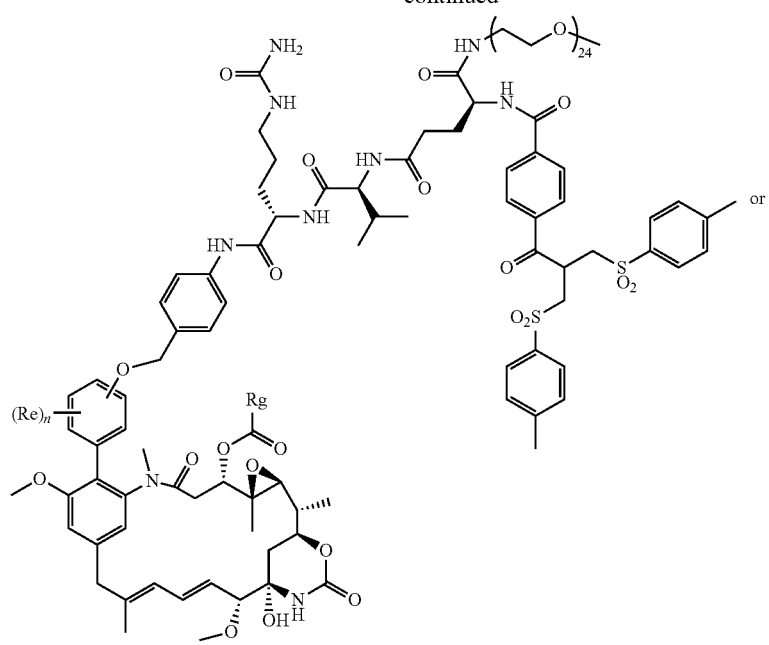
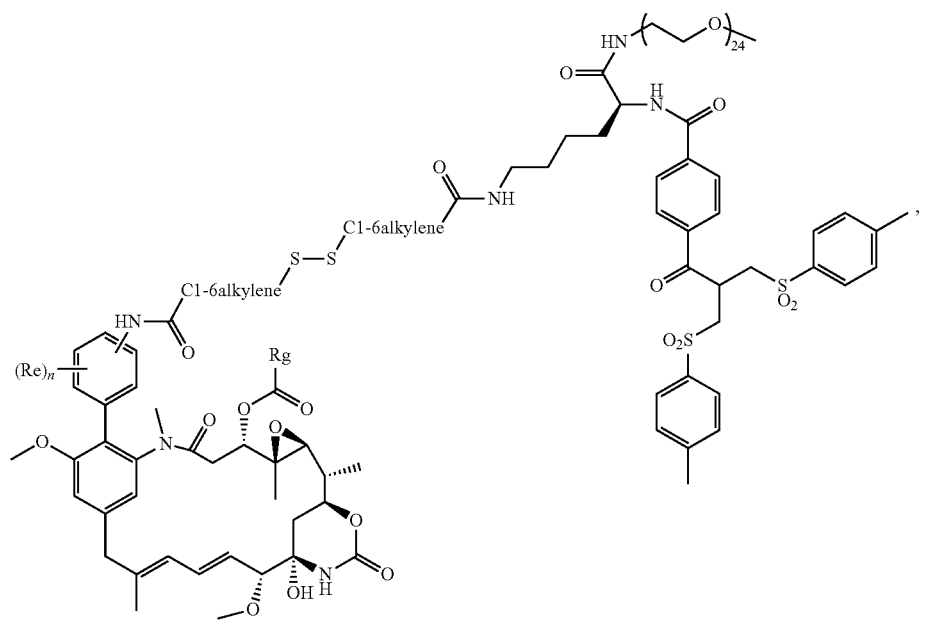

in which Rg is —C(CH$_3$)$_2$ or

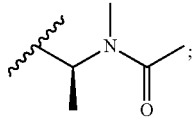 [SMILES: *[C@H](C)N(C)C(C)=O]

n is 0 or 1; Re is either absent or where present is chlorine, fluorine, methoxy, —CN or —NO$_2$;

and conjugates may have the corresponding structure resulting from reaction of the protein or peptide bonding portion of the linker with the protein or peptide.

In some embodiments, the conjugating reagent may be represented schematically by the formula

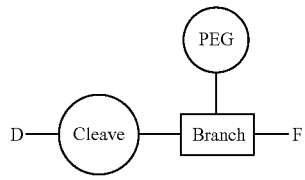

and/or the conjugate may be represented schematically by the formula

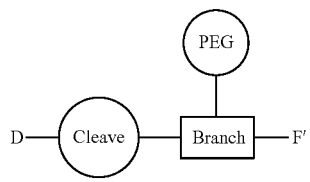

in which D represents the payload of the present invention, for example a group of formula:

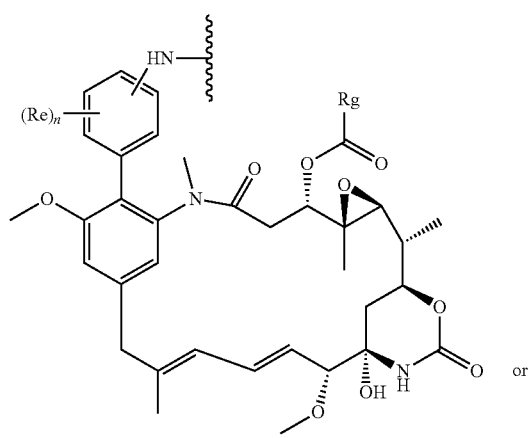

or

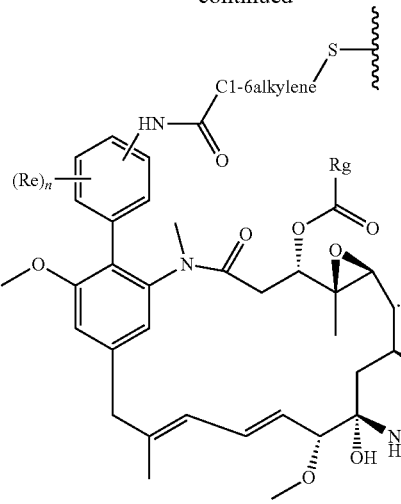

in which Rg is —C(CH$_3$)$_2$ or n is 0 or 1; Re where present is chlorine, fluorine, methoxy, —CN or —NO$_2$;

(Cleave) represents a group including a moiety which, when present in a conjugate of the invention, facilitates degradation of the conjugate under physiological conditions, such as an -Ala-Val- or -PAB-Cit-Val- group in the case where D is conjugated via a —NH— group, or a sulfur-containing group which is covalently bound to another sulfur atom present in the conjugate (i.e. resulting in a disulfide —S—S— moiety being present in the conjugate), such as a group containing a —S—C$_{1-6}$alkylene- moiety in the case where D is conjugated via a —NH—C(O)—C$_{1-6}$alkylene-S— group;

(Branch) represents a group containing a branching moiety, such as a Glu, Asp, Lys, Ser, Thr, Cys, Arg, Tyr or similar residue;

(PEG) represents a ring which includes at least two ethylene glycol, ~(CH$_2$—CH$_2$—O—)~, units;

F represents the functional grouping capable of reacting with a binding protein, such as

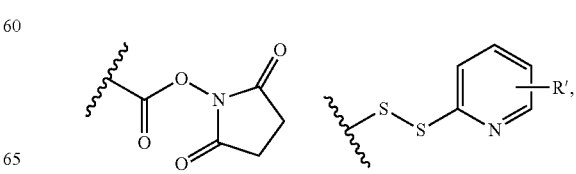

in which R' is either absent or represents an electron-withdrawing group, such as a —NO$_2$ group,
or F represents
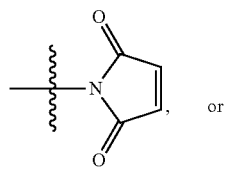, or
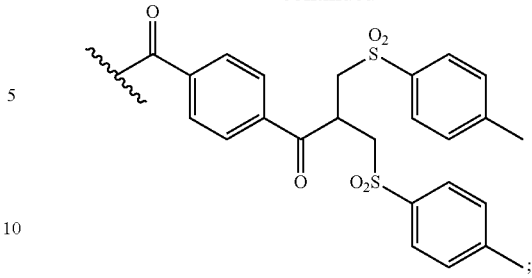
and F' represents the protein or peptide bonded to the remainder of the conjugate via the residue of the functional group.
For example, conjugating reagents of this type may have the structure:
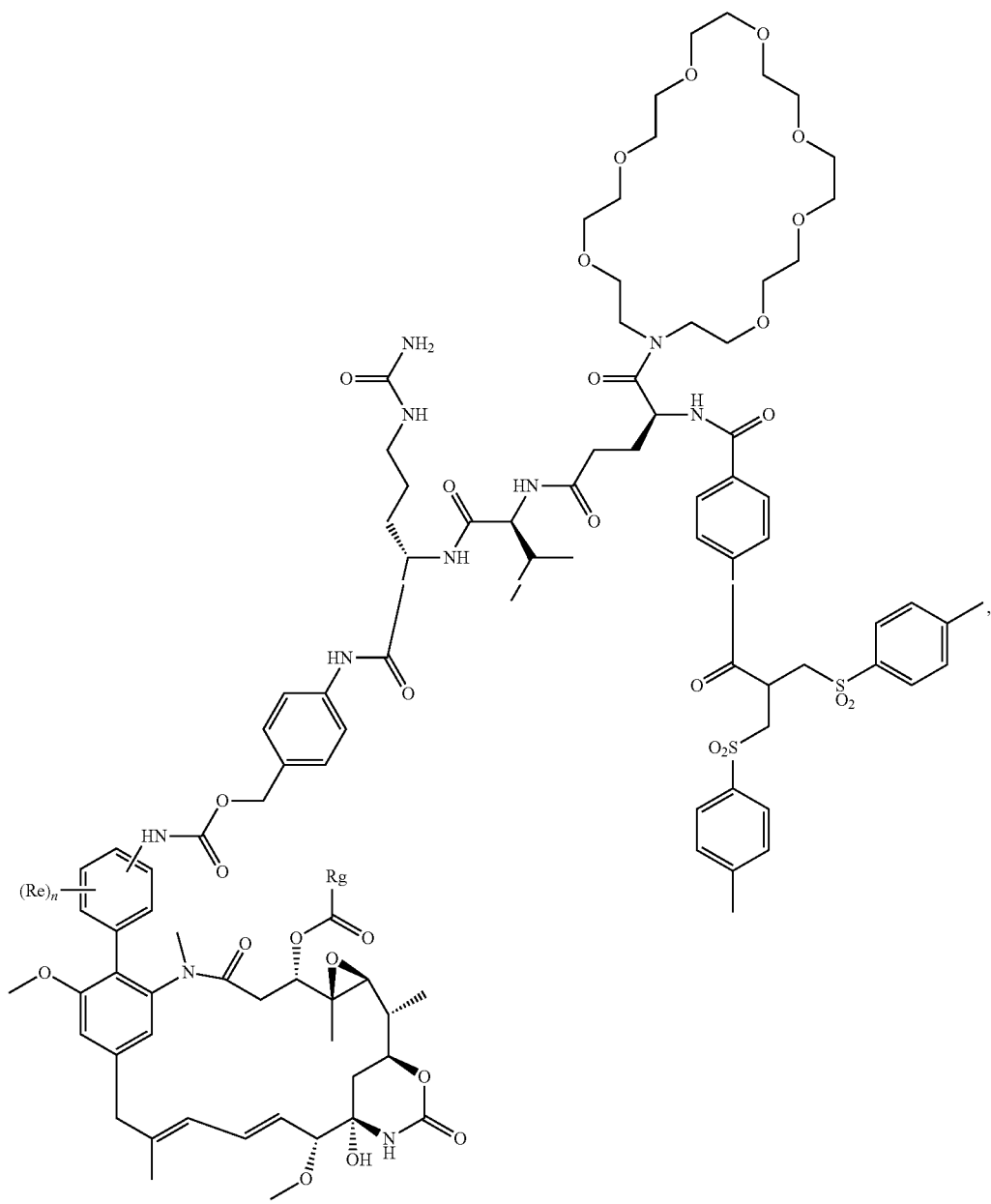

in which Rg is —C(CH₃)₂ or

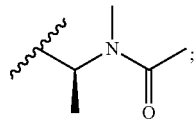 [SMILES: *[C@H](C)N(C)C(C)=O]

n is 0 or 1; Re is either absent or where present is chlorine, fluorine, methoxy, —CN or —NO₂; and conjugates may have the corresponding structure resulting from reaction of the protein or peptide bonding portion of the linker with the protein or peptide.

Compounds of the invention also include the following, which can be produced via analogous processes to those described above, e.g. via Suzuki coupling using the appropriate aryl chloride maytansinoid compound and aryl-boron reagent and, optionally, by subsequent reaction (e.g. via deprotection and/or amidation) to produce compounds of formula (I):

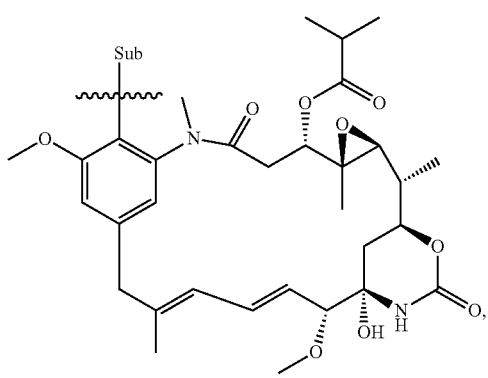

wherein Sub is

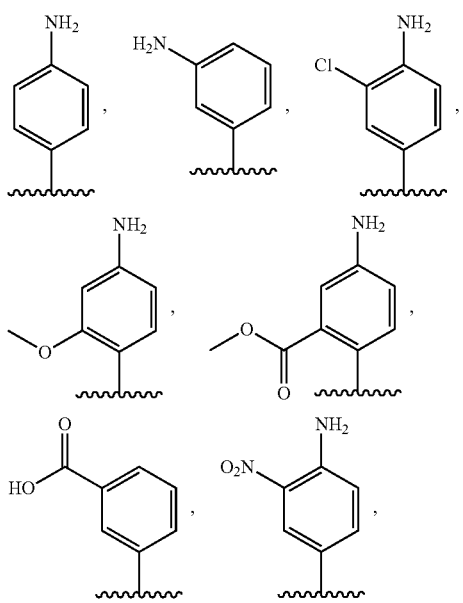

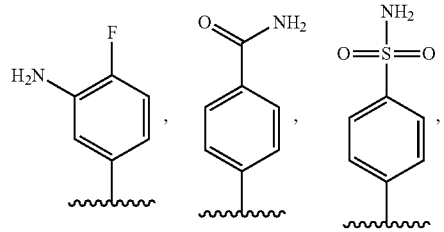

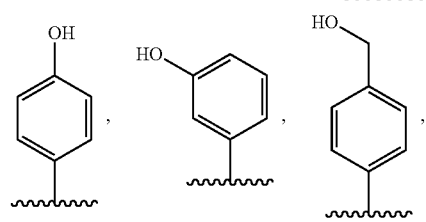

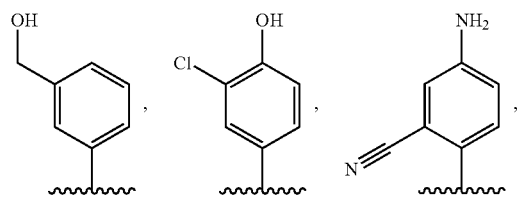

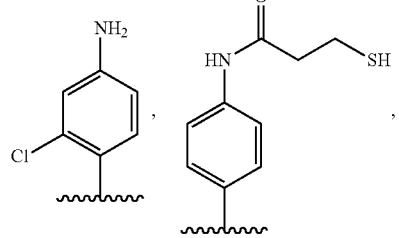

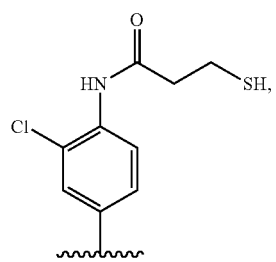

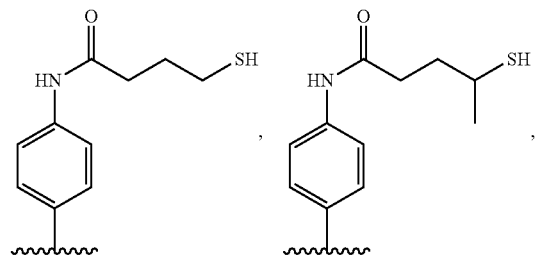

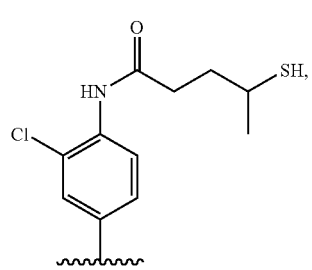

61

-continued

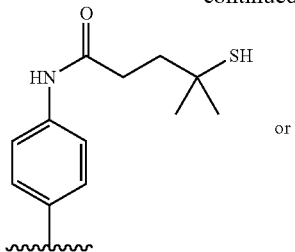

or

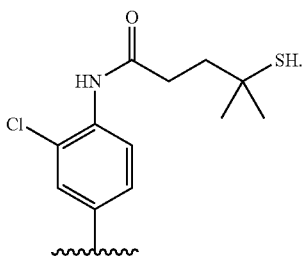

Where isolable atropisomers are produced, e.g. due to hindered rotation about the biaryl bound due to the presence of certain ortho-substituents on the phenyl ring of the Sub group, the invention also includes those individual atropisomers. For example, where Sub is

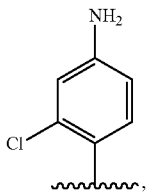 [SMILES: *c1ccc(N)cc1Cl]

the compound of the invention may be:

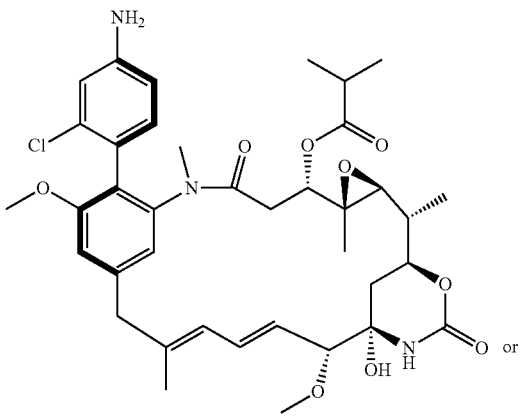

62

-continued

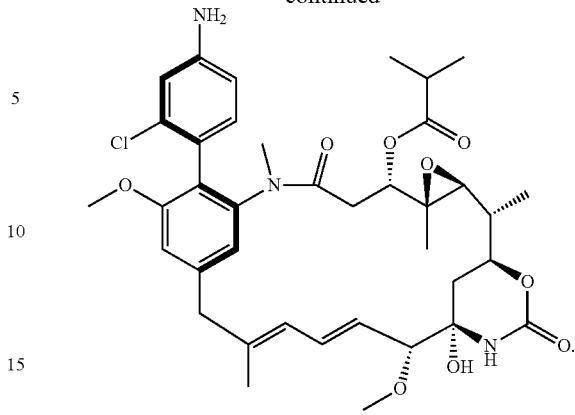

Compounds of the invention also include the example compounds described below.

Conjugates of the invention also include those incorporating the above compounds of formula (I).

Pharmaceutical Compositions and Medical Utility

The compounds and conjugates according to the invention can be formulated into a pharmaceutical composition together with a pharmaceutically acceptable carrier, optionally together with an additional therapeutic agent for use in therapy, specifically, for use as a medicament for the treatment of a proliferative, autoimmune, or infectious disease. A method of treating a patient comprises administering a pharmaceutically-effective amount of such a compound, conjugate or composition to a patient in need thereof. The patient may be an animal, specifically a mammal, and more specifically a human. Exemplary conditions for which the present invention finds utility include for example, a cancer, for example a leukemia, including non-Hodgkin's Lymphoma, acute myelogenous leukemia, multiple myeloma, lymphocytic leukemias, and chronic myelogenous leukemia; gastric cancer; breast cancer; ovarian cancer; liver cancer; intestinal cancer; colon cancer; renal cancer, for example renal cell carcinoma; lung cancer, for example small cell lung cancer; melanoma; bladder cancer; and sarcomas.

Exemplary pharmaceutical compositions include those in the form of a sterile aqueous or oleaginous suspension for parenteral administration. Parenteral administration includes subcutaneous, intravenous, intramuscular, intraperitoneal and intrathecal injection, and infusion techniques. Formulations suitable for parenteral administration (e.g., by injection), include aqueous or non-aqueous, isotonic, pyrogen-free, sterile liquids (e.g., solutions, suspensions). Such liquids may additionally contain other pharmaceutically acceptable ingredients, such as anti-oxidants, buffers, preservatives, stabilizers, bacteriostats, suspending agents, thickening agents, and solutes which render the formulation isotonic with the blood (or other relevant bodily fluid) of the intended recipient. Exemplary carriers for liquid formulations include saline, buffered saline, dextrose, water, glycerol, ethanol, or a combination thereof. The formulations may optionally further comprise pharmaceutically acceptable auxiliary substances, such as pH adjusting and buffering agents, tonicity adjusting agents, stabilizers, wetting agents and the like, or a combination thereof.

The compounds, conjugates and compositions of the present invention may if desired be used in combination with an additional therapeutic agent, for example an additional anti-cancer agent, for example, alkylating agents, alkyl sulfonates, aziridines, ethylenimines and methylamelamines, acetogenins, an auristatin, camptothecin, bryostatin, callystatin, CC-1065, cryptophycins, dolastatin, duocarmycin, eleutherobin, pancratistatin, a sarcodictyin, spongistatin, is nitrogen mustards, antibiotics, enediyne antibiotics, dynemicin, bisphosphonates, esperamicin, chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites, erlotinib, vemurafenib, crizotinib, sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid 2-ethylhydrazide, procarbazine, PSK® polysaccharide complex (JHS Natural Products, Eugene, Oreg.), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; gemcitabine; 6-thioguanine; mercaptopurine; methotrexate; platinum analogs, vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (Camptosar, CPT-11), topoisomerase inhibitor RFS 2000; difluoromethylornithine; retinoids; capecitabine; combretastatin; leucovorin; oxaliplatin; inhibitors of PKC-alpha, Raf, H-Ras, EGFR and VEGF-A that reduce cell proliferation; and pharmaceutically acceptable salts, acids or derivatives thereof; or a combination thereof.

The compounds, conjugates and compositions of the present invention may also be used in combination with an additional antibody, for example, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, ramucirumab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, 3F8 or a combination thereof.

The compounds, conjugates and compositions of the present invention may be used in treatment in combination with radiation therapy.

In some preferred embodiments, the compound, conjugate, conjugating reagent, composition, method of treatment, process or intermediate is as defined in the following numbered clauses:

1. A compound of the general formula (I) or a salt thereof:

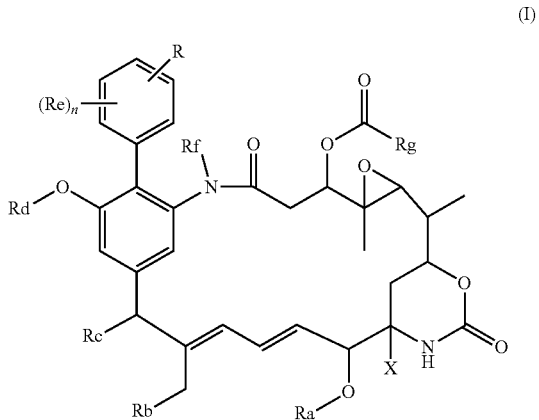

(I)

in which R represents a group —Y—OH, —Y—O—R$^x$, —Y—SH, —Y—S—R$^x$, —Y—CO$_2$H, —Y—CO—R$^x$, —Y—NHR$^y$, —Y—NR$^y$—NHR$^z$, or —Y—CR$^y$=NOH, in which either Y is not present or Y represents a C$_{1-6}$alkylene or C$_{1-6}$alkyleneoxy group either of which may be interrupted by an oxygen atom, R$^x$ represents a C$_{1-4}$alkyl group substituted by —OH, —SH, —NHR$^y$, or —CO$_2$H, and each of R$^y$ and R$^z$ independently represents a hydrogen atom or a C$_{1-4}$alkyl group; X represents OH, OC$_{1-4}$alkyl, SH, S$_{1-4}$alkyl, or CN; Ra represents a hydrogen atom or a C$_{1-4}$alkyl group; Rb represents hydrogen, OH, C$_{1-4}$alkoxy or C$_{1-4}$alkylC(O)O—; Rc represents hydrogen, OH, C$_{1-4}$alkoxy or C$_{1-4}$alkylC(O)O—; Rd represents a hydrogen atom or a C$_{1-4}$alkyl group; each Re independently represents a halogen atom, a CF$_3$ group, or a C$_{1-4}$alkyl or C$_{1-4}$alkoxy group, and n is 0, 1, 2, 3 or 4; Rf represents a hydrogen atom or a C$_{1-4}$alkyl group; and Rg represents a hydrogen atom or an optionally substituted alkyl, cycloalkyl, alkenyl, alkynyl, aryl, or heteroaryl group.

2. A compound as defined in clause 1, in which Y is not present, or in which Y represents a C$_{1-4}$alkylene or C$_{1-4}$alkyleneoxy group, which may be interrupted by an oxygen atom.

3. A compound as defined in either clause 1 or clause 2, in which R is an —OH, —NH$_2$, —CONH$_2$ or —CO$_2$H group, or a C$_{1-4}$alkylene group substituted by an —OH, —NH$_2$, —CONH$_2$ or —CO$_2$H group.

4. A compound as defined in any one of the preceding clauses, in which R is in the 3- or 4-position of the phenyl ring.

5. A compound as defined in any one of the preceding clauses, in which any Re group present is a halogen atom or a methyl or methoxy group.

6. A compound as defined in any one of the preceding clauses, in which n is 0, 1 or 2.

7. A compound as defined in any one of the preceding clauses, in which X represents OH.

8. A compound as defined in any one of the preceding clauses, in which Ra represents $C_{1-4}$alkyl; Rb represents hydrogen; Rc represents hydrogen or methoxy; Rd represents $C_{1-4}$alkyl; Re represents chlorine or hydrogen; Rf represents $C_{1-4}$alkyl; and Rg represents $C_{1-4}$alkyl.

9. A compound as defined in any one of the preceding clauses, which is a compound of the general formula (Ia) or a salt thereof:

(Ia)

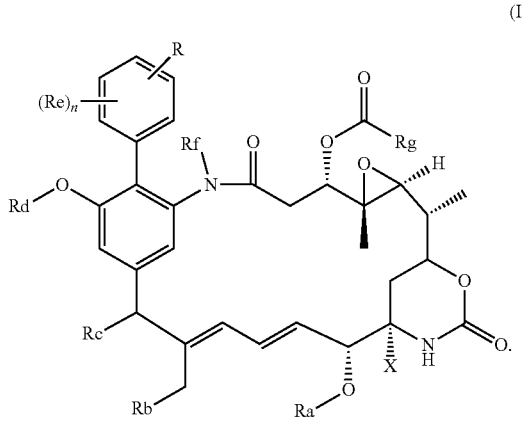

10. A compound as defined in clause 9, which is a compound of the general formula (Ib) or a salt thereof:

(Ib)

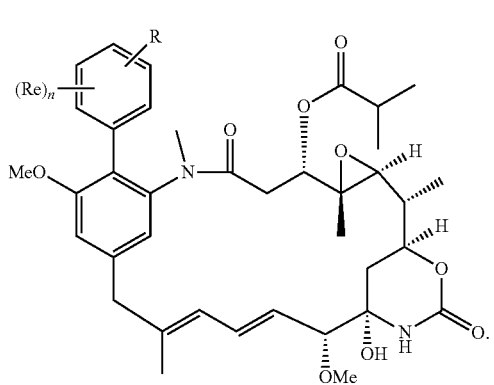

11. A conjugate comprising a compound as defined in any one of the preceding clauses linked to a binding protein via a linker, said linker being connected to said compound via the group R of the general formula I.

12. A conjugate as defined in clause 11, in which the binding protein is a full length antibody or an antibody fragment comprising an antigen-binding region of the full length antibody.

13. A conjugate as defined in clause 11, in which the binding protein is IgG1 or IgG4 or a fragment of IgG1 or IgG4.

14. A conjugate as defined in any one of clauses 11 to 13, which includes a portion:

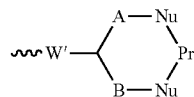

in which W' represents an electron withdrawing group or a group obtained by reduction of an electron withdrawing group, each of A and B independently represents a $C_{1-5}$alkylene or alkenylene chain, and Pr represents said binding protein bonded to A and B via nucleophiles Nu; or includes a portion:

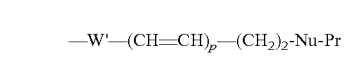

in which W' represents an electron withdrawing group or a group obtained by reduction of an electron withdrawing group, p is 0 or an integer from 1 to 4, and Pr represents said binding protein bonded to the rest of the molecule via a nucleophile Nu.

15. A conjugate as defined in clause 14, which includes a portion:

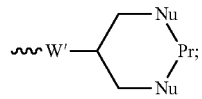

or which includes a portion:

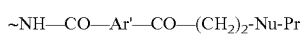

in which Ar' represents an optionally substituted aryl group.

16. A conjugate as defined in any one of clauses 11 to 15, in which each Nu represents a sulfur atom present in a cysteine residue in the binding protein Pr; or in which each Nu represents an imidazole group present in a polyhistidine tag attached to the binding protein.

17. A conjugate as defined in any one of clauses 11 to 16, in which the linker includes a pendant polyethylene glycol chain which has a terminal end group of formula —$CH_2CH_2OR^r$ in which $R^r$ represents a hydrogen atom, an alkyl group, or an optionally substituted aryl group.

18. A conjugate as defined in any one of clauses 11 to 17, in which the linker includes a peptidyl group comprising at least two naturally-occurring alpha amino acids.

19. A conjugate as defined in clause 18, in which the linker includes the sequence Val-Cit-PAB.

20. A conjugating reagent comprising a compound as defined in any one of clauses 1 to 10, attached via a linker to at least one functional group capable of reacting with a binding protein, said linker being connected to said compound via the group R of the general formula I.

21. A conjugating reagent as defined in clause 20, in which said functional group has the formula:

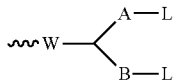

in which W represents an electron-withdrawing group; each of A and B independently represents a $C_{1-5}$alkylene or alkenylene chain; and either each L independently represents a leaving group, or both Ls together represent a leaving group; or

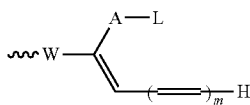

in which W and A have the meanings given above, L represents a leaving group, and m is 0 to 4; or $\sim$W—(CH=CH)$_p$—(CH$_2$)$_2$-L or $\sim$W—(CH=CH)$_p$—CH=CH$_2$ in which W represents an electron withdrawing group, p represents 0 or an integer of from 1 to 4, and L represents a leaving group.

22. A conjugating reagent as defined in clause 21, in which said functional group has the formula:

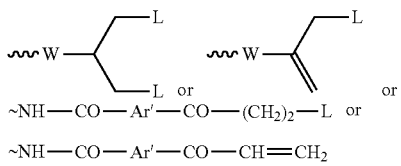

in which Ar' represents an optionally substituted aryl group.

23. A conjugating reagent as defined in any one of clauses 20 to 22, in which the or each leaving group includes a portion —(CH$_2$CH$_2$O)$_q$— in which q is a number of six or more.

24. A conjugating reagent as defined in any one of clauses 20 to 23, in which the linker includes a feature as defined in any one of clauses 17 to 19.

25. A pharmaceutical composition comprising a compound as defined in any one of clauses 1 to 10, or a conjugate as defined in any one of clauses 11 to 19, together with a pharmaceutically acceptable carrier, optionally together with an additional therapeutic agent.

26. A method of treating a patient in need of treatment for a proliferative, autoimmune, or infectious disease or disorder, comprising administering a pharmaceutically-effective amount of a compound as defined in any one of clauses 1 to 10, a conjugate as defined in any one of clauses 11 to 19, or a pharmaceutical composition as defined in clause 25, to the patient.

27. A compound as defined in any one of clauses 1 to 10 or a conjugate as defined in any one of clauses 11 to 19 for use in therapy.

28. A process for the preparation of a compound of the general formula I or a salt thereof as defined in any one of clauses 1 to 10, which comprises reacting a compound of the general formula:

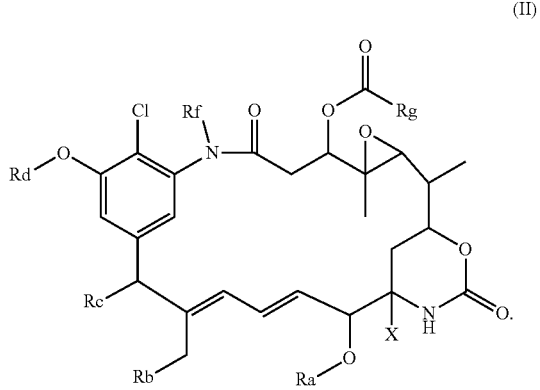

(II)

in which X, Ra-Rd, Rf and Rg have the meanings given for the general formula I, with an aryl-organometallic reagent in which the aryl moiety is a phenyl group substituted by (Re)$_n$ and by R or a protected version of R, in which R and (Re)$_n$ have the meanings given for the general formula I, the reaction being carried out in the presence of a transition metal catalyst.

29. A process as defined in clause 28, in which the aryl-organometallic reagent is a boronic acid of the general formula

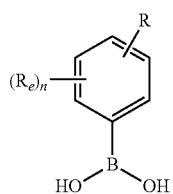

(III)

or a protected version thereof and the reaction is carried out in the presence of a palladium catalyst.

30. An intermediate useful for preparing a compound of the general formula I or a salt thereof as defined in any one of clauses 1 to 10, which has the general formula

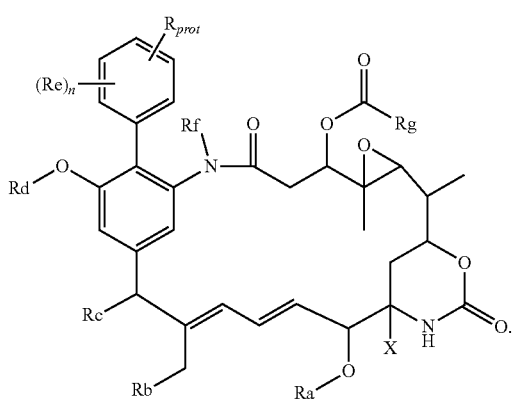

in which X, n and Ra-Rg have the meanings given for the general formula I and $R_{prot}$ is the group R of the general formula I carrying a protecting group; or a salt thereof.

31. An intermediate as defined in clause 30, in which R includes an —OH or —SH group and the protecting group is a silyl group, an acyl group, or an arylmethyl group; R includes a —CO$_2$H group and the protecting group is methyl, ethyl, t-butyl, benzyl, p-methoxybenzyl, 9-fluorenylmethyl, trimethylsilyl, t-butyldimethylsilyl, or diphenylmethyl; or R includes an —NHR', —NHR" or —NHR'" group and the protecting group is t-butoxycarbonyl, trityl, benzyloxycarbonyl, 9-fluorenylmethoxycarbonyl, formyl, trimethylsilyl, or t-butyldimethylsilyl.

EXAMPLES

Figure 1:
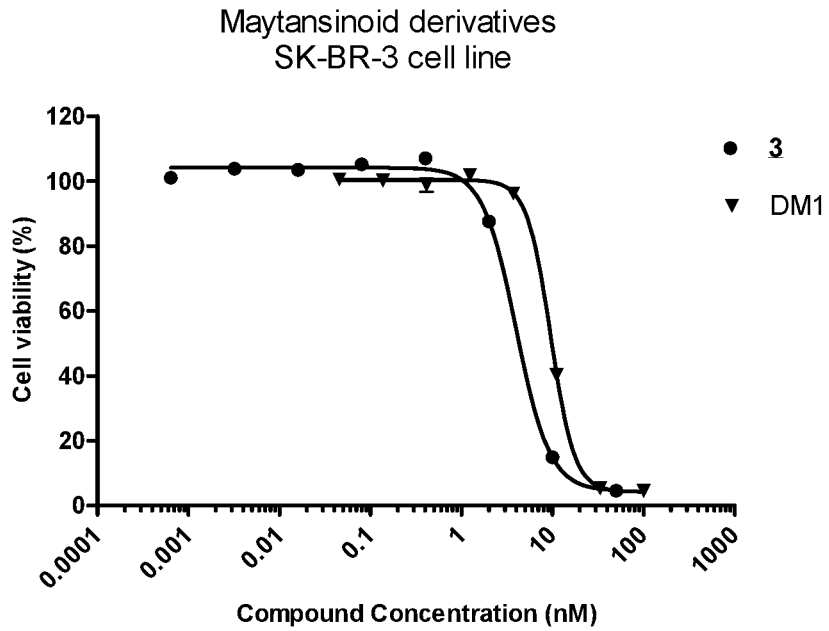
FIGS. 1 and 2 show the results of Example 2, showing plots of % cell viability versus compound concentration for compound 3 and for DM1 in in vitro assays against the CD30-positive human T cell lymphoma cell line Karpas-299 and the HER2-positive tumour cell line SK-BR-3.

The following Examples illustrate the invention.
General Methods:

$^1$H NMR spectra were recorded using an appropriate NMR instrument (e.g. a Varian Inova 500 MHz NMR instrument). Chromatographic purities were determined using LC/MS (e.g. on an Agilent 1200 Series LC/MS system).

Example 1: Preparation of 4-(N-Boc amino)phenyl-AP3, 3

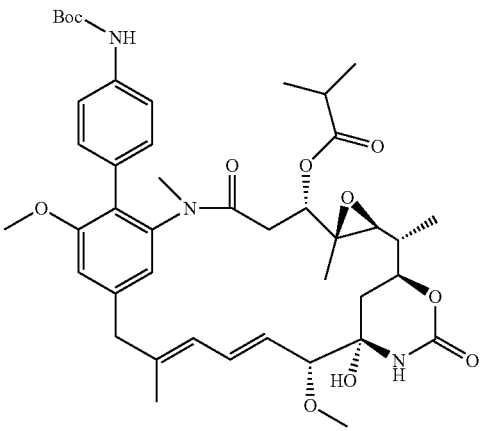

Compound 1 4-(N-Boc amino)phenyl boronic acid (18.7 mg), was added to solid AP3 2 (32.6 mg), with potassium phosphate tribasic (32.7 mg) and the palladium catalyst Sphos Pd G3 (1 mg) commercially available from Sigma-Aldrich. The solids were purged with Ar 3× and dry THF (150 μL) added to the mixture. Ar was then bubbled through the reaction mixture for 60 sec, the reaction vessel was sealed and heated at 40° C. for 2 h, at which point the reaction was deemed complete by LC/MS. The reaction mixture was then filtered through a short pad of SiO$_2$, washed with Et$_2$O and concentrated. The mixture was then purified by preparative HPLC (Gemini 150×30 mm column) (5→95% ACN in H$_2$O, each containing 0.05% AcOH) and desired fractions lyophilized to afford 3 as a white crystalline solid (14.3 mg, 35% yield). $^1$H NMR (500 MHz, CHLOROFORM-d) δ=7.41 (d, J=7.3 Hz, 2H), 7.06 (d, J=8.8 Hz, 2H), 6.88 (dd, J=1.5, 10.7 Hz, 2H), 6.58-6.46 (m, 2H), 6.27-6.18 (m, 2H), 5.49 (dd, J=9.0, 15.4 Hz, 1H), 4.85 (dd, J=2.9, 12.2 Hz, 1H), 4.36-4.28 (m, 1H), 3.83 (s, 3H), 3.61-3.52 (m, 2H), 3.39 (s, 3H), 3.28 (d, J=13.2 Hz, 1H), 3.09-2.95 (m, 3H), 2.70-2.68 (m, 3H), 2.65 (quin, J=7.0 Hz, 1H), 2.25 (dd, J=2.9, 13.7 Hz, 1H), 1.77 (s, 3H), 1.70 (d, J=13.2 Hz, 1H), 1.55 (s, 9H), 1.33 (d, J=6.3 Hz, 3H), 1.28 (d, J=7.3 Hz, 3H), 1.22 (d, J=6.8 Hz, 3H), 0.96 (s, 3H); LC/MS: retention time 3.49 min (Merck Chromolith RP-18e analytical HPLC column (monolithic, 50×2 mm); analytical HPLC method: injection volume 5 μL; flow rate 1 mL/min; 5→95% acetonitrile in water over 5 mins; Agilent diode array detector at λ=254, or 220 nm; room temperature), (ES$^+$) calc for C$_{43}$H$_{58}$N$_3$O$_{11}$: [M+H]$^+$ 792; found 792.

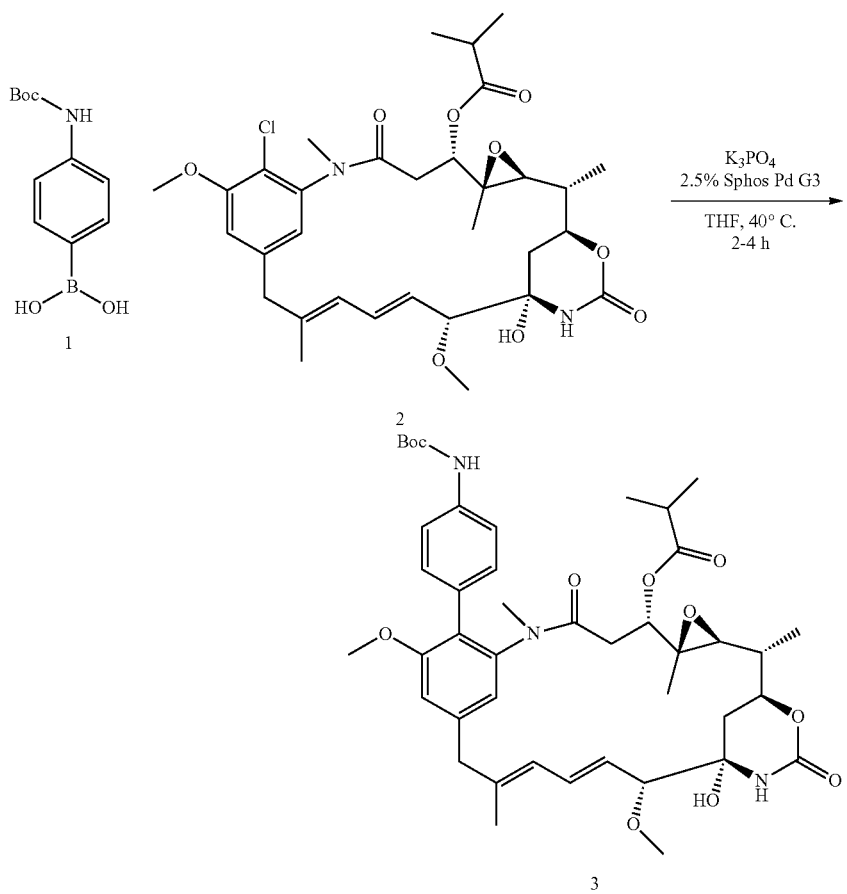

The BOC protecting group may be removed from compound 3 to produce the corresponding compound containing a free amine group. This compound may then, in turn, be conjugated via the amine group using known methods to produce a conjugate, specifically, and antibody-drug conjugate.

Example 2: In Vitro Potency Assay of Compound 3 in Karpas-299 and SK-BR-3 Cell Lines Loss of tumour cell viability following treatment with cytotoxic drugs or ADCs in vitro can be measured by growing cell lines in the presence of increasing concentrations of drugs or ADCs and quantifying the loss of proliferation or metabolic activity using CellTiter-Glo® Luminescence reagent (Promega). The protocol describes cell seeding, drug treatment and determination of the cell viability in reference to untreated cells based on ATP synthesis, which is directly related to the number of cells present in the well.

The CD30-positive human T cell lymphoma cell line Karpas-299 was obtained from Dr Abraham Karpas at the University of Cambridge. The cells were grown in RPMI medium supplemented with 10% foetal bovine serum, 100 U/mL Penicillin and 100 μg/mL Streptomycin. Karpas 299 cells were seeded at 2,500 cells per well (50 μL/well) into clear bottom white-walled 96-well plates and incubated for 24 h at 37° C. and 5% $CO_2$.

HER2-positive tumour cell line, SK-BR-3 (ATCC-HTB-30), was grown in McCoy's 5A medium complemented with 10% foetal bovine serum, 100 u/mL Penicillin and 100 μg/mL Streptomycin. SK-BR-3 cells were detached, seeded at 5,000 cells per well (100 μL/well) into poly-D-lysine coated clear bottom white-walled 96-well plates and incubated for 24 h at 37° C. and 5% $CO_2$.

Serial dilutions of compounds were prepared in triplicate using the relevant cell culture medium as diluent. The CD30-positive Karpas-299 cells were treated with 50 μL compounds at 2× assay concentration. Medium from the SK-BR-3 assay plates was removed and replaced by 100 μL serially diluted compounds at 1× assay concentration. The assay concentrations are specified in Table 1. The cells were then incubated with the compounds (total volume 100 μL/well), at 37° C. and 5% $CO_2$ for a further 96 h.

TABLE 1

| Cell line | Compound | Concentration range |
| --- | --- | --- |
| Karpas-299 | 3 | 200 nM-20 fM |
| SK-BR-3 | 3 | 50 nM-640 fM |

At the end of the incubation, cell viability was measured using the CellTiter-Glo® Luminescence reagent, as described by the manufacturer's instructions. The data was subsequently analysed using a four parameter non-linear regression model.

Viability was expressed as % of untreated cells and calculated using the following formula:

$$\% \text{ Viability} = 100 \times \frac{\text{Luminescence}_{Sample} - \text{Luminescence}_{No\ cell\ Control}}{\text{Luminescence}_{Untreated} - \text{Luminescence}_{No\ cell\ Control}}$$

The % viability (Y-axis) was plotted against the logarithm of drug concentration in nM (X-axis) to extrapolate the $IC_{50}$ values for all compounds.

Figure 2:
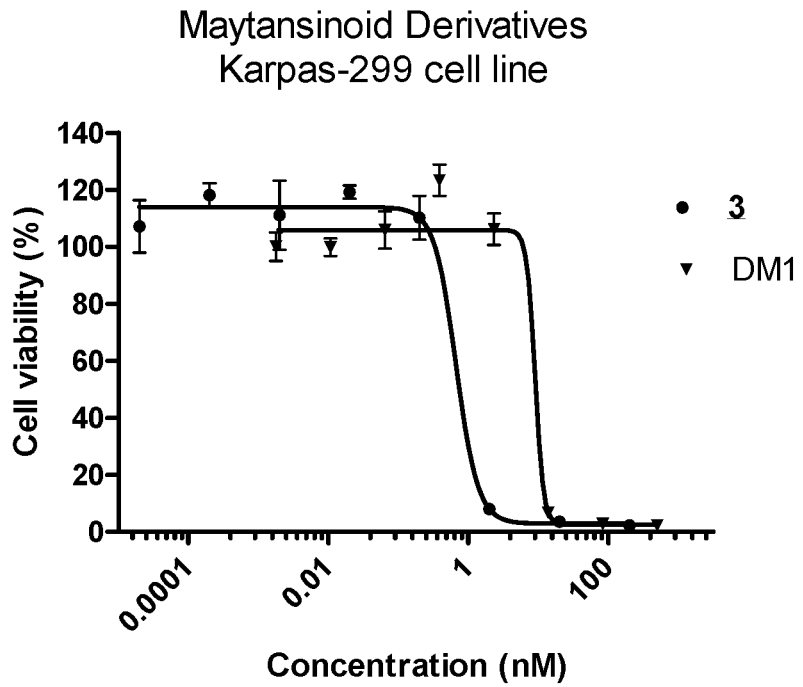

Results are shown in Table 2 and FIGS. 1 and 2. In both cell lines compound 3 has higher potency than the control DM1.

TABLE 2

| Compound number/name | IC50 (nM) SKBR3 Cell line | IC50 (nM) Karpas-299 Cell line |
| --- | --- | --- |
| 3 | 4 | 0.7 |
| DM1 | 10 | 9 |

Example 3: Preparation of Maytansinoid Compound 4

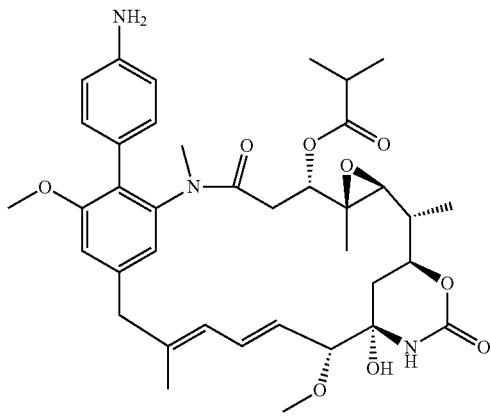

The aryl boron reagent, 4-aminophenylboronic acid (215 mg), tripotassium phosphate (668 mg), the catalyst SPhos Pd G3 (15.4 mg) and AP3 (500 mg) were sequentially added to an argon purged reaction vessel. The vessel was then sealed and the solids purged with argon (4×evacuation/purge cycles). THF (6 mL) and water (0.6 mL), which had been rigorously deoxygenated by purging with argon, were then added and the reaction mixture was stirred at room temperature for 18 h. The reaction mixture was then diluted with ethyl acetate (60 mL) and washed with brine (20 mL). The layers were separated and the organic layer was concentrated under reduced pressure. The residue was then purified by reverse phase C-18 column chromatography eluting with buffer A (v/v): water:0.1% acetic acid and buffer B (v/v): acetonitrile:0.1% acetic acid (100:0 v/v to 0:100 v/v) and the desired fractions lyophilised to give compound 4 as a white solid (449 mg). ¹H NMR (500 MHz; CDCl₃) δ 6.90 (d, J=8.1 Hz, 2H), 6.84 (d, J=10.1 Hz, 2H), 6.69 (d, J=8.6 Hz, 2H), 6.48 (dd, J=15.4, 11.0 Hz, 1H), 6.24 (s, 1H), 6.18 (d, J=11.0 Hz, 1H), 5.49-5.44 (m, 1H), 4.84 (dd, J=11.9, 2.8 Hz, 1H), 4.32-4.27 (m, 1H), 3.82 (s, 3H), 3.55 (d, J=13.0 Hz, 1H), 3.52 (d, J=9.0 Hz, 1H), 3.37 (s, 3H), 3.25 (d, J=13.0 Hz, 1H), 3.06 (s, 1H), 3.00 (d, J=9.9 Hz, 1H), 2.97-2.94 (m, 1H), 2.68 (s, 3H), 2.64-2.61 (m, 1H), 2.23 (dd, J=13.8, 2.7 Hz, 1H), 1.74 (s, 3H), 1.68 (d, J=13.6 Hz, 1H), 1.52-1.47 (m, 1H), 1.30 (d, J=6.5 Hz, 3H), 1.26 (d, J=7.2 Hz, 3H), 1.25-1.23 (m, 1H), 1.20 (d, J=6.5 Hz, 3H), 0.93 (s, 3H). LC/MS: (ES+) [M+H]⁺ (692, 100%).

Example 4: Preparation of Maytansinoid Compound 5

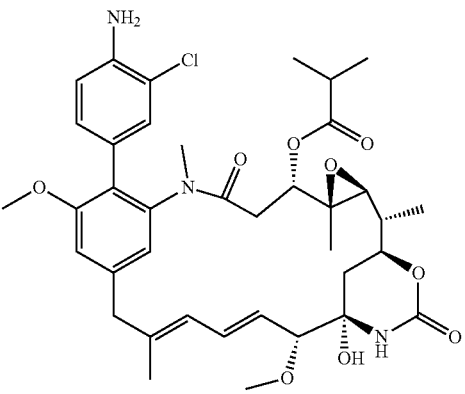

Compound 5 was synthesised in an analogous way to compound 4 of Example 3. Briefly, 4-amino-3-chlorophenylboronic acid pinacol ester (100 mg), tripotassium phosphate (674 mg), SPhos Pd G3 (15.2 mg) and AP3 (500 mg) were sequentially added to an argon purged reaction vessel. The vessel was then sealed and the solids purged with argon (4× evacuation/purge cycles). THF (6 mL) and water (0.6 mL), which had been rigorously deoxygenated by purging with argon, were then added and the reaction mixture was stirred at room temperature for 5 h. The reaction mixture was then diluted with ethyl acetate (60 mL) and washed with brine (20 mL). The layers were separated and the organic layer was concentrated under reduced pressure. The residue was then purified by reverse phase C-18 column chromatography eluting with buffer A (v/v): water:0.1% acetic acid and buffer B (v/v): acetonitrile:0.1% acetic acid (100:0 v/v to 0:100 v/v) and the desired fractions lyophilised to give compound 5 as a white solid (80 mg). NMR (500 MHz; CDCl₃) δ 7.05 (s, 1H), 6.85 (d, J=11.4 Hz, 2H), 6.77 (s, 2H), 6.48 (dd, J=15.4, 11.2 Hz, 1H), 6.24 (s, 1H), 6.18 (d, J=11.2 Hz, 1H), 5.46 (dd, J=15.4, 9.0 Hz, 1H), 4.84 (dd, J=11.8, 2.8 Hz, 1H), 4.32-4.27 (m, 1H), 4.11 (d, J=0.6 Hz, 2H), 3.83 (s, 3H), 3.55 (d, J=13.0 Hz, 1H), 3.52 (d, J=9.0 Hz, 1H), 3.37 (s, 3H), 3.25 (d, J=13.0 Hz, 1H), 3.02-2.99 (m, J=7.8 Hz, 2H), 2.93 (dd, J=13.7, 12.2 Hz, 1H), 2.72 (s, 3H), 2.65-2.60 (m, 1H), 2.24-2.21 (m, 1H), 1.74 (s, 3H), 1.68 (d, J=13.3 Hz, 1H), 1.53-1.47 (m, 1H), 1.30 (d, J=6.4 Hz, 3H), 1.30-1.27 (m, 1H), 1.26 (d, J=7.2 Hz, 3H), 1.20 (d, J=6.7 Hz, 3H), 0.93 (s, 3H). LC/MS: (ES+) [M+H]⁺ (726, 100%).

Example 5: Preparation of Maytansinoid Compound 6

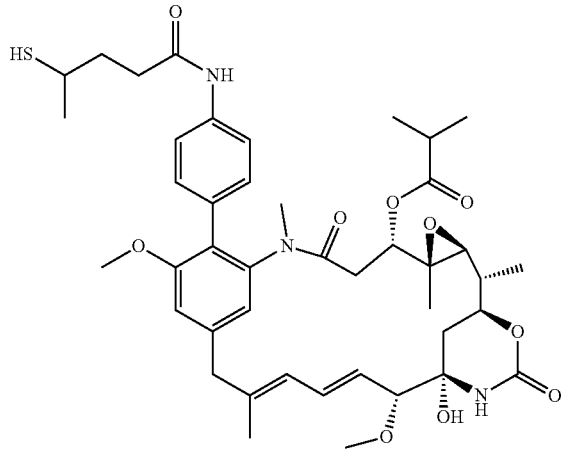

6

Step 1: Synthesis of Compound 7.

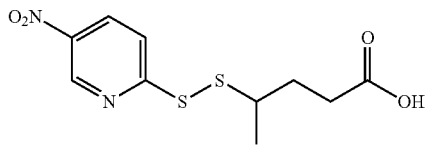

7

To a solution of 2,2'-dithiobis(5-nitropyridine) (930 mg) and 4-mercapto-pentanoic acid (197 mg) in THF:DMF (8 mL, 1:1 v/v) was added pyridine (150 µL) and the solution was stirred at room temperature for 15 h. The reaction mixture was then diluted with ethyl acetate (50 mL) and washed with brine (20 mL). The organic layer was separated, dried over sodium sulfate, filtered and concentrated in vacuo. The residue was then purified by normal phase chromatography eluting with hexane:ethyl acetate (100:0 v/v to 60:40 v/v). The solvent was removed in vacuo to give compound 7 as a pale yellow solid (194 mg). $^1$H NMR (500 MHz; CDCl$_3$) δ 9.26 (d, J=2.1 Hz, 1H), 8.39 (dd, J=8.8, 2.1 Hz, 1H), 7.89 (d, J=8.8 Hz, 1H), 3.13-3.06 (m, 1H), 2.64-2.53 (m, 2H), 2.04-1.89 (m, 2H), 1.37 (d, J=6.8 Hz, 3H). LC/MS: (ES+) [M+H]$^+$ (289, 100%).

Step 2: Synthesis of Compound 8.

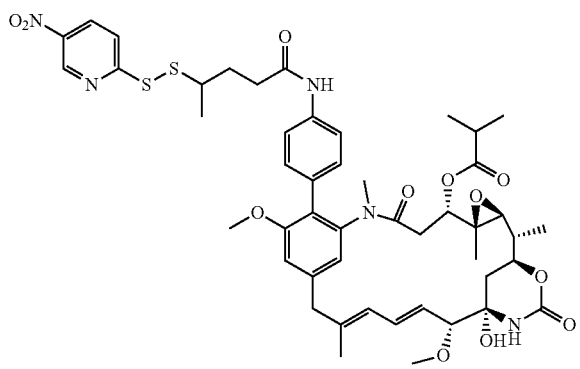

8

To a stirred solution of compound 4 (237 mg), compound 7 (102 mg) and HATU (405 mg) in DMF (8 mL) at 0° C. was slowly added N,N-diisopropylethylamine (DIPEA, 240 µL). The reaction mixture was allowed to warm to room temperature and was stirred for 16 h. The solution was diluted with water (20 mL) and brine (20 mL) and the resulting mixture was extracted with ethyl acetate (50 mL). The organic layer was separated and concentrated in vacuo. The residue was dissolved in DMF (8 mL) and purified by reverse phase C-18 column chromatography eluting with buffer A (v/v): water:0.1% acetic acid and buffer B (v/v): acetonitrile:0.1% acetic acid (100:0 v/v to 0:100 v/v). The desired fractions were lyophilised to give compound 8 as a pale yellow solid (253 mg). $^1$H NMR (500 MHz; CDCl$_3$) δ 9.27 (d, J=2.2 Hz, 1H), 8.40 (dt, J=8.8, 2.9 Hz, 1H), 7.95-7.93 (m, 1H), 7.56-7.54 (m, 2H), 7.47-7.45 (m, 1H), 7.10 (dd, J=7.6, 0.4 Hz, 2H), 6.89 (d, J=7.7 Hz, 2H), 6.54-6.48 (m, 1H), 6.24 (d, J=0.4 Hz, 1H), 6.21 (d, J=11.1 Hz, 1H), 5.49 (dd, J=15.2, 9.1 Hz, 1H), 4.85 (dd, J=12.0, 2.8 Hz, 1H), 4.34-4.29 (m, 1H), 3.84 (s, 3H), 3.59 (d, J=13.0 Hz, 1H), 3.54 (d, J=9.0 Hz, 1H), 3.39 (s, 3H), 3.29 (d, J=12.9 Hz, 1H), 3.22-3.17 (m, 1H), 3.04-2.97 (m, 3H), 2.69 (d, J=2.8 Hz, 3H), 2.67-2.56 (m, 3H), 2.27-2.24 (m, 1H), 2.12-2.07 (m, 2H), 1.77 (s, 3H), 1.70 (d, J=13.0 Hz, 1H), 1.55-1.48 (m, 1H), 1.42-1.41 (m, 3H), 1.32 (d, J=6.4 Hz, 3H), 1.27-1.26 (m, 1H), 1.28 (d, J=7.2 Hz, 3H), 1.22 (d, J=6.7 Hz, 3H), 0.96 (s, 3H). LC/MS: (ES+) [M+H]$^+$ (962, 100%).

Step 3: Synthesis of Compound 6.

To a solution of compound 8 (22 mg) and tris(2-carboxyethyl)phosphine hydrochloride (TCEP.HCl, 67 mg) in acetonitrile:water (1.8 mL, 5:4 v/v) was slowly added saturated sodium hydrogen carbonate solution (1.2 mL) until a pH of 7-8 was achieved. The reaction mixture was then stirred at room temperature for 2 h before the solution was concentrated in vacuo and the residue dissolved in acetonitrile (50 mL). The acetonitrile solution was then washed with brine (20 mL), the layers were separated and the organic layer was concentrated in vacuo. The residue was then purified by reverse phase C-18 column chromatography eluting with buffer A (v/v): water:0.1% acetic acid and buffer B (v/v): acetonitrile:0.1% acetic acid (100:0 v/v to 0:100 v/v) and the desired fractions lyophilised to give compound 6 as a white solid (14 mg). $^1$H NMR (500 MHz; CDCl$_3$) δ 7.58-7.57 (m, 1H), 7.51-7.47 (m, 1H), 7.09 (d, J=8.2 Hz, 2H), 6.89 (d, J=9.0 Hz, 2H), 6.51 (dd, J=15.4, 11.1 Hz, 1H), 6.24 (s, 1H), 6.22-6.20 (m, 1H), 5.49 (dd, J=15.3, 9.0 Hz, 1H), 4.85 (dd, J=12.0, 2.8 Hz, 1H), 4.34-4.29 (m, 1H), 3.83 (s, 3H), 3.58 (d, J=12.9 Hz, 1H), 3.54 (d, J=8.9 Hz, 1H), 3.39 (s, 3H), 3.28 (d, J=12.8 Hz, 1H), 3.07-2.96 (m, 4H), 2.69 (s, 3H), 2.66-2.62 (m, 1H), 2.61-2.53 (m, 2H), 2.27-2.24 (m, 1H), 2.19-2.13 (m, 1H), 1.86-1.80 (m, 1H), 1.77 (s, 3H), 1.70 (d, J=13.5 Hz, 1H), 1.54-1.48 (m, 2H), 1.43 (d, J=6.7 Hz, 3H), 1.32 (d, J=6.3 Hz, 3H), 1.28 (d, J=7.2 Hz, 3H), 1.27-1.26 (m, 1H), 1.22 (d, J=6.7 Hz, 3H), 0.96 (s, 3H). LC/MS: (ES+) [M+H]$^+$ (808, 100%).

Example 6: Preparation of Maytansinoid Compound 9

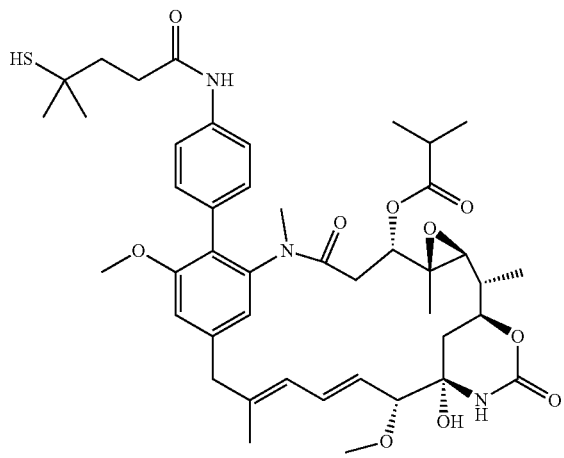

9

Step 1: Synthesis of Compound 10.

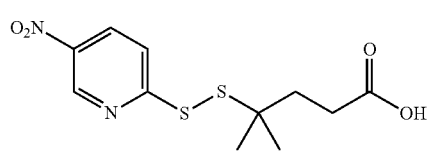

10

Compound 10 was synthesised in an analogous way to compound 7 of Example 5 using 4-mercapto-4-methyl-pentanoic acid instead of 4-mercapto-pentanoic acid. Compound 10 was isolated as a pale yellow solid. LC/MS: (ES+) [M+H]$^+$ (303, 100%).

Step 2: Synthesis of Compound 11.

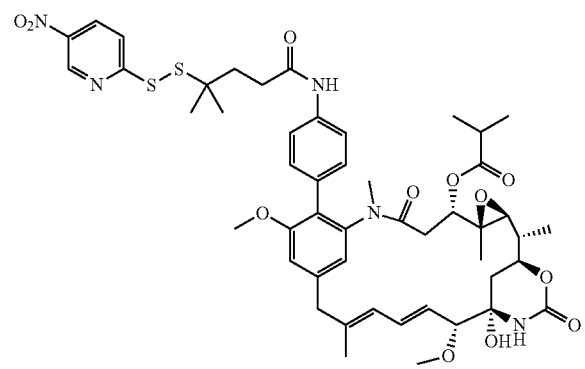

11

Compound 11 was synthesised in an analogous way to compound 8 of Example 5 using compound 10 instead of compound 7. Compound 11 was isolated as a pale yellow solid. $^1$H NMR (500 MHz; CDCl$_3$) δ 9.35-9.24 (m, 1H), 8.44-8.36 (m, 1H), 7.88 (dd, J=46.8, 8.7 Hz, 1H), 7.54-7.44 (m, 2H), 7.35-7.34 (m, 1H), 7.09-7.07 (m, 1H), 6.87-6.86 (m, 2H), 6.51-6.46 (m, 1H), 6.26 (s, 1H), 6.20-6.17 (m, 1H), 5.47 (dd, J=15.6, 9.1 Hz, 1H), 4.85-4.82 (m, 1H), 4.32-4.27 (m, 1H), 3.82 (s, 3H), 3.58-3.55 (m, 1H), 3.52 (d, J=8.9 Hz, 1H), 3.37 (s, 3H), 3.28-3.25 (m, 1H), 3.16-3.12 (m, 1H), 3.03-2.94 (m, 3H), 2.67 (s, 3H), 2.66-2.60 (m, 1H), 2.56-2.53 (m, 2H), 2.25-2.22 (m, 1H), 2.15-2.07 (m, 2H), 1.75 (s, 3H), 1.69-1.66 (m, 1H), 1.52-1.48 (m, 1H), 1.37 (s, 6H), 1.30 (d, J=6.3 Hz, 3H), 1.26 (d, J=7.1 Hz, 3H), 1.25-1.24 (m, 1H), 1.20 (d, J=6.7 Hz, 3H), 0.94 (s, 3H). LC/MS: (ES+) [M+H]$^+$ (976, 100%).

Step 3: Synthesis of Compound 9.

Compound 9 was synthesised in an analogous way to compound 6 of Example 5 using compound 11 instead of compound 8. Compound 9 was isolated as a white solid. $^1$H NMR (500 MHz; CDCl$_3$) $^1$H NMR (500 MHz; CDCl$_3$) δ 7.56-7.54 (m, 2H), 7.34 (s, 1H), 7.08-7.07 (m, 2H), 6.86 (d, J=9.8 Hz, 2H), 6.51-6.46 (m, 1H), 6.21-6.18 (m, 2H), 5.49-5.44 (m, 1H), 4.85-4.82 (m, 1H), 4.32-4.27 (m, 1H), 3.81 (s, 3H), 3.56 (d, J=12.7 Hz, 1H), 3.52 (d, J=9.0 Hz, 1H), 3.37 (s, 3H), 3.26 (d, J=13.6 Hz, 1H), 3.01-2.94 (m, 3H), 2.67 (s, 3H), 2.64-2.61 (m, 1H), 2.59-2.56 (m, 2H), 2.25-2.22 (m, 1H), 2.04-2.01 (m, 2H), 1.75 (s, 3H), 1.69-1.67 (m, 1H), 1.52-1.48 (m, 1H), 1.43 (s, 6H), 1.30 (d, J=6.3 Hz, 3H), 1.26 (d, J=7.1 Hz, 3H), 1.25-1.23 (m, 1H), 1.20 (d, J=6.7 Hz, 3H), 0.94 (s, 3H). LC/MS: (ES+) [M+H]$^+$ (822, 100%).

Example 7: Preparation of Maytansinoid Compound 12

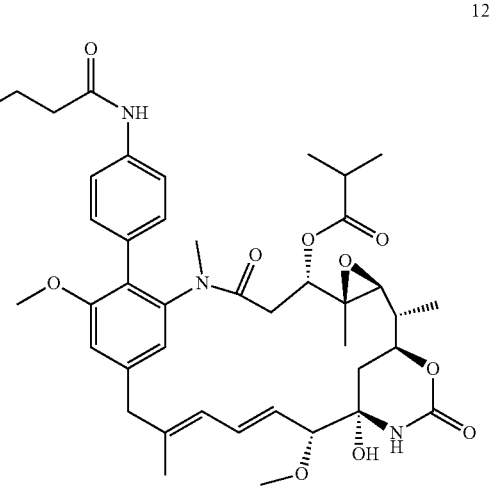

12

Step 1: Synthesis of Compound 13.

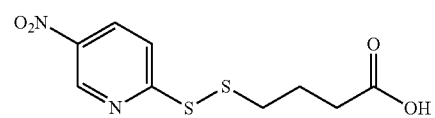

13

To a stirred solution of 2,2'-dithiobis(5-nitropyridine) (682 mg) and 4-methylmorpholine (NMM, 600 μL) in THF (10 mL) was slowly added a solution of 4-mercaptobutyric acid (222 mg) in ethyl acetate (2 mL) and the combined solution was stirred at room temperature for 1 h. The reaction mixture was then diluted with saturated sodium hydrogen carbonate solution (10 mL), water (10 mL) and ethyl acetate (30 mL). The organic layer was separated and washed with saturated sodium hydrogen carbonate solution (20 mL). The aqueous layers were combined and acidified with 1 M HCl (70 mL) before extracting with ethyl acetate (2×50 mL). The combined organic layers were then dried over sodium sulfate, filtered and concentrated in vacuo. The residue was purified by normal phase chromatography eluting with hexane (0.5% acetic acid):ethyl acetate (100:0 v/v to 60:40 v/v). The solvent was removed in vacuo to give compound 13 as a pale yellow solid (82 mg). $^{1}$H NMR (500 MHz, CDCl$_{3}$) δ 9.28 (s, 1H), 8.40 (dd, J=8.8, 2.6 Hz, 1H), 7.87 (d, J=8.8 Hz, 1H), 2.91 (t, J=7.1 Hz, 2H), 2.54 (t, J=7.1 Hz, 2H), 2.05 (quintet, J=7.1 Hz, 2H). LC/MS: (ES+) [M+H]$^{+}$ (275, 100%).

Step 2: Synthesis of Compound 14.

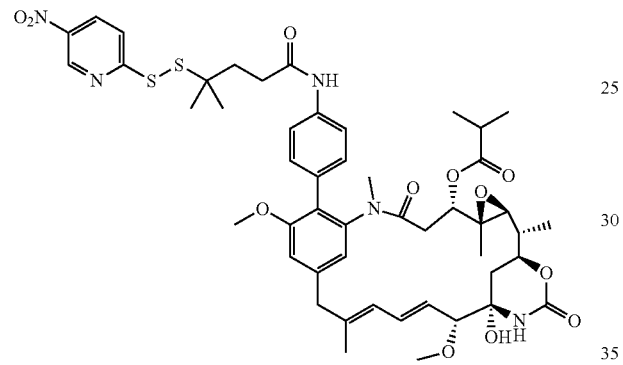

Compound 14 was synthesised in an analogous way to compound 8 of Example 5 using compound 13 instead of compound 7. Compound 14 was isolated as a pale yellow solid. $^{1}$H NMR (500 MHz; CDCl$_{3}$) δ 9.30 (d, J=2.2 Hz, 1H), 8.43 (dd, J=8.8, 2.5 Hz, 1H), 7.92 (d, J=9.0 Hz, 1H), 7.57-7.54 (m, 1H), 7.44-7.41 (m, 1H), 7.11-7.08 (m, 2H), 6.90-6.88 (m, 2H), 6.53-6.48 (m, 1H), 6.23-6.19 (m, 2H), 5.52-5.47 (m, 1H), 4.86-4.83 (m, 1H), 4.31-1.29 (m, 1H), 3.84 (s, 3H), 3.59 (d, J=13.1 Hz, 1H), 3.54 (d, J=9.0 Hz, 1H), 3.39 (s, 3H), 3.29 (d, J=12.7 Hz, 1H), 3.04-2.97 (m, 5H), 2.69 (s, 3H), 2.67-2.62 (m, 1H), 2.58-2.55 (m, 2H), 2.27-2.24 (m, 1H), 2.21-2.15 (m, 2H), 1.77 (s, 3H), 1.70 (ddd, J=13.0, 1.4, 0.6 Hz, 1H), 1.54-1.50 (m, 1H), 1.32 (d, J=6.4 Hz, 3H), 1.28 (d, J=11.2 Hz, 4H), 1.27-1.26 (m, 1H), 1.22 (d, J=6.7 Hz, 3H), 0.96 (s, 3H). LC/MS: (ES+) [M+H]$^{+}$ (948, 100%).

Step 3: Synthesis of Compound 12.

Compound 12 was synthesised in an analogous way to compound 6 of Example 5 using compound 14 instead of compound 8. Compound 12 was isolated as a white solid. $^{1}$H NMR (500 MHz; CDCl$_{3}$) δ 7.56-7.54 (m, 1H), 7.49 (d, J=3.9 Hz, 1H), 7.08-7.07 (m, 2H), 6.86 (d, J=8.8 Hz, 2H), 6.49 (dd, J=15.3, 11.0 Hz, 1H), 6.21-6.18 (m, 2H), 5.47 (dd, J=15.3, 9.0 Hz, 1H), 4.81-1.81 (m, 1H), 4.32-4.27 (m, 1H), 3.81 (s, 3H), 3.56 (d, J=13.0 Hz, 1H), 3.52 (d, J=9.0 Hz, 1H), 3.37 (s, 3H), 3.28-3.25 (m, 1H), 3.04-2.95 (m, 3H), 2.67 (s, 3H), 2.65-2.61 (m, 2H), 2.53 (t, J=7.2 Hz, 2H), 2.26-2.22 (m, 1H), 2.07-2.02 (m, 2H), 1.75 (s, 3H), 1.69 (d, J=0.4 Hz, 1H), 1.54-1.48 (m, 1H), 1.38 (t, J=8.0 Hz, 1H), 1.30 (d, J=6.3 Hz, 3H), 1.26 (d, J=7.2 Hz, 3H), 1.25-1.24 (m, 1H), 1.20 (d, J=6.7 Hz, 3H), 0.94 (s, 3H). LC/MS: (ES+) [M+H]$^{+}$ (794, 100%).

Example 8: Preparation of Maytansinoid Compound 15

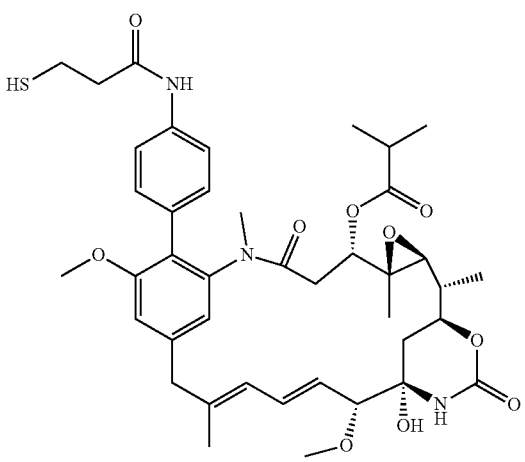

Step 1: Synthesis of Compound 16.

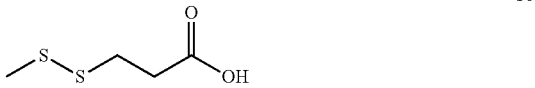

To a stirred solution of 3-mercapto-propionic acid (0.41 mL) in water (15 mL) at 0° C. was added a solution of S-methyl methanethiolsulfonate (0.49 mL) in ethanol (7.5 mL). The reaction mixture was allowed to warm to room temperature and was stirred for 18 h before concentrating in vacuo. Saturated sodium hydrogen carbonate solution (8 mL) was added to the residue until a pH of 7-8 was achieved and the resulting mixture was then extracted with dichloromethane (2×10 mL). The layers were separated and the aqueous layer was acidified with 0.1 M HCl solution (12 mL) and then 1 M HCl solution (6 mL) to achieve a solution pH of 2-3. The aqueous layer was then extracted with ethyl acetate (2×40 mL). The organic layers were separated and combined, dried over sodium sulfate, filtered and concentrated in vacuo to give compound 16 as a white solid (0.71 g). $^{1}$H NMR (500 MHz; CDCl$_{3}$) δ 2.94 (t, J=6.8 Hz, 2H), 2.83 (d, J=6.8 Hz, 2H), 2.42 (s, 3H). LC/MS: (ES+) [M+H]$^{+}$ (152, 100%).

Step 2: Synthesis of Compound 17.

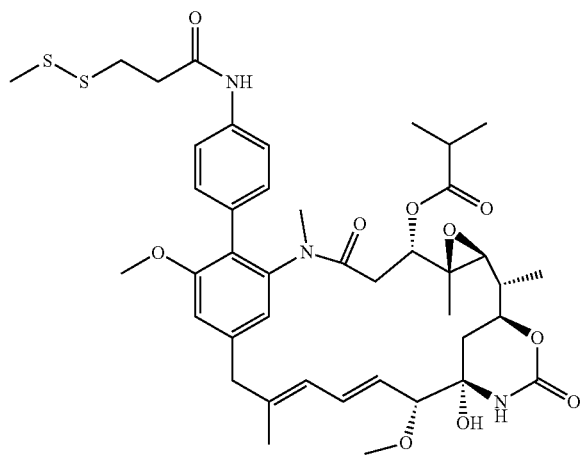

Compound 17 was synthesised in an analogous way to compound 8 of Example 5 using compound 16 instead of compound 7. Compound 17 was isolated as a white solid. LC/MS: (ES+) [M+H]$^+$ (826, 100%).

Step 3: Synthesis of Compound 15.

Compound 15 was synthesised in an analogous way to compound 6 of Example 5 using compound 17 instead of compound 8. Compound 15 was isolated as a white solid. $^1$H NMR (500 MHz; CDCl$_3$) δ 7.63 (s, 1H), 7.57-7.55 (m, 1H), 7.09-7.07 (m, 2H), 6.87 (d, J=8.2 Hz, 2H), 6.49 (dd, J=15.3, 11.1 Hz, 1H), 6.22-6.18 (m, 2H), 5.47 (dd, J=15.3, 9.1 Hz, 1H), 4.85-4.82 (m, 1H), 4.32-4.27 (m, 1H), 3.82 (s, 3H), 3.57 (d, J=13.0 Hz, 1H), 3.52 (d, J=8.9 Hz, 1H), 3.37 (s, 3H), 3.26 (d, J=12.7 Hz, 1H), 3.04-2.95 (m, 3H), 2.90 (q, J=7.4 Hz, 2H), 2.70 (dd, J=8.7, 4.5 Hz, 2H), 2.67 (s, 3H), 2.64-2.60 (m, 1H), 2.24 (dd, J=13.9, 2.6 Hz, 1H), 1.75 (s, 3H), 1.72 (d, J=8.5 Hz, 1H), 1.70-1.66 (m, 1H), 1.54-1.48 (m, 1H), 1.30 (d, J=6.4 Hz, 3H), 1.26 (d, J=7.2 Hz, 3H), 1.24-1.23 (m, 1H), 1.20 (d, J=6.8 Hz, 3H), 0.94 (s, 3H). LC/MS: (ES+) [M+H]$^+$ (780, 100%).

Example 9: Preparation of Maytansinoid Compound 18

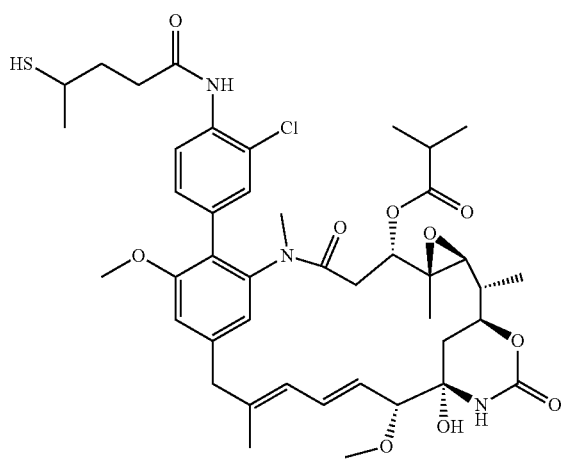

Step 1: Synthesis of Compound 19.

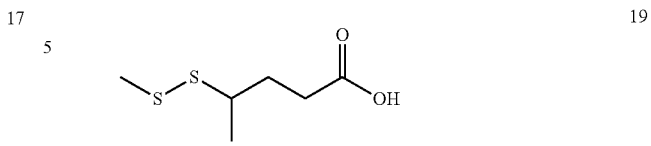

To a solution of 4-mercapto-pentanoic acid (0.97 g) in ethanol:water (10 mL, 1:1 v/v) was added S-methyl methanethiolsulfonate (0.72 mL) and the reaction mixture was stirred under an argon atmosphere at room temperature for 22 h. The ethanol was removed under reduced pressure before the reaction solution was diluted with brine (10 mL) and extracted with ethyl acetate (3×15 mL). The combined organic layers were then washed with brine (15 mL), the organic layer was separated, dried over sodium sulfate, filtered and concentrated in vacuo to give compound 19 as a yellow oil (0.9 g). $^1$H NMR (300 MHz; CDCl$_3$): δ 9.09 (s, 1H), 2.89 (m, 1H), 2.52 (t, J=7.6 Hz, 2H), 2.41 (s, 3H), 2.03-1.85 (m, 2H), 1.35 (d, J=6.8 Hz, 3H).

Step 2: Synthesis of Compound 20.

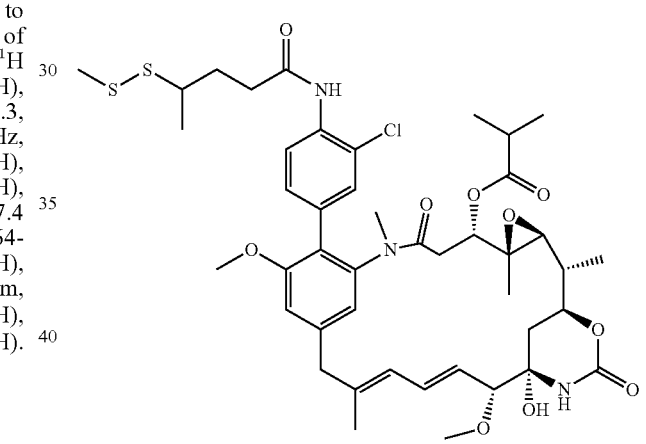

To a solution of compound 19 (33 mg) in anhydrous THF (2 mL) at 0° C. under an argon atmosphere was added isobutyl chloroformate (25 μL) and NMM (50 μL). After stirring for 20 min at 0° C., a solution of compound 5 (42 mg) in anhydrous THF (4 mL) was slowly added to the reaction mixture which was allowed to warm to room temperature and was stirred for a further 16 h. A solution of compound 19 (33 mg) and isobutyl chloroformate (25 μL) in anhydrous THF (1 mL), which had been stirred under an argon atmosphere at room temperature for 1 h, was then added to the reaction mixture. The reaction solution was then stirred for 24 h before the solvent was removed in vacuo and the residue purified by reverse phase C-18 column chromatography eluting with buffer A (v/v): water: 0.05% acetic acid and buffer B (v/v): acetonitrile:0.05% acetic acid (80:20 v/v to 0:100 v/v). The desired fractions were combined and lyophilised to give compound 20 as a white solid (20 mg). $^1$H NMR (500 MHz; CDCl$_3$): δ 8.42 (s, 1H), 7.70 (s, 1H), 7.12 (s, 1H), 7.04 (d, J=7.0 Hz, 1H), 6.88 (s, 1H), 6.85 (s, 1H), 6.48 (dd, J=15.4, 11.1 Hz, 1H), 6.21-6.17 (m, 2H), 5.47 (dd, J=15.5, 8.9 Hz, 1H), 4.83 (dd, J=11.9, 2.3 Hz, 1H), 4.30 (t, J=10.8 Hz, 1H), 3.82 (s, 3H), 3.56 (d, J=13.0 Hz, 1H), 3.52 (d, J=9.0 Hz, 1H), 3.37 (s, 3H), 3.27 (d, J=12.4 Hz, 2H), 3.00 (d, J=9.5 Hz, 2H), 2.94-2.89 (m, 3H), 2.73 (s, 3H), 2.64 (dq, J=21.7, 7.3 Hz, 3H), 2.43 (d, J=3.6 Hz, 1H), 2.23-2.21 (m, 1H), 2.17-2.15 (m, 1H), 2.06 (dd, J=13.1, 7.4 Hz, 1H), 1.75 (s, 3H), 1.67 (d, J=13.7 Hz, 1H), 1.50 (d, J=6.6 Hz, 3H), 1.40 (d, J=6.7 Hz, 1H), 1.31 (d, J=6.2 Hz, 3H), 1.26 (q, J=8.2 Hz, 5H), 1.20 (d, J=6.7 Hz, 3H), 0.94 (s, 3H). LC/MS: (ES+) [M+H]+ (888, 100%).

Step 3: Synthesis of Compound 18.

Compound 18 was synthesised in an analogous way to compound 6 of Example 5 using compound 20 instead of compound 8. $^1$H NMR (500 MHz; CDCl$_3$): δ 8.41 (s, 1H), 7.70 (s, 1H), 7.12 (s, 1H), 7.04 (d, J=6.8 Hz, 1H), 6.88 (s, 1H), 6.85 (s, 1H), 6.48 (dd, J=15.2, 11.2 Hz, 1H), 6.21-6.17 (m, 2H), 5.47 (dd, J=15.4, 9.0 Hz, 1H), 4.84-4.80 (m, 1H), 4.30 (t, J=11.0 Hz, 1H), 3.82 (s, 3H), 3.56 (d, J=12.8 Hz, 1H), 3.52 (d, J=8.9 Hz, 1H), 3.37 (s, 3H), 3.27 (d, J=12.7 Hz, 1H), 2.99 (t, J=8.4 Hz, 1H), 2.92 (t, J=12.8 Hz, 1H), 2.73 (s, 3H), 2.67-2.59 (m, 2H), 2.22 (d, J=13.9 Hz, 1H), 2.08-2.04 (m, 1H), 1.75 (s, 3H), 1.67 (d, J=14.3 Hz, 2H), 1.50 (d, J=6.6 Hz, 3H), 1.36 (d, J=6.8 Hz, 2H), 1.30 (t, J=6.6 Hz, 6H), 1.20 (d, J=6.6 Hz, 3H), 0.94 (s, 3H), 0.88 (dd, J=11.6, 5.5 Hz, 3H). LC/MS: (ES+) [M+H]+ (842, 100%).

Example 10: Preparation of Maytansinoid Compound 21

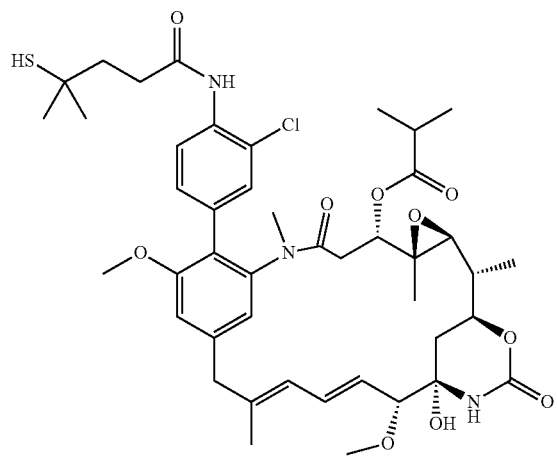

21

Step 1: Synthesis of Compound 22.

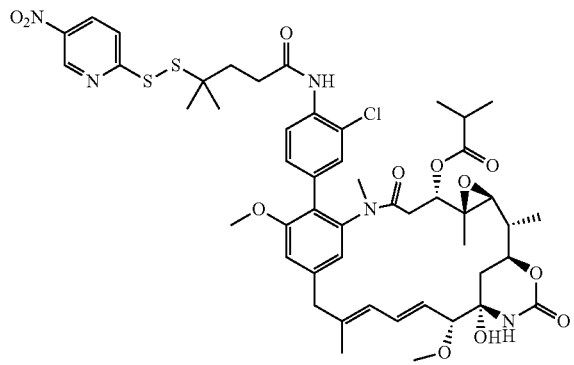

22

Compound 22 was synthesised in an analogous way to compound 8 of Example 5 using compound 5 instead of compound 4 and using compound 10 instead of compound 7. Compound 22 was isolated as a white solid. LC/MS: (ES+) [M+H]+ (1010, 100%).

Step 2: Synthesis of Compound 21.

Compound 21 was synthesised in an analogous way to compound 6 of Example 5 using compound 22 instead of compound 8. Compound 21 was isolated as a white solid. $^1$H NMR (500 MHz; CDCl$_3$) δ 8.44-8.42 (m, 1H), 7.69 (d, J=0.3 Hz, 1H), 7.12 (d, J=0.6 Hz, 1H), 7.06-7.04 (m, 1H), 6.86 (d, J=11.8 Hz, 2H), 6.51-6.45 (m, 1H), 6.22-6.17 (m, 2H), 5.47 (dd, J=15.4, 9.0 Hz, 1H), 4.84-4.82 (m, 1H), 4.84-4.82 (m, 1H), 4.32-4.27 (m, 1H), 3.82 (s, 3H), 3.56 (d, J=13.0 Hz, 1H), 3.52 (d, J=9.0 Hz, 1H), 3.37 (s, 3H), 3.27 (d, J=12.7 Hz, 1H), 3.00 (d, J=9.5 Hz, 2H), 2.92 (t, J=12.9 Hz, 1H), 2.72 (s, 3H), 2.66-2.60 (m, 3H), 2.24-2.21 (m, 1H), 2.04 (dd, J=9.2, 6.8 Hz, 2H), 1.75 (s, 3H), 1.67 (d, J=11.3 Hz, 1H), 1.54-1.48 (m, 1H), 1.44 (s, 6H), 1.31 (d, J=6.3 Hz, 3H), 1.25 (s, 3H), 1.25-1.23 (m, 1H), 1.20 (d, J=6.7 Hz, 3H), 0.94 (s, 3H). LC/MS: (ES+) [M+H]+ (856, 100%).

Example 11: Preparation of Maytansinoid Compound 23

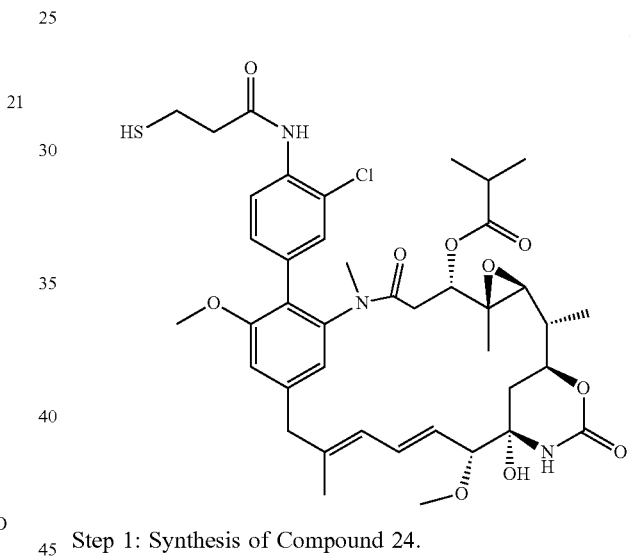

23

Step 1: Synthesis of Compound 24.

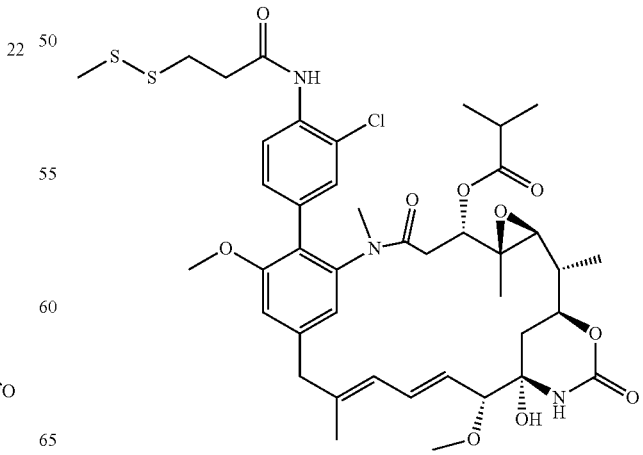

24

To a stirred solution of compound 5 (50 mg), compound 16 (29 mg) and HATU (79 mg) in DMF (1.5 mL) at 0° C. was slowly added DIPEA (50 µL). The reaction mixture was allowed to warm to room temperature and was stirred for 14 h. Additional quantities of compound 16 (47 mg) in DMF (500 µL), HATU (129 mg) and DIPEA (100 µL) were added and the reaction mixture was stirred at room temperature for a further 6 h. The reaction mixture was then directly purified by reverse phase C-18 column chromatography eluting with buffer A (v/v): water:0.1% acetic acid and buffer B (v/v): acetonitrile:0.1% acetic acid (100:0 v/v to 0:100 v/v). The desired fractions were combined and lyophilised to give compound 24 as a white solid (15 mg). LC/MS: (ES+) [M+H]$^+$ (860, 100%).

Step 2: Synthesis of Compound 23.

Compound 23 was synthesised in an analogous way to compound 6 of Example 5 using compound 24 instead of compound 8. Compound 23 was isolated as a white solid. NMR (500 MHz; CDCl$_3$) $^1$H NMR (500 MHz; CDCl$_3$) δ 8.45-8.43 (m, 1H), 7.75 (s, 1H), 7.13 (s, 1H), 7.06 (d, J=8.2 Hz, 1H), 6.88-6.85 (m, 2H), 6.48 (dd, J=15.4, 11.0 Hz, 1H), 6.21-6.17 (m, 2H), 5.47 (dd, J=15.5, 9.0 Hz, 1H), 4.83 (dd, J=11.8, 2.9 Hz, 1H), 4.32-4.27 (m, 1H), 3.82 (s, 3H), 3.56 (d, J=12.9 Hz, 1H), 3.52 (d, J=8.9 Hz, 1H), 3.37 (s, 3H), 3.27 (d, J=12.8 Hz, 1H), 3.02-2.99 (m, 2H), 2.94-2.90 (m, 3H), 2.78 (t, J=6.5 Hz, 2H), 2.73 (s, 3H), 2.65-2.60 (m, 1H), 2.23 (dd, J=13.7, 2.8 Hz, 1H), 1.74 (s, 3H), 1.67 (d, J=13.1 Hz, 1H), 1.53-1.47 (m, 1H), 1.31 (d, J=6.3 Hz, 3H), 1.26 (d, J=7.2 Hz, 3H), 1.25-1.23 (m, 1H), 1.20 (d, J=6.7 Hz, 3H), 0.94 (s, 3H). LC/MS: (ES+) [M+H]$^+$ (814, 100%).

Example 12: Preparation of Conjugation Reagent 25 Comprising a Maytansinoid Cytotoxic Payload

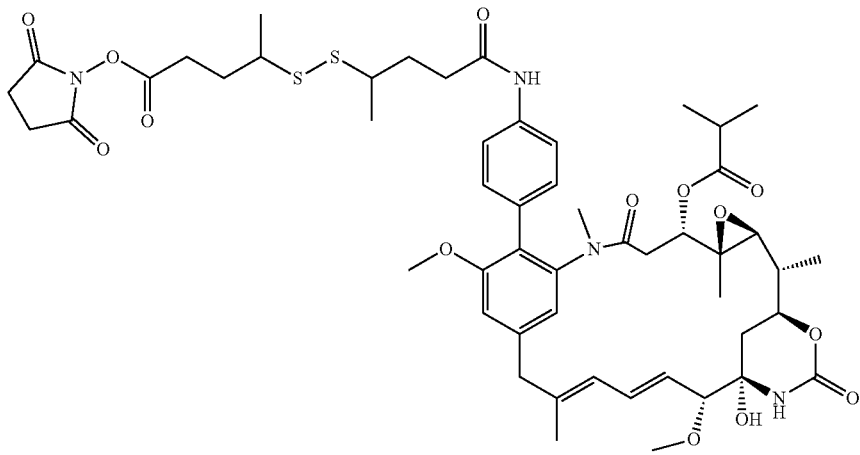

25

Step 1: Synthesis of Compound 26.

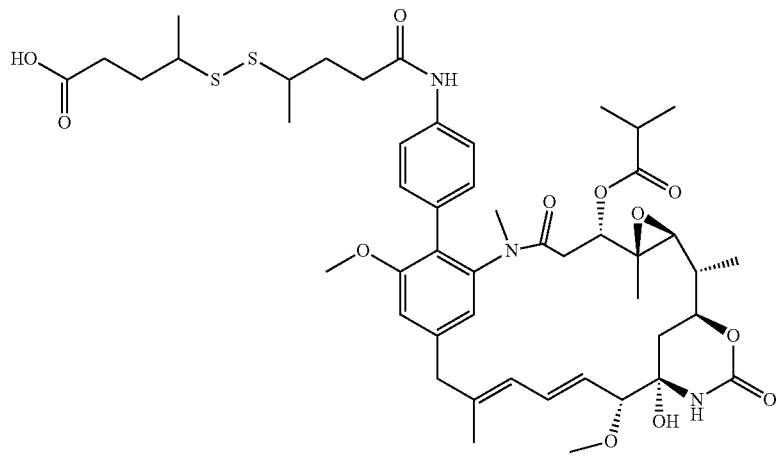

26

A mixture of compound 8 (17 mg) and 4-mercaptopentanoic acid (10 mg) in DMF (2 mL) was stirred at room temperature for 16 h. The reaction mixture was then diluted with ethyl acetate (20 mL) and washed with brine (10 mL). The organic layer was separated and concentrated in vacuo before the residue was dissolved in DMF (6 mL) and purified by reverse phase C-18 column chromatography eluting with buffer A (v/v): water:0.1% acetic acid and buffer B (v/v): acetonitrile:0.1% acetic acid (100:0 v/v to 0:100 v/v). The desired fractions were combined and lyophilised to give compound 26 as an off-white solid (23 mg). $^1$H NMR (500 MHz; CDCl$_3$) δ 8.17 (s, 1H), 7.59-7.58 (m, 2H), 7.06-7.05 (m, 2H), 6.86 (s, 2H), 6.48 (dd, J=15.3, 11.1 Hz, 1H), 6.41 (s, 1H), 6.18 (d, J=10.9 Hz, 1H), 5.47 (dd, J=15.4, 8.9 Hz, 1H), 4.79 (d, J=12.0 Hz, 1H), 4.29 (t, J=11.3 Hz, 1H), 3.81 (s, 3H), 3.56 (d, J=13.0 Hz, 1H), 3.52 (d, J=8.9 Hz, 1H), 3.37 (s, 3H), 3.26 (d, J=12.9 Hz, 1H), 2.96 (d, J=9.2 Hz, 2H), 2.90-2.84 (m, 2H), 2.66 (d, J=3.7 Hz, 3H), 2.62 (dd, J=14.0, 7.0 Hz, 2H), 2.55-2.40 (m, 4H), 2.32-2.25 (m, 1H), 2.07-1.95 (m, 3H), 1.79 (t, J=6.9 Hz, 1H), 1.74 (s, 3H), 1.68-1.65 (m, 1H), 1.53-1.46 (m, 1H), 1.34 (d, J=6.4 Hz, 3H), 1.27 (d, J=6.6 Hz, 6H), 1.24 (d, J=7.2 Hz, 3H), 1.24-1.23 (m, 1H), 1.19 (d, J=6.7 Hz, 3H), 0.94 (s, 3H). LC/MS: (ES+) [M+H]$^+$ (940, 100%).

Step 2: Synthesis of Reagent 25.

A mixture of compound 26 (23 mg), N-(3-dimethylaminopropyl)-N'-ethylcarbodiimide hydrochloride (EDC.HCl, 12 mg) and N-hydroxysuccinimide (5 mg) in anhydrous dichloromethane (2 mL) was stirred at room temperature for 4 h. The reaction mixture was then concentrated in vacuo and the residue dissolved in DMSO (5 mL) before purification by reverse phase C-18 column chromatography eluting with buffer A (v/v): water:0.1% acetic acid and buffer B (v/v): acetonitrile:0.1% acetic acid (100:0 v/v to 0:100 v/v). The desired fractions were combined and lyophilised to give reagent 25 as a white solid (25 mg). $^1$H NMR (500 MHz; CDCl$_3$) δ 7.75-7.69 (m, 1H), 7.58-7.54 (m, 2H), 7.08-7.06 (m, 2H), 6.87-6.85 (m, 2H), 6.48 (dd, J=15.4, 11.0 Hz, 1H), 5.47 (dd, J=15.4, 9.0 Hz, 1H), 4.84-1.81 (m, 1H), 4.32-4.27 (m, 1H), 3.81 (s, 3H), 3.56 (d, J=13.0 Hz, 1H), 3.52 (d, J=8.9 Hz, 1H), 3.37 (s, 3H), 3.26 (d, J=13.0 Hz, 1H), 3.01-2.84 (m, 6H), 2.82 (d, J=1.0 Hz, 3H), 2.80-2.73 (m, 2H), 2.67 (s, 3H), 2.64-2.60 (m, 1H), 2.53-2.50 (m, 2H), 2.25-2.21 (m, 1H), 2.15-2.11 (m, 1H), 2.06-1.96 (m, 3H), 1.75 (s, 3H), 1.68 (d, J=13.5 Hz, 1H), 1.53-1.47 (m, 1H), 1.37 (d, J=6.8 Hz, 3H), 1.34-1.30 (m, 6H), 1.26 (d, J=7.2 Hz, 3H), 1.24-1.23 (m, 1H), 1.20 (d, J=6.8 Hz, 3H), 0.94 (s, 3H). LC/MS: (ES+) [M+H]$^+$ (1037, 100%).

Example 13: Preparation of Conjugation Reagent 27 Comprising a Maytansinoid Cytotoxic Payload

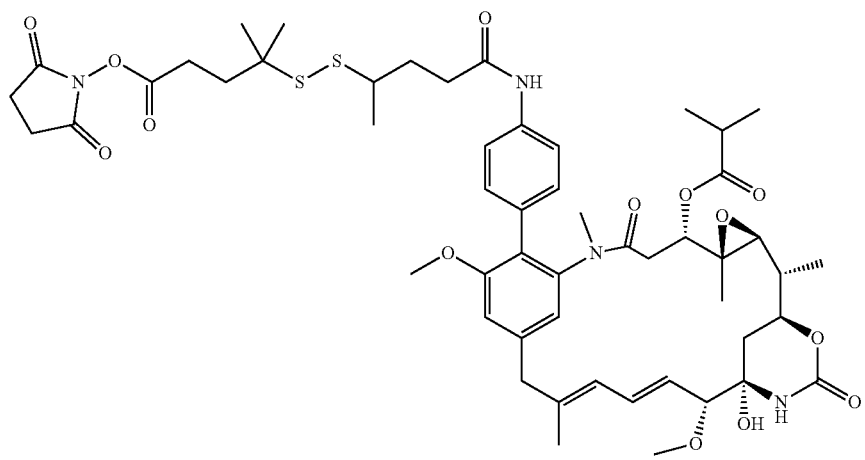

27

Step 1: Synthesis of Compound 28.

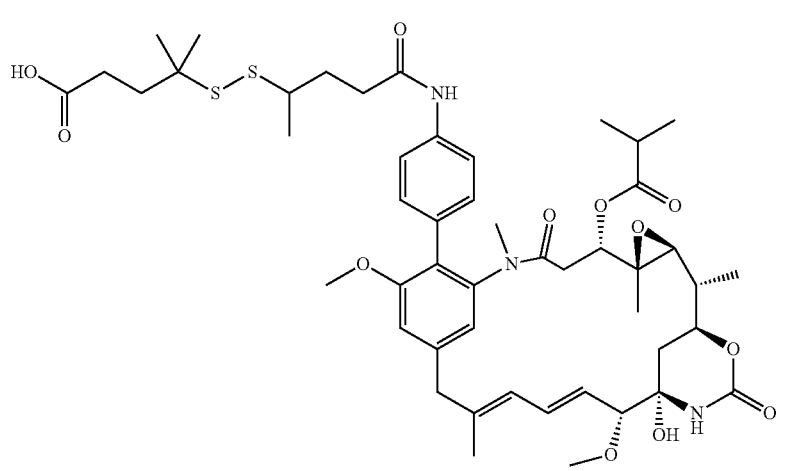

28

Compound 28 was synthesised in an analogous way to compound 26 of Example 12 using 4-mercapto-4-methyl-pentanoic acid instead of 4-mercapto-pentanoic acid. Compound 28 was isolated as a white solid. $^1$H NMR (500 MHz; CD$_3$OD) δ 7.63-7.62 (m, 2H), 6.96 (s, 1H), 6.71-6.66 (m, 1H), 6.29-6.27 (m, 1H), 5.58-5.53 (m, 1H), 4.76-1.73 (m, 1H), 4.26-4.22 (m, 1H), 3.83 (s, 3H), 3.63-3.60 (m, 2H), 3.39 (s, 3H), 3.36 (m, 1H), 3.07-3.02 (m, 1H), 2.99-2.94 (m, 1H), 2.89-2.87 (m, 1H), 2.79-2.74 (m, 1H), 2.70 (s, 3H), 2.63-2.54 (m, 2H), 2.40-2.37 (m, 2H), 2.27-2.24 (m, 1H), 2.06-1.90 (m, 5H), 1.80 (s, 3H), 1.65-1.54 (m, 3H), 1.36 (d, J=6.8 Hz, 3H), 1.29-1.27 (d, 13H), 1.22 (d, J=6.7 Hz, 3H), 1.02 (s, 3H). LC/MS: (ES+) [M+H]$^+$ (954, 100%).

Step 2: Synthesis of Reagent 27.

Reagent 27 was synthesised in an analogous way to reagent 25 of Example 12 using compound 28 instead of compound 26. Reagent 27 was isolated as a white solid. $^1$H NMR (500 MHz; CDCl$_3$) δ 7.89 (d, J=4.9 Hz, 1H), 7.58-7.56 (m, 2H), 7.07 (d, J=8.1 Hz, 2H), 6.86 (d, J=6.4 Hz, 2H), 6.48 (dd, J=15.3, 11.1 Hz, 1H), 6.23 (s, 1H), 6.18 (d, J=10.9 Hz, 1H), 5.47 (dd, J=15.4, 9.0 Hz, 1H), 4.84-4.81 (m, 1H), 4.32-4.27 (m, 1H), 3.81 (s, 3H), 3.56 (d, J=12.9 Hz, 1H), 3.52 (d, J=9.0 Hz, 1H), 3.37 (s, 3H), 3.26 (d, J=12.8 Hz, 1H), 3.06 (s, 1H), 3.00-2.94 (m, 2H), 2.87-2.83 (m, 6H), 2.77-2.71 (m, 2H), 2.66 (s, 3H), 2.64-2.60 (m, 1H), 2.55-2.48 (m, 2H), 2.24 (d, J=13.4 Hz, 1H), 2.09-1.96 (m, 4H), 1.75 (s, 3H), 1.68 (d, J=13.5 Hz, 1H), 1.54-1.46 (m, 1H), 1.34 (d, J=6.7 Hz, 3H), 1.30-1.28 (m, 9H), 1.25-1.24 (m, 1H), 1.26 (d, J=7.2 Hz, 3H), 1.20 (d, J=6.7 Hz, 3H), 0.94 (s, 3H). LC/MS: (ES+) [M+H]$^+$ (1051, 100%).

Example 14: Conjugation of Reagents 25 and 27 to Trastuzumab to Produce Antibody Drug Conjugates (ADCs) 29 and 30, Respectively Conjugation reagents 25 and 27 were conjugated to Trastuzumab, giving rise to ADCs 29 and 30, respectively. Briefly, the reagents were dissolved in DMSO to give 10 mM stock solutions. To a solution of Trastuzumab in 100 mM sodium phosphate buffer, 100 mM sodium chloride, pH 8.0 was added propylene glycol (40% v/v) and the solution mixed gently to give a final antibody concentration of 4.8 mg/mL. Conjugation reagents (13 eq. per mAb) were then added to the antibody solutions and the reaction mixtures were mixed gently and incubated at 24° C. for 3 h. Activated charcoal powder (70% w/w of mAb) was then added to the reaction solutions which were gently agitated for 30 min at room temperature to remove unreacted drug related species. The reaction mixtures were then filtered (0.22 μm PES membrane) and the purified sample was buffer exchanged into 10 mM succinic acid, 6% w/v trehalose, 0.01% v/v Tween 20, pH 5.5 using PD-10 desalting columns.

The DARs of the conjugates were determined by mass spectrometry following deglycosylation of the samples using PNGase F. The average DARs of the conjugates were calculated from the relative peak intensities of the individual DAR species. DAR assignments of 3.3 and 2.8 were determined for antibody drug conjugates 29 and 30, respectively.

Example 15: In Vitro Potency Assay of Compounds in SK-BR-3 Cell Lines

Loss of tumour cell viability following treatment with compounds of the invention was tested by growing SK-BR-3 cell lines in the presence of increasing concentrations of compounds of the invention and quantifying the loss of proliferation or metabolic activity as described in Example 2. The average IC$_{50}$ values for compounds of the invention are shown in Table 3 and the assay concentrations are specified in Table 4. The IC$_{50}$ value for a comparator compound 31:

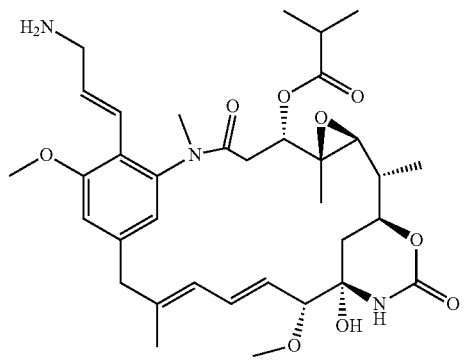

from Chem. Eur. J. 2012, 18, 880-886 is also provided.

TABLE 3

| Compound number | Average IC$_{50}$ (nM) SK-BR-3 Cell line |
|---|---|
| 4 | 1.2 (n = 4) |
| 5 | 1.2 (n = 2) |
| 6 | 2.7 (n = 3) |
| 18 | 0.9 (n = 2) |
| 31 (comparator) | 33.4 (n = 3) |

TABLE 4

| Cell line | Compound | Concentration range |
|---|---|---|
| SK-BR-3 | 4 | 200 nM-2.6 pM |
| SK-BR-3 | 5 | 200 nM-2.6 pM |
| SK-BR-3 | 6 | 200 nM-0.2 pM |
| SK-BR-3 | 18 | 200 nM-2.6 pM |
| SK-BR-3 | 31 (comparator) | 1000 nM-457 pM |

Compounds of the invention, which contain a biphenyl moiety, unexpectedly have lower IC$_{50}$ values with respect to inhibiting proliferation of SK-BR-3 cells, than an allylamine-containing comparator compound.

Example 16: JIMT-1 Mouse Xenograft Study Comparing Trastuzumab-Drug Conjugate 29 to Kadcyla® (Comparative)

Conjugate 29 was prepared as described in Example 14. Healthy female NMRI nude mice (RjOrl:NMRI-Foxn1$^{nu}$/Foxn1$^{nu}$) aged 6 weeks at arrival were used for cell inoculation.

Tumours were induced by subcutaneous injection of 5×10$^6$ JIMT-1 cells (breast carcinoma) in 200 μL of cell suspension in PBS into the right flank. Matrigel (40 μL Matrigel per 200 μL cell suspension) was added shortly before inoculation of tumour cells. Tumours were measured twice a week with calipers, and the volume was estimated using the formula:

$$\text{Tumor Volume (mm}^3\text{)} = \frac{\text{width}^2 \times \text{length}}{2}$$

When the tumour volumes reached a mean tumour volume of approximately 134 mm$^3$, the animals were randomised into groups of eight mice and treatment was initiated (Day 0). All test substances were injected via the tail vein (i.v. bolus). A single dose of 30 mg/kg of ADC was given in 10 mL/kg and PBS was used for the vehicle group.

Mice viability and behaviour were recorded every day. Body weights were measured twice a week. The animals were euthanized when a humane endpoint was reached (e.g. calculated tumour weight of >10% body weight and/or tumour volume >2000 mm$^3$ animal body weight loss of >20% compared to the body weight at group distribution, ulceration of tumours, lack of mobility, general signs of pain), or at a pre-determined study end date.

Figure 3:
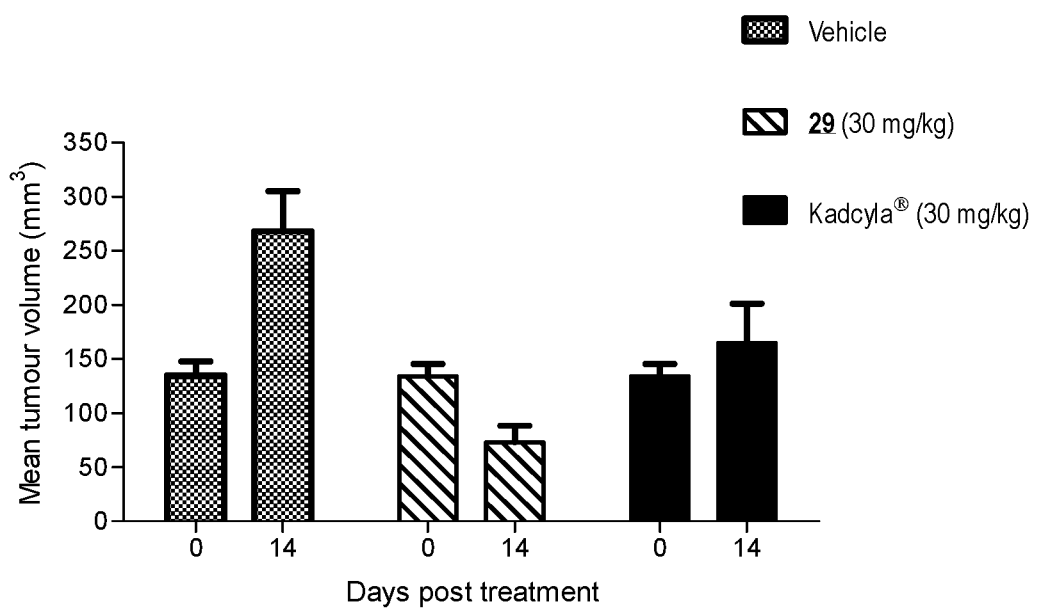
FIG. 3 shows the results of the mouse xenograft study described in Example 16, showing a plot of mean tumour volume±standard error over time following administration of vehicle, conjugate 29 of the invention, or of Kadcyla® to mice.

The mean tumour volumes±standard error at Day 0 and Day 14 post treatment are represented in FIG. 3. Results show that for vehicle treated animals, the tumour volume approximately doubled between Day 0 and Day 14 (135 Vs 268 mm$^3$). For animals treated with conjugate 29, (30 mg/Kg dose), by Day 14 the tumour volume was reduced to almost half the value recorded at Day 0 (134 Vs 73 mm$^3$), whereas the clinical product Kadcyla® displayed an increase in tumour volume over the same time period (134 Vs 165 mm$^3$). All compounds were well tolerated.

Example 17: Preparation of Maytansinoid Compound 32

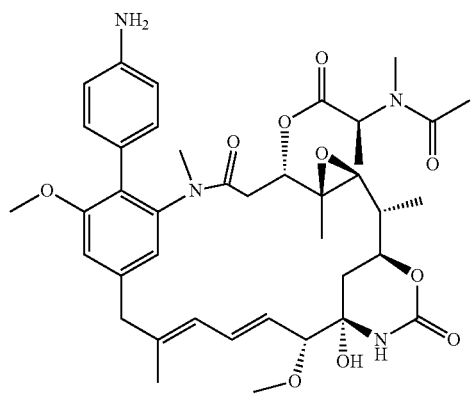

Compound 32 was synthesised in an analogous way to compound 4 of Example 3. Briefly, 4-aminophenylboronic acid pinacol ester (16 mg), tripotassium phosphate (33 mg), SPhos Pd G3 (6 mg) and maytansine (available from Toronto Research Chemicals, 25 mg) were sequentially added to an argon purged reaction vessel. The vessel was then sealed and the solids purged with argon (4×evacuation/purge cycles). THF (600 μL) and water (60 μL), which had been rigorously deoxygenated by purging with argon, were then added and the reaction mixture was stirred at room temperature for 17 h. The reaction mixture was then diluted with ethyl acetate (20 mL) and washed with brine (10 mL). The layers were separated and the organic layer was concentrated under reduced pressure. The residue was then purified by reverse phase C-18 column chromatography eluting with buffer A (v/v): water:0.1% acetic acid and buffer B (v/v): acetonitrile:0.1% acetic acid (100:0 v/v to 0:100 v/v) and the desired fractions lyophilised to give compound 32 as a white solid (17.3 mg). $^1$H NMR (500 MHz; CDCl$_3$) δ 6.90 (d, J=7.9 Hz, 2H), 6.82 (s, 1H), 6.72-6.66 (m, 3H), 6.66 (s, 1H), 6.46 (dd, J=15.4, 11.2 Hz, 1H), 6.23 (s, 1H), 5.70 (dd, J=15.3, 9.0 Hz, 1H), 5.35-5.31 (m, 1H), 4.82 (dd, J=12.0, 2.7 Hz, 1H), 4.32-4.28 (m, 1H), 3.81 (s, 3H), 3.68 (d, J=12.8 Hz, 1H), 3.52 (d, J=9.0 Hz, 1H), 3.42-3.41 (m, 1H), 3.37 (s, 3H), 3.15 (d, J=12.7 Hz, 1H), 3.10-3.03 (m, 2H), 2.81 (s, 3H), 2.68 (s, 3H), 2.26 (dd, J=14.3, 2.6 Hz, 1H), 2.07 (s, 3H), 1.68 (s, 3H), 1.65 (d, J=13.7 Hz, 1H), 1.54-1.48 (m, 1H), 1.32-1.30 (m, 6H), 1.26 (d, J=13.0 Hz, 1H), 0.92 (s, 3H). LC/MS: (ES+) [M+H]$^+$ (749, 100%).

Example 18: Preparation of Maytansinoid Compound 33

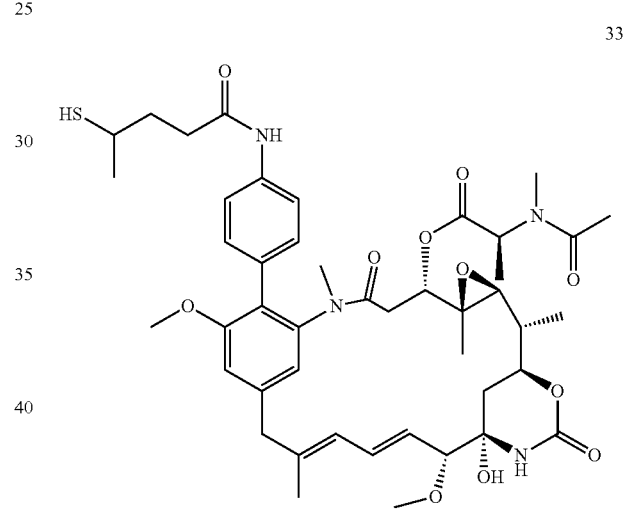

Step 1: Synthesis of Compound 34.

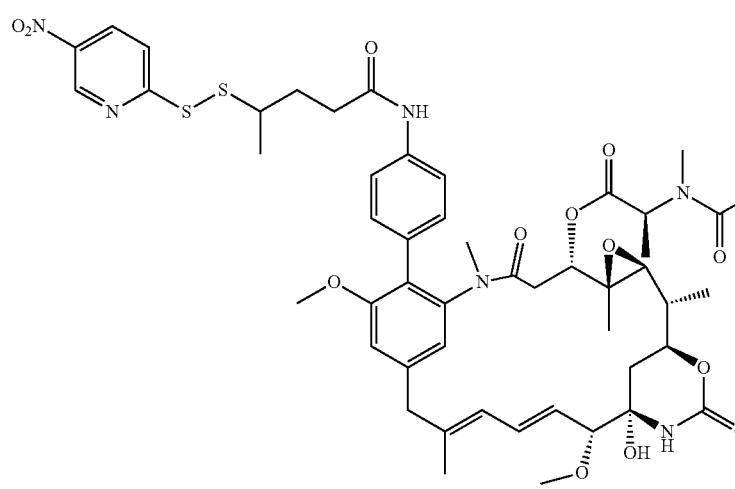

Compound 34 was synthesised in an analogous way to compound 8 of Example 5 using compound 32 instead of compound 4. Compound 34 was isolated as a pale yellow solid. LC/MS: (ES+) [M+H]+ (1019, 100%).

Step 2: Synthesis of Compound 33.

Compound 33 was synthesised in an analogous way to compound 6 of Example 5 using compound 34 instead of compound 8. Compound 33 was isolated as a white solid. $^1$H NMR (500 MHz; CDCl$_3$) δ 7.56-7.53 (m, 2H), 7.28 (dq, J=3.1, 1.0 Hz, 1H), 7.07-7.05 (m, 2H), 6.83 (s, 1H), 6.72-6.69 (m, 1H), 6.67 (d, J=0.3 Hz, 1H), 6.48-6.42 (m, 1H), 6.21 (s, 1H), 5.71-5.66 (m, 1H), 5.35-5.31 (m, 1H), 4.82-4.79 (m, 1H), 4.31-4.27 (m, 1H), 3.80 (s, 3H), 3.69 (d, J=12.7 Hz, 1H), 3.51 (d, J=9.0 Hz, 1H), 3.40-3.39 (m, 1H), 3.36 (s, 3H), 3.17-3.14 (m, 1H), 3.07 (d, J=9.8 Hz, 1H), 3.03-2.98 (m, 2H), 2.80 (s, 3H), 2.65 (s, 3H), 2.57-2.52 (m, 2H), 2.26-2.23 (m, 1H), 2.17-2.11 (m, 1H), 2.06 (s, 3H), 1.82-1.75 (m, 1H), 1.68 (s, 3H), 1.64-1.61 (m, 1H), 1.46-1.44 (m, 1H), 1.41-1.40 (m, 3H), 1.31-1.29 (m, 6H), 1.26-1.23 (m, 1H), 0.91 (s, 3H). LC/MS: (ES+) [M+H]+ (865, 100%).

Example 19: Preparation of Conjugation Reagent 35 Comprising a Maytansinoid Cytotoxic Payload A solution of 4-[2,2-bis[(p-tolylsulfonyl)-methyl]acetyl]benzoic acid (1.0 g, *Nature Protocols*, 2006, 1(54), 2241-2252) was added to N-hydroxybenzotriazole hydrate (306 mg) in anhydrous THF (10 mL) under a nitrogen atmosphere. The resulting solution was cooled to 0° C. and diisopropylcarbodiimide (310 µL) was added dropwise. The reaction mixture was stirred for 20 min at 0° C. before being warmed to room temperature. Additional THF (10 mL) was added to the reaction mixture after 1 h. After 18 h, the formed precipitate was filtered and washed with cold THF (2×5 mL) before being dried in vacuo. The solid was stirred with methanol (10 mL) for 1 h at room temperature, collected by filtration and washed sequentially with methanol (2×5 mL) and diethyl ether (5 mL). The solid was then dried in vacuo to give compound 36 as a white solid (1.1 g). LC/MS: (ES+) [M+H]+ (618, 100%).

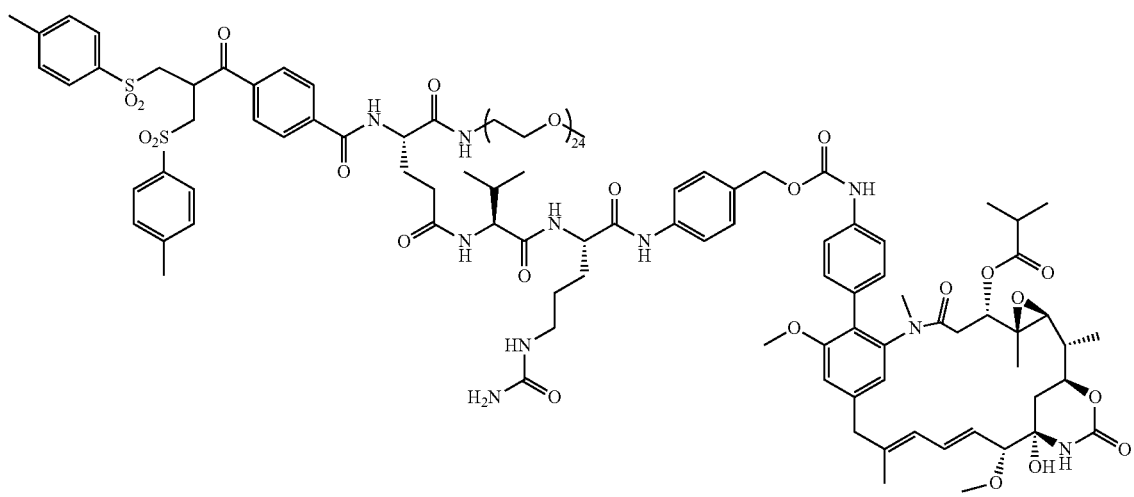

35

Step 1: Synthesis of Compound 36.

Step 2: Synthesis of Compound 37.

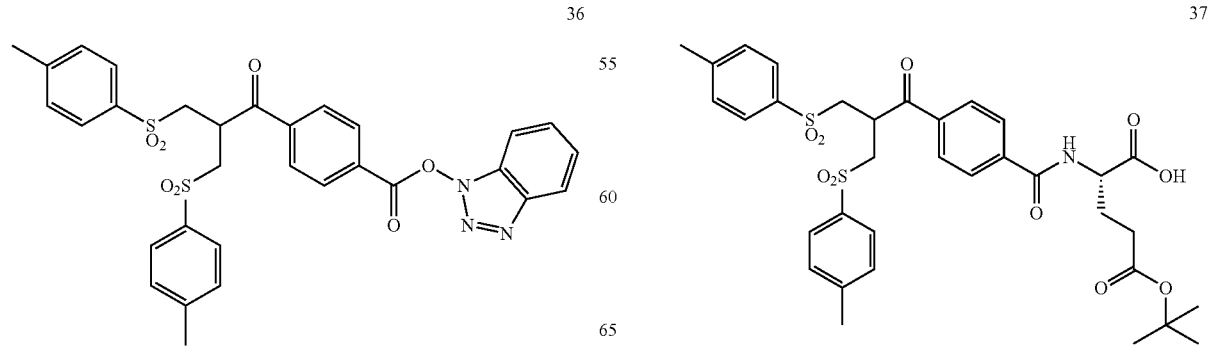

36

37

To a stirred suspension of L-Glutamic acid 5-tert-butyl ester (198 mg) in anhydrous DMF (20 mL) under a nitrogen atmosphere was added NMM (107 μL). The reaction mixture was cooled to 0° C. before compound 36 (603 mg) was added. The resulting suspension was stirred at 0° C. for 1 h, after which the reaction mixture was allowed to warm to room temperature. After 19 h, the resulting solution was concentrated in vacuo and purified by reverse phase C18-column chromatography, eluting with buffer A (v/v): water: 5% acetonitrile:0.1% formic acid and buffer B (v/v): acetonitrile:0.1% formic acid (100:0 v/v to 0:100 v/v). The organic solvent was removed in vacuo and the aqueous solvent removed by lyophilisation to give compound 37 as a white solid (198 mg). $^1$H NMR (400 MHz, CDCl$_3$) δ 7.98 (1H, d), 7.86 (2H), 7.71-7.65 (6H, m), 7.36 (4H, d), 4.68 (1H, ddd), 4.34 (1H, q), 3.62 (2H, ddd), 3.50 (2H, ddd), 2.69 (1H ddd), 2.55-2.45 (1H, m), 2.48 (6H, s), 2.34-2.16 (2H, m), 1.46 (9H, s). LC/MS: (ES+) [2M+H]$^+$ (1371, 70%), [2M+H-tBu]$^+$ (1315, 70%), [M+H-tBu]$^+$ (630, 100%).
Step 3: Synthesis of Compound 38.

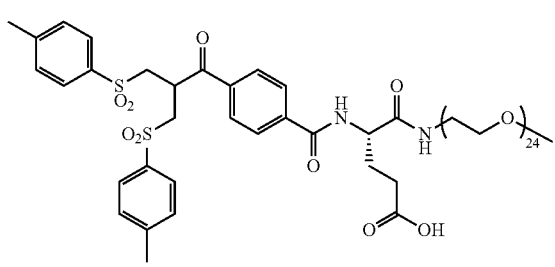

Compound 37 (50 mg) and (benzotriazol-1-yloxy)tris-(dimethylamino)phosphonium hexafluorophosphate (BOP) (40 mg) were dissolved in anhydrous DMF (3 mL), cooled to 0° C. and added to a solution of NH$_2$—PEG(24u)-OMe (99 mg) and NMM (10 μL) in anhydrous DMF (2 mL). The reaction mixture was stirred at 0° C. and after 4 h, additional amounts of BOP (10 mg) and NMM (2.5 μL) were added to the reaction mixture which was stirred for a further 15 min before being stored at −20° C. for 18 h. The reaction mixture was then concentrated in vacuo and purified by reverse phase C18-column chromatography, eluting with buffer A (v/v): water:5% acetonitrile:0.1% formic acid and buffer B (v/v): acetonitrile:0.1% formic acid (100:0 v/v to 0:100 v/v). The organic solvent was removed in vacuo and the aqueous solvent removed by lyophilisation to give bis-tolylsulfonyl-propanoyl-benzamide-L-Glu-[OtBu]-[PEG(24u)-OMe] as a colourless oil (128 mg). LC/MS: (ES+) [M+H]$^+$ (1757 Da, 100%), [M+2H]$^{2+}$ (879, 100%). Bis-tolylsulfonyl-propanoyl-benzamide-L-Glu-[OtBu]-[PEG(24u)-OMe] (126.5 mg) was dissolved in formic acid (2.5 mL) and stirred under a nitrogen atmosphere at room temperature. After 20 h, the reaction mixture was concentrated in vacuo and dried under high vacuum for 18 h to give compound 38 as a colourless oil (122 mg, assumed quantitative yield). LC/MS: (ES+) [M+H]$^+$ (1700, 100%).
Step 4: Synthesis of Compound 39.

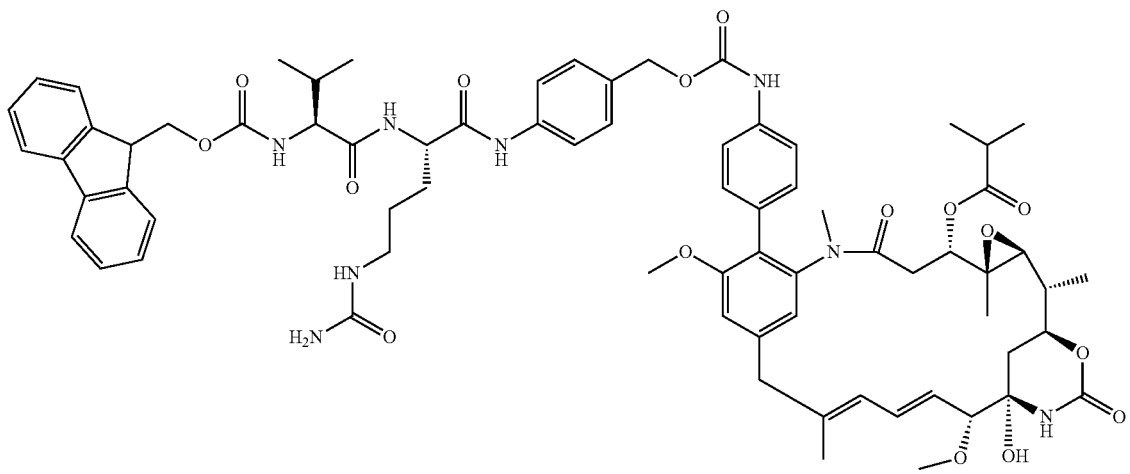

To a solution of compound 4 (50 mg), Fmoc-Val-Cit-PAB-PNP (Levena Biopharma, 85 mg), and 1-hydroxy-7-azabenzotriazole (HOAt) (11.5 mg) in DMF (3 mL), cooled to 0° C., was added DIPEA (40 μL). The reaction mixture was allowed to warm to room temperature and was stirred for 19 h. Additional HOAt (14 mg) was added and the mixture was stirred at room temperature for 9 h before storing at −20° C. for 72 h. Further HOAt (18 mg) was then added, and the mixture was stirred at room temperature for 6 h. The reaction mixture was then directly purified by reverse phase C18-column chromatography, eluting with buffer A (v/v): water: 0.05% trifluoroacetic acid and buffer B (v/v): acetonitrile:0.05% trifluoroacetic acid (100:0 v/v to 0:100 v/v). The product fractions were combined and concentrated under reduced pressure and the aqueous solution was extracted with ethyl acetate (100 mL). The layers were separated and the organic layer was washed with brine. The ethyl acetate layer was then separated, dried over sodium sulfate, filtered and concentrated in vacuo. The product was further purified by normal phase chromatography eluting with dichloromethane:methanol (100:0 v/v to 85:15 v/v). The solvent was removed in vacuo to give compound 39 as a white solid (44 mg). $^1$H NMR (500 MHz, CD$_3$OD) δ ppm 0.83-1.03 (m, 14H), 1.12-1.34 (m, 17H), 1.46-1.67 (m, 7H), 1.79 (s, 6H), 1.92 (br. s., 2H), 2.03-2.14 (m, 2H), 2.24 (d, J=14.17 Hz, 2H), 2.69 (s, 4H), 2.76 (dt, J=13.92, 6.72 Hz, 2H), 2.87 (d, J=9.77 Hz, 2H), 2.99-3.16 (m, 3H), 3.16-3.24 (m, 2H), 3.37 (d, J=6.35 Hz, 8H), 3.57-3.63 (m, 3H), 3.82 (s, 4H), 3.98 (d, J=7.33 Hz, 1H), 4.17-4.27 (m, 3H), 4.34-4.46 (m, 3H), 4.50-4.61 (m, 1H), 4.74 (d, J=9.77 Hz, 2H), 5.15 (s, 3H), 5.55 (dd, J=15.14, 8.79 Hz, 1H), 6.27 (d, J=10.75 Hz, 1H), 6.67 (dd, J=15.63, 11.23 Hz, 1H), 6.95 (s, 1H), 7.04-7.15 (m, 4H), 7.27-7.43 (m, 3H), 7.49 (d, J=7.82 Hz, 5H), 7.61 (d, J=8.3, 3H), 7.67 (t, J=8.3, 3H), 7.80 (d, J=7.33 Hz, 3H). LC/MS: (ES+) [M+H]$^+$ (1320, 100%).

Step 5: Synthesis of Compound 40.

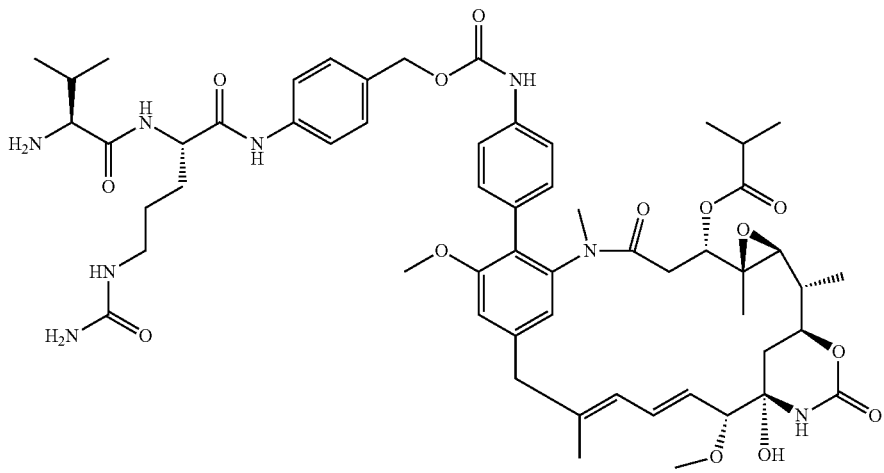

To a solution of compound 39 (52 mg) in anhydrous methanol (2 mL) under an argon atmosphere was added diethylamine (250 μL) and the mixture was stirred at room temperature for 1 h. Additional diethylamine (250 μL) was then added and the mixture was stirred at room temperature for a further 2 h. The reaction mixture was then concentrated under reduced pressure and purified by reverse phase C18-column chromatography eluting with buffer A (v/v): water: 0.1% acetic acid and buffer B (v/v): acetonitrile:0.1% acetic acid (100:0 v/v to 0:100 v/v). The desired fractions were combined and lyophilised to give compound 40 as a white solid (25 mg). $^1$H NMR (500 MHz; DMSO-d6) δ 10.23 (s, 1H), 9.80 (s, 1H), 8.69 (d, J=7.5 Hz, 1H), 8.10 (s, 3H), 7.63 (d, J=8.5 Hz, 2H), 7.48 (d, J=8.2 Hz, 2H), 7.39 (d, J=8.5 Hz, 2H), 7.13 (s, 1H), 7.08 (d, J=8.0 Hz, 1H), 6.87 (s, 1H), 6.81 (s, 1H), 6.62 (dd, J=15.2, 11.3 Hz, 1H), 6.22 (d, J=11.0 Hz, 1H), 6.08 (s, 1H), 5.89-5.86 (m, 1H), 5.43 (dd, J=15.2, 8.9 Hz, 1H), 5.11 (s, 2H), 4.59-4.52 (m, 2H), 4.11 (t, J=11.2 Hz, 1H), 3.76 (s, 3H), 3.68-3.66 (m, J=5.3 Hz, 1H), 3.54-3.51 (m, J=7.7 Hz, 2H), 3.25 (s, 3H), 3.06-3.05 (m, 1H), 2.98-2.97 (m, 1H), 2.85 (t, J=13.1 Hz, 1H), 2.70 (d, J=9.7 Hz, 1H), 2.66-2.63 (m, 1H), 2.22 (d, J=12.4 Hz, 1H), 2.09 (q, J=6.7 Hz, 1H), 1.76-1.73 (m, 1H), 1.69 (s, 3H), 1.66-1.62 (m, 1H), 1.51-1.38 (m, 4H), 1.15-1.13 (m, 5H), 1.10 (d, J=6.7 Hz, 3H), 0.97-0.94 (m, 9H). LC/MS: (ES+) [M+H]$^+$ (1098, 100%).

Step 6: Synthesis of Reagent 35.

To a solution of compound 38 (25.3 mg) in anhydrous DMF (400 μL) cooled to 0° C. was added HATU (5.7 mg). After stirring for 25 min, NMM (1.5 μL) was added and the solution was stirred for 15 min before allowing to warm to room temperature and stirring for a further 10 min. To a separate solution of compound 40 (15 mg) in anhydrous DMF (300 μL) was added NMM (1.5 μL) and the solution was stirred for 10 min at room temperature. The solutions were then combined and additional HATU (5.7 mg) and NMM (0.8 μL) were added to the reaction mixture. After stirring for 1 h at room temperature, the reaction mixture was concentrated in vacuo and purified by reverse phase C18-column chromatography eluting with buffer A (v/v): water: 0.05% trifluoroacetic acid and buffer B (v/v): acetonitrile:0.05% trifluoroacetic acid (95:5 v/v to 0:100 v/v). The organic solvent was removed in vacuo and the aqueous solvent removed by lyophilisation to give reagent 35 as a colourless solid (27.2 mg). LC/MS: (ES+) [M+2Na]$^{2+}$ (1412 Da, 40%), [M+H+Na]$^{2+}$ (1401, 50%), [M+2H+Na]$^{3+}$ (935, 80%), [M−H$_2$O+3H]$^{3+}$ (921, 100%).

Example 20: Preparation of Conjugation Reagent 41 Comprising a Maytansinoid Cytotoxic Payload

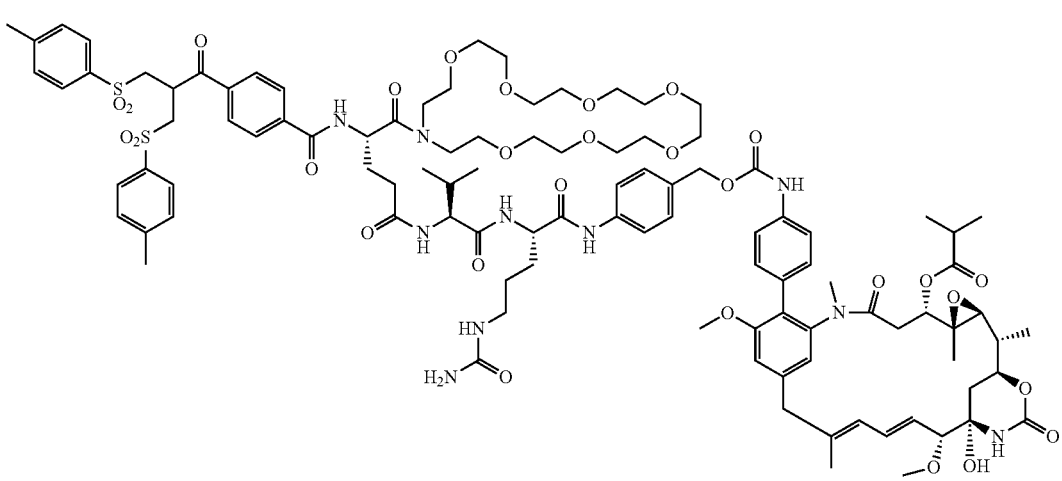

Step 1: Synthesis of Compound 42.

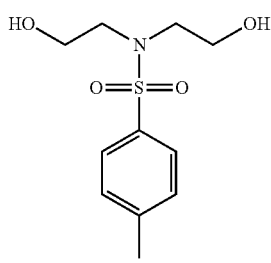

42

To a stirred solution of diethanolamine (2.5 g) and triethylamine (6.05 g) in dichloromethane (15 mL) was slowly added a solution of tosyl chloride (3.8 g) in dichloromethane (15 mL) at room temperature. After 2 h, water (25 mL) was added to the reaction mixture and the product was extracted with dichloromethane (5×30 mL). The combined organic extracts were dried over magnesium sulfate, the solution was then filtered and the volatiles removed in vacuo to yield compound 42 as a white solid (4.7 g). $^1$H NMR (400 MHz, CDCl$_3$) δ 7.68 (d, J=8.3 Hz, 2H), 7.30 (d, J=8.3 Hz, 2H), 3.84 (t, J=5.0 Hz, 4H), 3.56 (s, 2H), 3.24 (t, J=5.0 Hz, 4H), 2.41 (s, 3H). LC/MS: (ES+) [M+Na]$^+$ (282, 95%), [M+H]$^+$ (260, 100%).

Step 2: Synthesis of Compound 43.

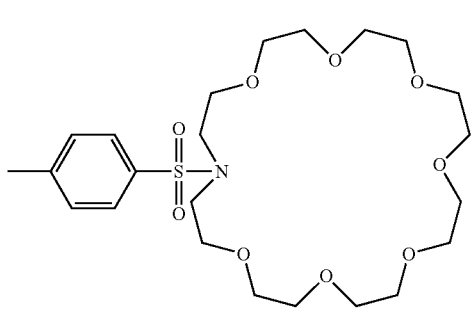

43

A solution of compound 42 (176 mg) in anhydrous THF (2 mL) was added dropwise over a period of 1 h to a solution of sodium hydride (80 mg, 60% dispersion in mineral oil) in anhydrous THF (8 mL) at room temperature. After stirring for 1 h, a solution of hexaethyleneglycol di-p-toluenesulfonate (400 mg) in anhydrous THF (2 mL) was added over a period of 2 h and the reaction mixture was stirred at room temperature for 72 h. Water (30 mL) was added and the THF was removed in vacuo. The aqueous solution was extracted with chloroform (4×25 mL), the organic phases were combined and dried over magnesium sulfate before the solution was filtered and concentrated in vacuo. The residue was then purified by reverse phase C18-column chromatography eluting with buffer A (v/v): water:5% acetonitrile:0.05% trifluoroacetic acid and buffer B (v/v):acetonitrile:0.05% trifluoroacetic acid (100:0 v/v to 0:100 v/v). The organic solvent was removed in vacuo and the aqueous solvent was removed by lyophilisation to give compound 43 as a colourless oil (78 mg). $^1$H NMR (400 MHz, CDCl$_3$) δ 7.68 (d, J=8.3 Hz, 2H), 7.26 (d, J=8.3 Hz, 4H), 3.67-3.58 (m, 24H), 3.58-3.53 (m, 4H), 3.38 (t, J=6.0 Hz, 4H), 2.40 (s, 3H). LC/MS: (ES+) [M+Na]$^+$ (528, 80%), [M+H]$^+$ (506, 50%).

Step 3: Synthesis of Compound 44.

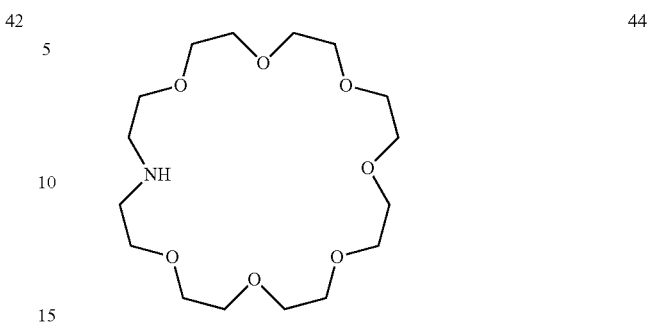

44

To a solution of compound 43 (78 mg) in anhydrous THF (6 mL) was added lithium aluminium hydride (1.13 mL, 1 M solution in THF) and the solution was heated at reflux for 16 h before the reaction mixture was cooled to 0° C. and quenched by the dropwise addition of water. The suspension was filtered and the precipitate washed with chloroform: ethanol (9:1 v/v, 5×6 mL). The filtrate and washings were combined and concentrated in vacuo to give compound 44 as a colourless oil (50 mg). LC/MS: (ES+) [M+Na]$^+$ (374, 70%), [M+H]$^+$ (352, 100%).

Step 4: Synthesis of Compound 45.

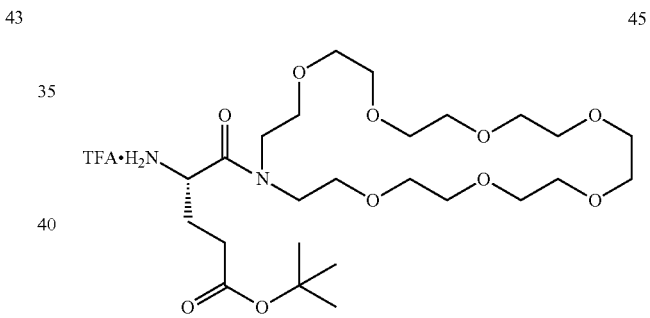

45

To a solution of Fmoc-Glu(OtBu)-OH (78 mg) in anhydrous DMF (500 μL) at 0° C. was added HATU (108 mg) and NMM (34 μL) and the mixture was stirred at 0° C. for 10 min. To this was added a solution of compound 44 (44 mg) in anhydrous DMF (500 μL) and the mixture was stirred at 0° C. under an argon atmosphere for 15 min. The reaction mixture was then concentrated in vacuo and the residue dissolved in anhydrous DMF (500 μL). Piperidine (70 μL) was added and the solution stirred for 90 min at room temperature. The reaction solution was concentrated in vacuo and purified by reverse phase C18-column chromatography, eluting with buffer A (v/v): water:5% acetonitrile: 0.05% trifluoroacetic acid and buffer B (v/v): acetonitrile: 0.05% trifluoroacetic acid (100:0 v/v to 0:100 v/v). The organic solvent was removed in vacuo and the aqueous solvent removed by lyophilisation to give compound 45 as an orange oil (44 mg). LC/MS: (ES+) [M+H]$^+$ (537, 45%).

Step 5: Synthesis of Compound 46.

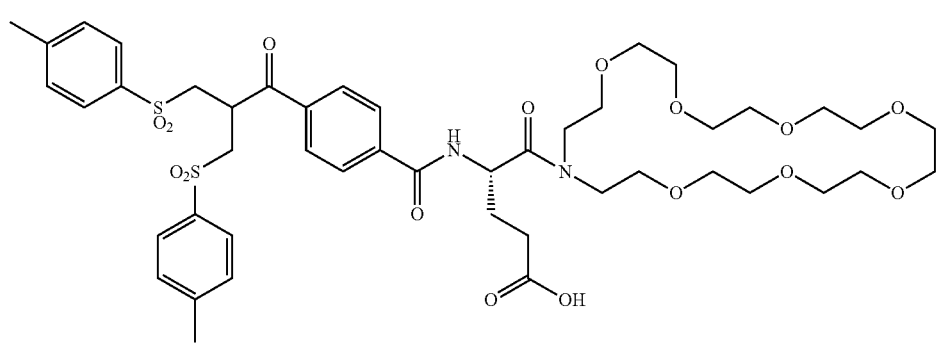

To a solution of 4-[2,2-bis[(p-tolylsulfonyl)-methyl]acetyl]benzoic acid (37.5 mg) in anhydrous DMF (500 μL) at 0° C. was added HATU (65 mg) and NMM (20 μL) and the mixture was stirred at 0° C. for 10 min. To this was added a solution of compound 45 (44.3 mg) in anhydrous DMF (500 μL) and the mixture was stirred at 0° C. under an argon atmosphere for 1 h. The reaction mixture was then concentrated in vacuo, the residue dissolved in DMF (1 mL) and purified by reverse phase C18-column chromatography, eluting with buffer A (v/v): water:0.05% trifluoroacetic acid and buffer B (v/v): acetonitrile:0.05% trifluoroacetic acid (60:40 v/v to 0:100 v/v). The solvent was removed by lyophilisation to give bis-tolylsulfonyl-propanoyl-benzamide-L-Glu-(OtBu)-aza-24-crown-8 as a white solid (28.5 mg). LC/MS: (ES+) [M+Na]$^+$ (1041, 20%), [M+H]$^+$ (1019, 5%). To a solution of bis-tolylsulfonyl-propanoyl-benzamide-L-Glu-(OtBu)-aza-24-crown-8 (26.5 mg) in anhydrous dichloromethane (1 mL) was added trifluoroacetic acid (500 μL) and the solution stirred at room temperature under an argon atmosphere for 1 h. The volatiles were removed in vacuo to give compound 46 as a white solid (assumed quantitative yield). LC/MS: (ES+) [M+Na]$^+$ (985, 35%), [M+H]$^+$ (963, 30%).

Step 6: Synthesis of Reagent 41.

To a solution of compound 46 (10.5 mg) in DMF (300 μL) cooled to 0° C. was added HATU (4 mg). After stirring for 20 min, NMM (1 μL) was added and the reaction solution was stirred for a further 30 min at 0° C. To a separate solution of compound 40 (10 mg) in DMF (200 μL) cooled to 0° C. was added NMM (1 μL) and the solution was stirred for 40 min. The solutions were then combined before additional quantities of HATU (4 mg) and NMM (1 μL) were added and the reaction mixture was allowed to warm to room temperature and was stirred for 3.25 h. The reaction solution was then concentrated in vacuo and purified by reverse phase C18-column chromatography, eluting with buffer A (v/v): water:0.05% trifluoroacetic acid and buffer B (v/v): acetonitrile:0.05% trifluoroacetic acid (70:30 v/v to 0:100 v/v). The organic solvent was removed in vacuo and the aqueous solvent removed by lyophilisation to give reagent 41 as a white solid (8.2 mg). LC/MS: (ES+) [M+2Na]$^{2+}$ (1043, 30%), [M+Na+H]$^{2+}$ (1033, 60%), [M+2H]$^{2+}$ (1021, 100%), [M+3H]$^{3+}$ (682, 30%).

Example 21: Preparation of Conjugation Reagent 47 Comprising a Maytansinoid Cytotoxic Payload

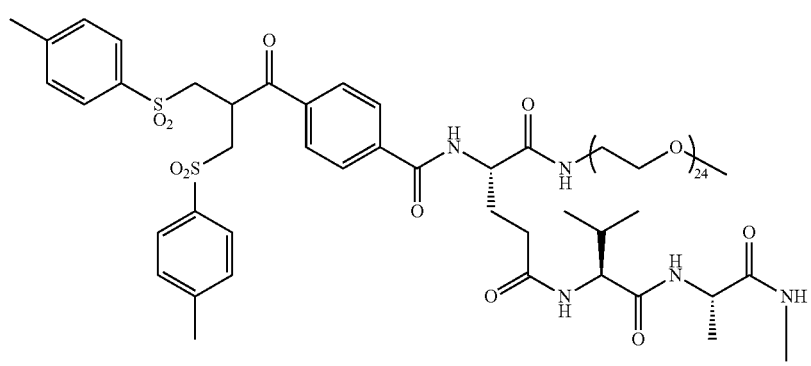

-continued

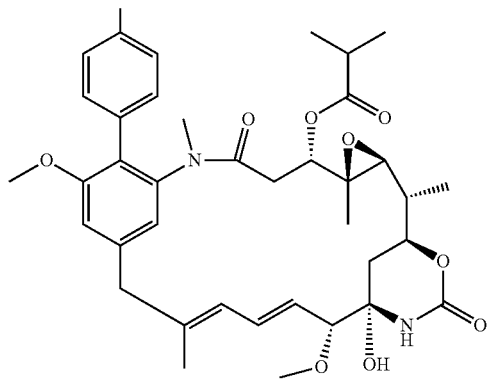

20

Step 1: Synthesis of Compound 48.

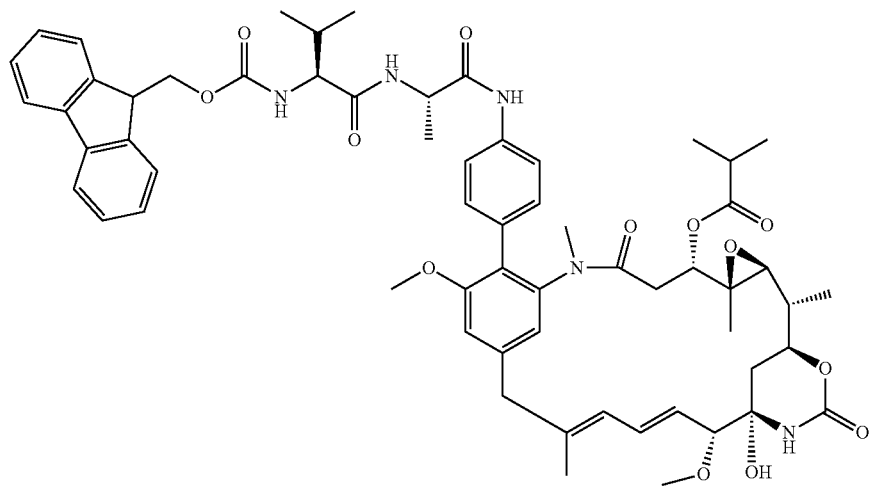

48

To a stirred solution of compound 4 (50 mg), Fmoc-Val-Ala-OH (Creagen, 67 mg) and HATU (85 mg) in anhydrous DMF (2 mL) at 0° C. was added DIPEA (50 μL). The solution was allowed to warm to room temperature and was stirred for 16 h. The reaction mixture was then directly purified by reverse phase C18-column chromatography, eluting with buffer A (v/v): water:0.1% acetic acid and buffer B (v/v): acetonitrile:0.1% acetic acid (100:0 v/v to 0:100 v/v) and the desired fractions lyophilised to give compound 48 as a white solid (57 mg). LC/MS: (ES+) [M+H]$^+$ (1084, 100%).

Step 2: Synthesis of Compound 49.

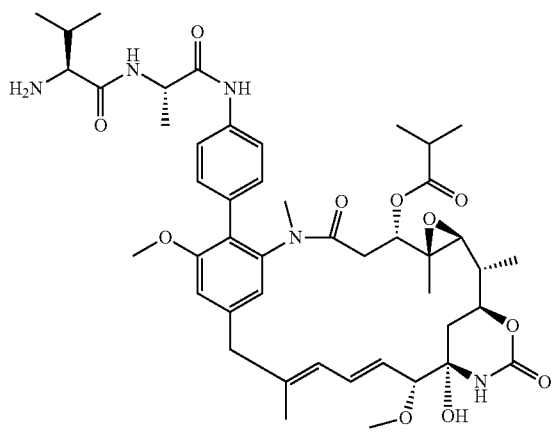

To a stirred solution of compound 48 (30 mg) in dichloromethane (2 mL) was added diethylamine (140 μL) and the reaction mixture was stirred at room temperature for 16 h before the solution was concentrated in vacuo. The residue was dissolved in DMF (5 mL) and purified by reverse phase C18-column chromatography, eluting with buffer A (v/v): water:0.1% acetic acid and buffer B (v/v): acetonitrile:0.1% acetic acid (100:0 v/v to 0:100 v/v). The desired fractions were combined and lyophilised to give compound 49 as a white solid (20 mg). LC/MS: (ES+) [M+H]+ (862, 100%).

Step 3: Synthesis of Reagent 47.

To a solution of compound 38 (15.6 mg), compound 49 (8 mg) and HATU (6.6 mg) in DMF (2 mL) at 0° C. was added NMM (30 μL) and the mixture was stirred at 0° C. for 90 min. The reaction mixture was then directly purified by reverse phase C18-column chromatography, eluting with buffer A (v/v): water:0.1% acetic acid and buffer B (v/v): acetonitrile:0.1% acetic acid (100:0 v/v to 0:100 v/v). The desired fractions were combined and lyophilised to give reagent 47 as a white solid (15 mg). 1H NMR (500 MHz; DMSO-d6) δ 9.99 (s, 0.5H), 9.92 (s, 0.5H), 8.73 (dd, J=7.2, 5.1 Hz, 1H), 8.40-8.39 (m, 0.5H), 8.25 (d, J=6.5 Hz, 0.5H), 8.05-8.01 (m, 1H), 7.97-7.87 (m, 2H), 7.67-7.51 (m, 6H), 7.46-7.44 (m, 3H), 7.13-7.09 (m, 2H), 6.86 (s, 1H), 6.81 (s, 1H), 6.65-6.60 (m, 1H), 6.52 (s, 1H), 6.23-6.21 (m, 1H), 5.87 (s, 1H), 5.42 (dd, J=15.2, 8.9 Hz, 1H), 4.59-4.57 (m, 1H), 4.46-1.39 (m, 2H), 4.27-4.17 (m, 1H), 4.13-4.09 (m, 1H), 4.01-3.98 (m, 1H), 3.84-3.80 (m, 2H), 3.75-3.71 (m, 6H), 3.51 (s, 96H), 3.44-3.42 (m, 5H), 3.38-3.36 (m, 1H), 3.25 (d, J=4.0 Hz, 6H), 2.89-2.83 (m, 1H), 2.70 (d, J=9.4 Hz, 1H), 2.46 (s, 6H), 2.40-2.22 (m, 4H), 2.08-1.90 (m, 3H), 1.69 (s, 3H), 1.51-1.45 (m, 2H), 1.40-1.38 (m, 1H), 1.33-1.31 (m, 4H), 1.14 (d, J=7.1 Hz, 6H), 1.10 (d, J=6.6 Hz, 4H), 0.93 (s, 3H), 0.90-0.84 (m, 6H). LC/MS: (ES+) [M+2H]2+ (1272, 30%), [M+3H]3+ (848, 100%).

Example 22: Preparation of Conjugation Reagent 50 Comprising a Maytansinoid Cytotoxic Payload

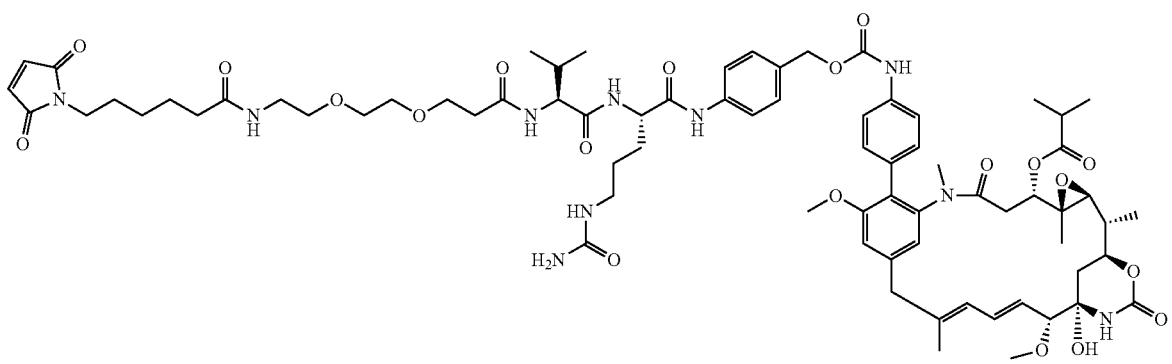

Step 1: Synthesis of Compound 51.

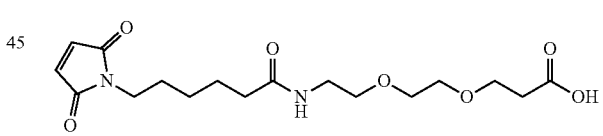

To a stirred suspension of amino-PEG(2u)-acid (50 mg) and 6-maleimidohexanoic acid N-hydroxysuccinimide ester (60 mg) in anhydrous DMF (2 mL) was added DIPEA (80 μL) and the reaction mixture was stirred at room temperature for 2 h. The mixture was then directly purified by reverse phase C-18 column chromatography eluting with buffer A (v/v): water:0.1% acetic acid and buffer B (v/v): acetonitrile: 0.1% acetic acid (100:0 v/v to 0:100 v/v). The desired fractions were combined and lyophilised to give compound 51 as a white solid (43 mg). 1H NMR (500 MHz; DMSO-d6) δ 7.83-7.80 (m, 1H), 7.02 (s, 2H), 3.61 (t, J=6.4 Hz, 3H), 3.41-3.36 (m, 6H), 3.34-3.33 (m, 1H), 3.18 (q, J=5.8 Hz, 3H), 2.45 (t, J=6.3 Hz, 2H), 2.05 (t, J=7.4 Hz, 2H), 1.48 (dt, J=14.9, 7.4 Hz, 4H), 1.23-1.13 (m, 2H). LC/MS: (ES+) [M+H]+ (371, 100%).

Step 2: Synthesis of Reagent 50.

To a solution of compound 40 (12 mg), compound 51 (5.6 mg) and HATU (8.2 mg) in DMF (1.5 mL) cooled to 0° C.

was added NMM (20 μL) and the mixture was stirred at 0° C. for 2.5 h. The reaction mixture was then purified directly by reverse phase C-18 column chromatography eluting with buffer A (v/v): water:0.1% acetic acid and buffer B (v/v): acetonitrile:0.1% acetic acid (100:0 v/v to 0:100 v/v). The desired fractions were combined and lyophilised to give reagent 50 as a white solid (12 mg). $^1$H NMR (500 MHz; DMSO-$d_6$) δ 10.06 (s, 1H), 9.79-9.78 (m, 1H), 8.18 (d, J=7.3 Hz, 1H), 7.91 (d, J=8.8 Hz, 1H), 7.82-7.80 (m, 1H), 7.63 (d, J=8.5 Hz, 2H), 7.47 (d, J=8.5 Hz, 2H), 7.37 (d, J=8.5 Hz, 2H), 7.13 (s, 1H), 7.08 (d, J=8.0 Hz, 2H), 7.00 (s, 2H), 6.86 (s, 1H), 6.80 (s, 1H), 6.62 (dd, J=15.3, 11.2 Hz, 1H), 6.21 (d, J=11.1 Hz, 1H), 6.04-6.01 (m, 1H), 5.87 (s, 1H), 5.45-5.40 (m, 3H), 5.10 (s, 2H), 4.59-4.56 (m, 1H), 4.41-4.37 (m, 1H), 4.25-4.22 (m, 1H), 4.13-4.09 (m, 1H), 3.76 (s, 3H), 3.63-3.59 (m, 2H), 3.54-3.50 (m, 2H), 3.48-3.46 (m, 4H), 3.38-3.36 (m, 4H), 3.25 (s, 3H), 3.17 (q, J=5.8 Hz, 2H), 3.04-2.92 (m, 2H), 2.88-2.83 (m, 1H), 2.70 (d, J=9.7 Hz, 1H), 2.67-2.61 (m, 1H), 2.47-2.45 (m, 1H), 2.41-2.36 (m, 1H), 2.23 (dd, J=13.0, 0.8 Hz, 1H), 2.04 (t, J=7.4 Hz, 2H), 2.01-1.94 (m, 1H), 1.73-1.65 (m, 5H), 1.63-1.58 (m, 1H), 1.51-1.42 (m, 7H), 1.40-1.35 (m, 2H), 1.20-1.12 (m, 8H), 1.10 (d, J=6.6 Hz, 3H), 0.94 (s, 3H), 0.87 (d, J=6.7 Hz, 3H), 0.83 (d, J=6.8 Hz, 3H). LC/MS: (ES+) [M+H]$^+$ (1449, 100%).

Example 23: Preparation of a Series of Maytansinoid Compounds

A series of maytansinoid compounds of the general formula (XV) were prepared using an analogous procedure to that described in Example 3, by replacing 4-aminophenylboronic acid with a range of aryl boron reagents to produce compounds 52, 53, 54, 55, 56, 57, 58, 59, 60, 61, 62, 63 and 64. The compound structures and modifications to the synthetic protocol described in Example 3, are shown in Table 5.

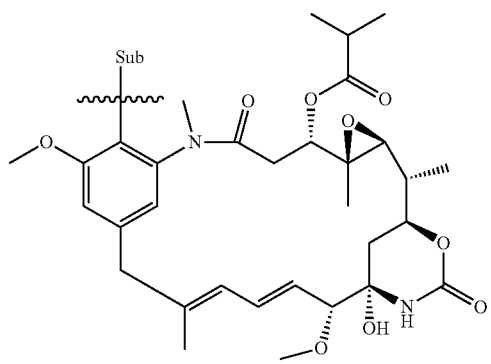

(XV)

TABLE 5

| Compound No. | Sub group | Aryl boron reagent (molar equivalents*) | Catalyst (molar equivalents*) | Reaction time (h) |
|---|---|---|---|---|
| 52 | H$_2$N-phenyl- | 3-aminophenylboronic acid monohydrate (1.5) | SPhos Pd G3 (0.025) | 18 |
| 53*** | 3-methoxy-4-aminophenyl- | 4-amino-2-methoxyphenylboronic acid pinacol ester (2.0) | SPhos Pd G3 (0.025) | 8 |
| 54 | 3-nitro-4-aminophenyl- | 4-amino-3-nitrophenylboronic acid pinacol ester (1.2) | XPhos Pd G3 (0.025) | 18 |

TABLE 5-continued

| Compound No. | Sub group | Aryl boron reagent (molar equivalents*) | Catalyst (molar equivalents*) | Reaction time (h) |
|---|---|---|---|---|
| 55 | 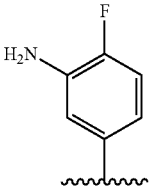 | 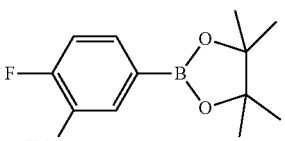
3-amino-4-fluorophenylboronic acid pinacol ester (1.2) | XPhos Pd G3 (0.025) | 18 |
| 56 | 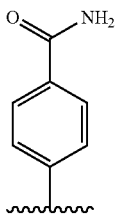 [SMILES: *c1ccc(C(N)=O)cc1] | 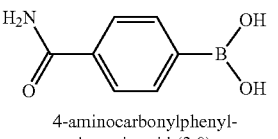
4-aminocarbonylphenyl-boronic acid (2.0) | SPhos Pd G3 (0.125) | 18 |
| 57 | 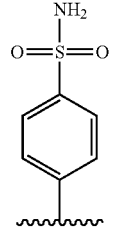 | 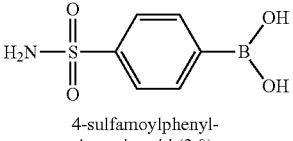
4-sulfamoylphenyl-boronic acid (2.0) | SPhos Pd G3 (0.125) + XPhos Pd G3 (0.025) | 18 |
| 58 | 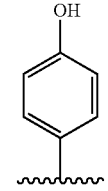 | 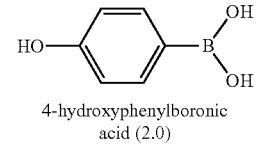
4-hydroxyphenylboronic acid (2.0) | SPhos Pd G3 (0.025) | 18 |
| 59 | 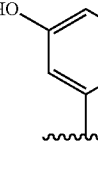 | 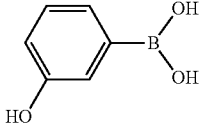
3-hydroxyphenylboronic acid (2.0) | SPhos Pd G3 (0.125) | 18 |
| 60 | 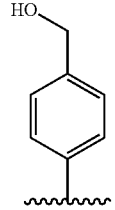 | 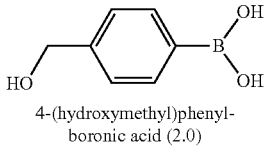
4-(hydroxymethyl)phenyl-boronic acid (2.0) | SPhos Pd G3 (0.125) | 18 |
| 61 | 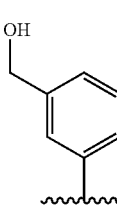 | 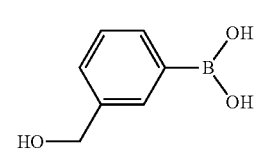
3-(hydroxymethyl)phenyl-boronic acid (1.2) | XPhos Pd G3 (0.025) | 18 |

TABLE 5-continued

| Compound No. | Sub group | Aryl boron reagent (molar equivalents*) | Catalyst (molar equivalents*) | Reaction time (h) |
|---|---|---|---|---|
| 62 | (2-chloro-4-hydroxyphenyl sub group) | 3-chloro-4-hydroxyphenylboronic acid (1.0) | SPhos Pd G3 (0.125) | 18 |
| 63*** | (2-cyano-4-aminophenyl sub group) | 2-cyano-4-aminophenylboronic acid pinacol ester (2.0) | XPhos Pd G3 (0.125) | 5 |
| 64*** | (2-methoxycarbonyl-4-aminophenyl sub group) | 2-methoxycarbonyl-4-aminophenylboronic acid pinacol ester (1.2) | SPhos Pd G3 (0.14) + XPhos Pd G3 (0.12) | 23 |

*molar equivalents relative to 1 molar equivalent of AP3.
**3 molar equivalents of tripotassium phosphate were used to prepare compound 52. 4 molar equivalents of tripotassium phosphate were used to prepare compounds 53-64.
***product isolated as a mixture of atropisomers.

Characterisation data for compound 52: $^1$H NMR (500 MHz; CDCl$_3$) δ 7.21-7.15 (m, 1H), 6.85 (d, J=2.2 Hz, 2H), 6.68-6.65 (m, 1H), 6.51-6.45 (m, 3H), 6.22-6.17 (m, 2H), 5.49-5.44 (m, 1H), 4.84-4.81 (m, 1H), 4.31-4.27 (m, 1H), 3.82 (s, 3H), 3.57-3.50 (m, 2H), 3.37 (s, 3H), 3.29-3.24 (m, 1H), 3.02-2.90 (m, 3H), 2.73 (s, 3H), 2.69-2.61 (m, 1H), 2.27-2.22 (m, 1H), 1.75 (s, 3H), 1.69-1.66 (m, 1H), 1.50-1.48 (m, 1H), 1.30 (d, J=6.3 Hz, 3H), 1.26 (d, J=7.1 Hz, 3H), 1.24-1.23 (m, 1H), 1.20 (d, J=6.7 Hz, 3H), 0.93 (s, 3H). LC/MS: (ES+) [M+H]$^+$ (692, 100%).

Characterisation data for compound 53: LC/MS: (ES+) [M+H]$^+$ (722, 100%).

Characterisation data for compound 54: $^1$H NMR (500 MHz; CDCl$_3$) δ 7.98 (s, 1H), 7.08 (dd, J=8.5, 1.5 Hz, 1H), 6.89 (s, 1H), 6.86 (s, 1H), 6.82 (d, J=8.6 Hz, 1H), 6.48 (dd, J=15.4, 11.0 Hz, 1H), 6.21-6.16 (m, 4H), 5.47 (dd, J=15.4, 9.0 Hz, 1H), 4.84 (dd, J=11.9, 2.8 Hz, 1H), 4.30 (t, J=10.6 Hz, 1H), 3.84 (s, 3H), 3.57 (d, J=12.9 Hz, 1H), 3.52 (d, J=9.0 Hz, 1H), 3.37 (s, 3H), 3.27 (d, J=13.0 Hz, 1H), 3.00 (d, J=9.7 Hz, 1H), 2.94 (t, J=12.9 Hz, 1H), 2.74 (s, 3H), 2.63 (dt, J=13.9, 6.9 Hz, 1H), 2.25 (dd, J=13.8, 2.7 Hz, 1H), 1.75 (s, 3H), 1.67 (d, J=13.5 Hz, 1H), 1.53-1.47 (m, 1H), 1.30 (d, J=6.3 Hz, 3H), 1.26 (d, J=7.1 Hz, 3H), 1.25-1.24 (m, 1H), 1.20 (d, J=6.7 Hz, 3H), 0.94 (s, 3H). LC/MS: (ES+) [M+H]$^+$ (737, 100%).

Characterisation data for compound 55: $^1$H NMR (300 MHz; CDCl$_3$) δ 6.99 (dd, J=10.9, 8.4 Hz, 1H), 6.85 (d, J=2.7 Hz, 2H), 6.54-6.47 (m, 2H), 6.44-6.39 (m, 1H), 6.21-6.16 (m, 2H), 5.47 (dd, J=15.4, 9.1 Hz, 1H), 4.83 (dd, J=11.9, 2.9 Hz, 1H), 4.33-4.25 (m, 1H), 3.82 (s, 3H), 3.73 (s, 2H), 3.58-3.50 (m, 2H), 3.37 (s, 3H), 3.25 (d, J=13.1 Hz, 1H), 3.02-2.86 (m, 2H), 2.73 (s, 3H), 2.67-2.58 (m, 1H), 2.22 (dd, J=13.8, 2.7 Hz, 1H), 1.74 (s, 3H), 1.67 (d, J=13.7 Hz, 1H), 1.53-1.46 (m, 1H), 1.30 (d, J=6.2 Hz, 3H), 1.26 (d, J=7.0 Hz, 3H), 1.25-1.23 (m, 1H), 1.20 (d, J=6.7 Hz, 3H), 0.93 (s, 3H). LC/MS: (ES+) [2M+H]$^+$ (1420, 100%), [M+H]$^+$ (710, 70%).

Characterisation data for compound 56: $^1$H NMR (500 MHz; CDCl$_3$) δ 7.83 (d, J=8.3 Hz, 2H), 7.23-7.21 (m, 2H), 6.89 (d, J=10.0 Hz, 2H), 6.49 (dd, J=15.5, 11.0 Hz, 1H), 6.21-6.19 (m, 2H), 5.48 (dd, J=15.5, 9.1 Hz, 1H), 4.84 (dd, J=11.9, 2.9 Hz, 1H), 4.32-4.27 (m, 1H), 3.82 (s, 3H), 3.58 (d, J=12.7 Hz, 1H), 3.52 (d, J=9.0 Hz, 1H), 3.37 (s, 3H), 3.30-3.27 (m, 1H), 3.02-2.94 (m, 2H), 2.66 (s, 3H), 2.64-2.60 (m, 1H), 2.25 (dd, J=13.6, 2.8 Hz, 1H), 1.76 (s, 3H), 1.69-1.67 (m, 1H), 1.53-1.48 (m, 1H), 1.31 (d, J=6.4 Hz, 3H), 1.26 (d, J=7.2 Hz, 4H), 1.25-1.24 (m, 1H), 1.20 (d, J=6.8 Hz, 3H), 0.95 (s, 3H). LC/MS: (ES+) [M+H]$^+$ (720, 100%).

Characterisation data for compound 57: $^1$H NMR (500 MHz; CDCl$_3$) δ 7.94 (d, J=8.7 Hz, 2H), 6.89 (d, J=9.0 Hz, 2H), 6.48 (dd, J=15.3, 11.0 Hz, 1H), 6.21-6.18 (m, 2H), 5.47 (dd, J=15.3, 9.0 Hz, 1H), 4.85 (s, 2H), 4.82 (dd, J=11.9, 2.9

Hz, 1H), 4.31-4.27 (m, 1H), 3.81 (s, 3H), 3.57 (d, J=12.8 Hz, 1H), 3.52 (d, J=8.9 Hz, 1H), 3.37 (s, 3H), 3.28 (d, J=12.7 Hz, 1H), 3.01-2.91 (m, 2H), 2.67 (s, 3H), 2.65-2.59 (m, 1H), 2.23 (dd, J=13.8, 2.8 Hz, 1H), 1.75 (s, 3H), 1.66 (dd, J=13.7, 1.5 Hz, 1H), 1.52-1.47 (m, 1H), 1.30 (d, J=6.3 Hz, 3H), 1.25 (d, J=7.2 Hz, 3H), 1.25-1.23 (m, 1H), 1.20 (d, J=6.7 Hz, 3H), 0.94 (s, 3H). LC/MS: (ES+) [M+H]$^+$ (756, 100%).

Characterisation data for compound 58: $^1$H NMR (500 MHz; CDCl$_3$) δ 6.96 (d, J=7.9 Hz, 2H), 6.86 (d, J=10.4 Hz, 2H), 6.81 (d, J=8.6 Hz, 2H), 6.49 (dd, J=15.4, 11.1 Hz, 1H), 6.24 (s, 1H), 6.19 (d, J=11.1 Hz, 1H), 5.47 (dd, J=15.5, 9.0 Hz, 1H), 4.83 (dd, J=11.9, 2.8 Hz, 1H), 4.32-4.28 (m, 1H), 3.82 (s, 3H), 3.56 (d, J=13.0 Hz, 1H), 3.52 (d, J=9.0 Hz, 1H), 3.37 (s, 3H), 3.26 (d, J=12.8 Hz, 1H), 3.02-2.96 (m, 2H), 2.67 (s, 3H), 2.64-2.60 (m, 1H), 2.27 (dd, J=13.6, 2.3 Hz, 1H), 1.75 (s, 3H), 1.68 (d, J=13.5 Hz, 1H), 1.53-1.48 (m, 1H), 1.30 (d, J=6.3 Hz, 3H), 1.26 (d, J=7.2 Hz, 3H), 1.25-1.24 (m, 1H), 1.20 (d, J=6.7 Hz, 3H), 0.94 (s, 3H). LC/MS: (ES+) [M+H]$^+$ (693, 100%).

Characterisation data for compound 59: $^1$H NMR (300 MHz; CDCl$_3$) δ 7.22 (d, J=7.9 Hz, 1H), 6.86 (s, 2H), 6.83-6.80 (m, 1H), 6.70 (d, J=7.6 Hz, 1H), 6.62 (s, 1H), 6.48 (dd, J=15.3, 11.0 Hz, 1H), 6.39 (s, 1H), 6.19 (d, J=10.7 Hz, 1H), 5.51 (dd, J=15.3, 9.0 Hz, 1H), 4.86 (dd, J=11.9, 2.5 Hz, 1H), 4.44-4.36 (m, 1H), 3.82 (s, 3H), 3.56 (d, J=13.0 Hz, 1H), 3.49 (d, J=9.0 Hz, 1H), 3.36 (s, 3H), 3.24 (d, J=13.1 Hz, 1H), 3.00 (d, J=9.6 Hz, 1H), 2.91 (t, J=13.0 Hz, 1H), 2.65 (s, 2H), 2.63-2.58 (m, 1H), 2.41-2.35 (m, 1H), 1.74 (s, 3H), 1.71-1.65 (m, 1H), 1.57-1.45 (m, 1H), 1.31 (d, J=6.3 Hz, 3H), 1.28-1.27 (m, 1H), 1.23 (d, J=7.1 Hz, 3H), 1.19 (d, J=6.7 Hz, 3H), 0.95 (s, 3H). LC/MS: (ES+) [M+H]$^+$ (693, 100%).

Characterisation data for compound 60: $^1$H NMR (300 MHz; CDCl$_3$) δ 7.39 (d, J=8.0 Hz, 2H), 7.11 (d, J=7.8 Hz, 2H), 6.88 (d, J=4.2 Hz, 2H), 6.49 (dd, J=15.4, 10.9 Hz, 1H), 6.22-6.17 (m, 2H), 5.47 (dd, J=15.3, 9.2 Hz, 1H), 4.82 (dd, J=12.0, 3.0 Hz, 1H), 4.73 (s, 2H), 4.33-4.26 (m, 1H), 3.82 (s, 3H), 3.57 (d, J=12.9 Hz, 1H), 3.53-3.50 (m, 1H), 3.37 (s, 3H), 3.27 (d, J=13.3 Hz, 1H), 3.03-2.91 (m, 3H), 2.67 (s, 3H), 2.67-2.58 (m, 1H), 2.23 (dd, J=13.8, 3.0 Hz, 1H), 1.75 (d, J=5.5 Hz, 3H), 1.70-1.65 (m, 1H), 1.55-1.46 (m, 1H), 1.31 (d, J=6.3 Hz, 3H), 1.26-1.24 (m, 1H), 1.26 (d, J=7.2 Hz, 3H), 1.20 (d, J=6.7 Hz, 3H), 0.94 (s, 3H). LC/MS: (ES+) [M+H]$^+$ (707, 100%).

Characterisation data for compound 61: $^1$H NMR (300 MHz; CDCl$_3$) δ 7.40-7.30 (m, 2H), 7.13 (s, 1H), 7.07-7.04 (m, 1H), 6.88 (d, J=6.2 Hz, 2H), 6.49 (dd, J=15.4, 11.0 Hz, 1H), 6.21-6.17 (m, 2H), 5.47 (dd, J=15.2, 9.0 Hz, 1H), 4.84-4.80 (m, 1H), 4.70 (s, 2H), 4.33-4.25 (m, 1H), 3.82 (s, 3H), 3.57 (d, J=12.7 Hz, 1H), 3.52 (d, J=9.0 Hz, 1H), 3.37 (s, 3H), 3.27 (d, J=12.6 Hz, 1H), 3.04-2.91 (m, 3H), 2.66 (s, 3H), 2.63-2.58 (m, 1H), 2.28-2.22 (m, 1H), 1.86-1.82 (m, 1H), 1.75 (s, 3H), 1.70-1.65 (m, 1H), 1.52-1.47 (m, 1H), 1.30 (d, J=6.2 Hz, 3H), 1.27-1.24 (m, 1H), 1.26 (d, J=7.0 Hz, 3H), 1.20 (d, J=6.7 Hz, 3H), 0.95 (s, 3H). LC/MS: (ES+) [M+H]$^+$ (707, 100%).

Characterisation data for compound 62: $^1$H NMR (500 MHz; CDCl$_3$) δ 7.11 (s, 1H), 7.00 (d, J=8.4 Hz, 1H), 6.89-6.85 (m, J=10.7 Hz, 3H), 6.48 (dd, J=15.4, 11.0 Hz, 1H), 6.23 (s, 1H), 6.18 (d, J=11.0 Hz, 1H), 6.09 (s, 1H), 5.47 (dd, J=15.4, 9.0 Hz, 1H), 4.83 (dd, J=11.9, 2.9 Hz, 1H), 4.32-4.27 (m, 1H), 3.83 (s, 3H), 3.56 (d, J=12.9 Hz, 1H), 3.52 (d, J=9.0 Hz, 1H), 3.37 (s, 3H), 3.26 (d, J=12.9 Hz, 1H), 3.11 (d, J=2.0 Hz, 1H), 3.00 (d, J=9.7 Hz, 1H), 2.94 (dd, J=13.7, 12.1 Hz, 1H), 2.71 (s, 3H), 2.65-2.59 (m, 1H), 2.24 (dd, J=13.8, 2.7 Hz, 1H), 1.74 (s, 3H), 1.67 (d, J=13.5 Hz, 1H), 1.52-1.46 (m, 1H), 1.30 (d, J=6.4 Hz, 3H), 1.26 (d, J=7.2 Hz, 3H), 1.27-1.25 (m, 1H), 1.20 (d, J=6.7 Hz, 3H), 0.94 (s, 3H). LC/MS: (ES+) [M+H]$^+$ (727, 100%).

Characterisation data for compound 63: $^1$H NMR (500 MHz; CDCl$_3$) δ 7.05 (d, J=8.3 Hz, 0.33H), 6.98 (d, 0.66H, J=2.4 Hz, 0.66H), 6.94-6.91 (m, 1H), 6.89-6.85 (m, 2.33H), 6.79 (d, J=8.3 Hz, 0.66H), 6.51-6.44 (m, 1H), 6.23-6.15 (m, 2H), 5.50-5.41 (m, 1H), 4.84 (dd, J=11.9, 3.0 Hz, 0.66H), 4.74 (dd, J=12.1, 3.1 Hz, 0.33H), 4.32-4.23 (m, 1H), 3.94-3.92 (m, 2H), 3.88 (s, 2H), 3.84 (s, 1H), 3.59-3.50 (m, 2H), 3.37 (s, 2H), 3.36 (s, 1H), 3.31-3.25 (m, 1H), 3.02-2.78 (m, 4H), 2.69 (s, 2H), 2.65-2.60 (m, 1H), 2.27-2.23 (m, 0.66H), 2.14-2.11 (m, 0.33H), 1.77 (s, 1H), 1.74 (s, 2H), 1.70-1.62 (m, 1H), 1.52-1.46 (m, 1H), 1.32-1.25 (m, 7H), 1.21-1.19 (m, 3H), 0.95 (s, 2H), 0.90 (s, 1H). LC/MS: (ES+) [M+H]$^+$ (717, 100%).

Characterisation data for compound 64: $^1$H NMR (500 MHz; CDCl$_3$) δ 7.30 (d, J=2.4 Hz, 0.2H), 7.24 (d, J=2.4 Hz, 0.8H), 6.94 (d, J=8.1 Hz, 0.2H), 6.90 (s, 0.8H), 6.83-6.79 (m, 2H), 6.74 (s, 1H), 6.71 (d, J=8.2 Hz, 1H), 6.51-6.46 (m, 1H), 6.22-6.15 (m, 2H), 5.49-5.41 (m, 1H), 4.86 (dd, J=11.8, 2.7 Hz, 0.8H), 4.68-4.65 (m, 0.2H), 4.33-4.24 (m, 1H), 3.85-3.81 (m, 2H), 3.76-3.73 (m, 3H), 3.68-3.66 (m, 3H), 3.59-3.49 (m, 2H), 3.37-3.36 (m, 3H), 3.28-3.22 (m, 1H), 3.11-3.02 (m, 2.4H), 2.93 (s, 0.6H), 2.91-2.85 (m, 0.6H), 2.70 (s, 2.4H), 2.67-2.60 (m, 1H), 2.29-2.26 (m, 0.8H), 1.80 (s, 0.6H), 1.78-1.74 (m, 0.2H), 1.73 (s, 2.4H), 1.72-1.63 (m, 1H), 1.54-1.46 (m, 1H), 1.32-1.30 (m, 3H), 1.28-1.24 (m, 4H), 1.21-1.18 (m, 3H), 0.97 (s, 2.4H), 0.91 (s, 0.6H). LC/MS: (ES+) [M+H]$^+$ (750, 100%).

Example 24: Preparation of Maytansinoid Compound 65

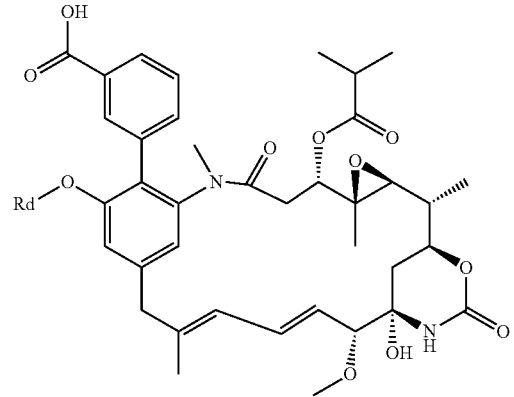

Compound 61 (36 mg), iron(III) nitrate nonahydrate (13 mg), TEMPO (4.8 mg), potassium chloride (6.2 mg) and 1,2-dichloroethane (2 mL) were sequentially added to a reaction vessel and the mixture was stirred under an oxygen atmosphere for 5 days. The reaction mixture was then concentrated in vacuo, the residue was dissolved in DMF (10 mL) and then purified by reverse phase C-18 column chromatography eluting with buffer A (v/v): water:0.1% acetic acid and buffer B (v/v): acetonitrile:0.1% acetic acid (100:0 v/v to 0:100 v/v). The desired fractions were combined and lyophilised to give compound 65 as a white solid (4.5 mg). $^1$H NMR (500 MHz; CD$_3$OD) δ 8.01 (d, J=7.4 Hz, 1H), 7.82-7.80 (m, 1H), 7.53-7.50 (m, 1H), 7.42-7.39 (m, 1H), 7.17 (s, 1H), 6.99 (s, 1H), 6.72-6.67 (m, 1H), 6.30 (d, J=11.0 Hz, 1H), 5.59-5.51 (m, 1H), 4.75 (d, J=11.7 Hz, 1H), 4.27-4.22 (m, 1H), 3.85 (s, 3H), 3.65-3.61 (m, 3H), 3.39 (s, 3H), 3.11-3.06 (m, 1H), 2.88 (d, J=9.4 Hz, 1H), 2.80-2.74 (m, 1H), 2.67 (s, 3H), 2.32-2.29 (m, 1H), 1.81 (s, 3H), 1.66-1.57 (m, 3H), 1.31-1.27 (m, 7H), 1.23 (d, J=6.5 Hz, 3H), 1.04 (s, 3H). LC/MS: (ES+) [M+H]$^+$ (721, 100%).

Example 25: Preparation of Conjugation Reagent 66 Comprising a Maytansinoid Cytotoxic Payload

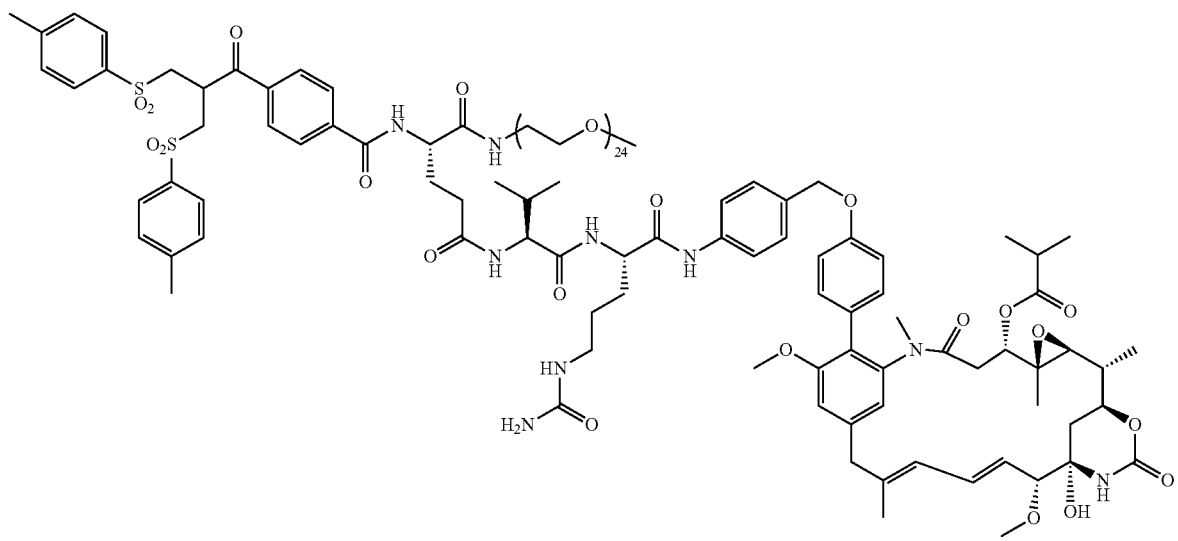

66

Step 1: Synthesis of Compound 67.

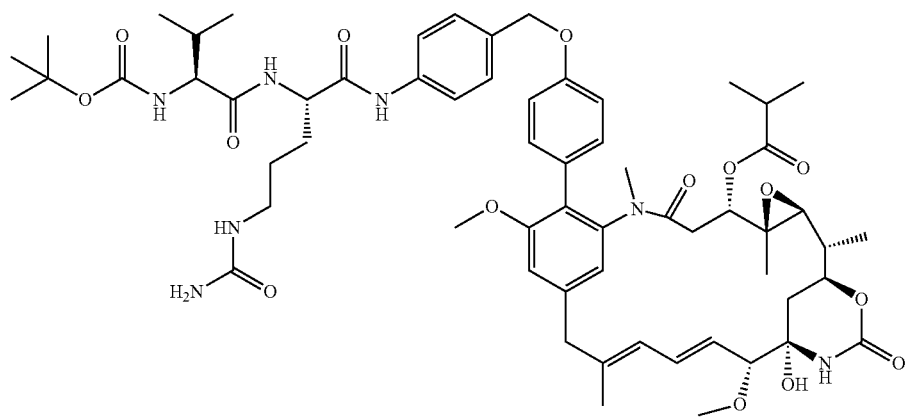

67

To a stirred solution of compound 58 (328 mg), Boc-Val-Cit-PAB (BroadPharm, 688 mg) and tri-n-butylphosphine (700 μL) in DMF (15 mL) at 0° C. was slowly added diisopropyl azodicarboxylate (560 μL). The mixture was allowed to gradually warm to room temperature and was stirred for 2.5 h. The reaction mixture was then directly purified by reverse phase C-18 column chromatography eluting with buffer A (v/v): water:0.1% acetic acid and buffer B (v/v): acetonitrile:0.1% acetic acid (100:0 v/v to 0:100 v/v). The desired fractions were combined and lyophilised to give compound 67 as a pale yellow solid (92 mg). LC/MS: (ES+) [M+H]$^+$ (1154, 100%).

Step 2: Synthesis of Compound 68.

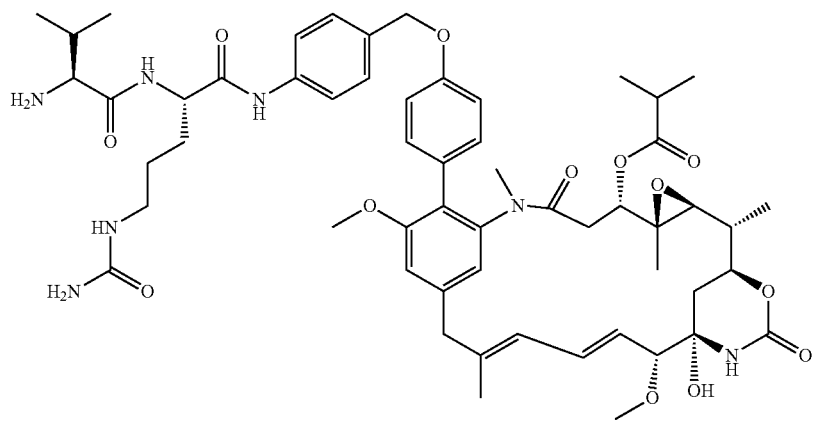

68

A solution of compound 67 (92 mg) in formic acid (2 mL) was stirred at room temperature for 80 min. The reaction mixture was then concentrated in vacuo, the residue was dissolved in DMF (5 mL) and then purified by reverse phase C-18 column chromatography eluting with buffer A (v/v): water:0.1% acetic acid and buffer B (v/v): acetonitrile:0.1% acetic acid (100:0 v/v to 0:100 v/v). The desired fractions were combined and lyophilised to give compound 68 as a white solid (47 mg). LC/MS: (ES+) [M+H]$^+$ (1054, 100%).

Step 3: Synthesis of Reagent 66.

Reagent 66 was synthesised in an analogous way to reagent 47 of Example 21 (Step 3) using compound 68 instead of compound 49. Reagent 66 was isolated as a white solid. $^1$H NMR (500 MHz; DMSO-d$_6$) δ 10.02 (s, 1H), 8.76 (d, J=7.8 Hz, 0.5H), 8.16-8.14 (m, 0.5H), 8.05-8.02 (m, 1H), 7.92-7.79 (m, 2H), 7.69-7.61 (m, 2H), 7.57-7.51 (m, 5H), 7.47-7.43 (m, 4H), 7.41-7.31 (m, 2H), 7.12 (d, J=0.4 Hz, 1H), 7.09-7.08 (m, 2H), 7.00 (d, J=8.8 Hz, 2H), 6.86 (s, 1H), 6.81 (s, 1H), 6.65-6.60 (m, 0.5H), 6.53 (s, 0.5H), 6.23-6.20 (m, 0.5H), 5.99-5.97 (m, 0.5H), 5.89-5.87 (m, 1H), 5.45-5.40 (m, 3H), 5.06-5.00 (m, 1H), 4.59-4.53 (m, 0.5H), 4.44-4.39 (m, 1H), 4.27-4.24 (m, 0.5H), 4.14-4.07 (m, 0.5H), 4.02-3.97 (m, 0.5H), 3.86-3.80 (m, 1H), 3.76 (s, 3H), 3.74-3.71 (m, 1.5H), 3.68-3.63 (m, 0.5H), 3.51 (s, 96H), 3.46-3.42 (m, 5H), 3.25 (d, J=4.4 Hz, 7H), 3.05-2.94 (m, 1.5H), 2.90-2.85 (m, 0.5H), 2.72-2.70 (m, 1H), 2.66-2.63 (m, 2H), 2.46 (s, 6H), 2.40-2.37 (m, 2H), 2.34-2.27 (m, 2H), 2.20-2.17 (m, 1H), 2.05-1.91 (m, 2H), 1.72-1.68 (m, 4H), 1.62-1.59 (m, 0.5H), 1.52-1.35 (m, 4.5H), 1.14 (d, J=6.9 Hz, 6H), 1.10 (d, J=6.6 Hz, 3H), 0.94 (s, 3H), 0.88 (d, J=6.5 Hz, 3H), 0.84 (d, J=6.7 Hz, 4H). LC/MS: (ES+) [M+2H]$^{2+}$ (1368, 20%), [M+3H]$^{3+}$ (912, 70%), [M+4H]$^{4+}$ (684, 100%).

Example 26: Preparation of Conjugation Reagent 69 Comprising a Maytansinoid Cytotoxic Payload

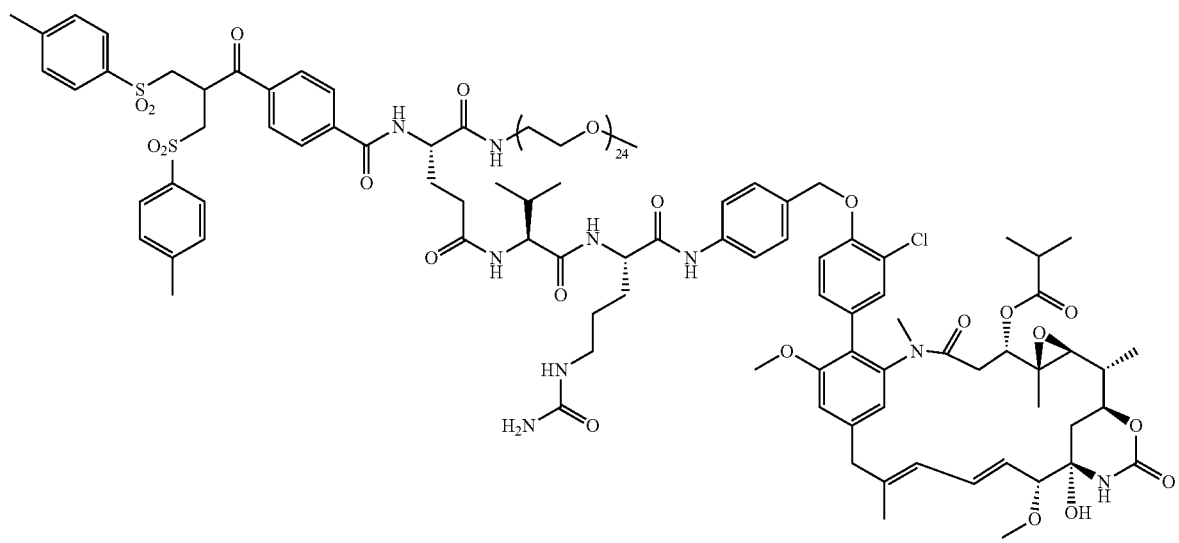

69

Reagent 69 was synthesised in an analogous way to reagent 66 of Example 25 using compound 62 instead of compound 58 (step 1). Reagent 69 was isolated as a white solid. $^1$H NMR (500 MHz; CDCl$_3$) δ 9.15 (s, 0.5H), 7.96-7.88 (m, 2.5H), 7.80-7.72 (m, 1H), 7.75-7.66 (m, 8H), 7.47-7.44 (m, 1H), 7.37-7.32 (m, 7H), 7.17 (s, 1H), 6.97 (d, J=8.4 Hz, 1H), 6.89 (d, J=8.1 Hz, 1H), 6.85 (d, J=4.7 Hz, 2H), 6.48 (dd, J=15.3, 11.0 Hz, 0.5H), 6.25-6.17 (m, 1.5H), 5.97-5.86 (m, 0.5H), 5.50-5.45 (m, 0.5H), 5.11-5.00 (m, 4H), 4.81 (dd, J=11.6, 1.9 Hz, 1H), 4.67-4.65 (m, 0.5H), 4.56-1.55 (m, 0.5H), 4.38-4.20 (m, 2H), 3.81 (s, 3H), 3.63 (s, 96H), 3.57-3.52 (m, 12H), 3.37 (d, J=5.5 Hz, 6H), 3.27-3.20 (m, 3H), 2.94 (dd, J=27.1, 11.3 Hz, 2H), 2.69 (s, 3H), 2.65-2.61 (m, 1H), 2.47 (s, 6H), 2.41-2.34 (m, 1.5H), 2.22-2.13 (m, 2.5H), 1.98-1.95 (m, 1H), 1.83-1.79 (m, 3H), 1.74 (s, 3H), 1.66 (d, J=13.5 Hz, 1H), 1.58-1.48 (m, 2H), 1.29 (d, J=6.1 Hz, 3H), 1.25 (d, J=7.1 Hz, 4H), 1.19 (d, J=6.7 Hz, 3H), 1.00 (t, J=6.4 Hz, 5H), 0.93 (s, 3H). LC/MS: (ES+) [M+2H]$^{2+}$ (1385, 15%), [M+3H]$^{3+}$ (923, 75%), [M+4H]$^{4+}$ (693, 100%).

Example 27: Preparation of Conjugation Reagent 70 Comprising a Maytansinoid Cytotoxic Payload

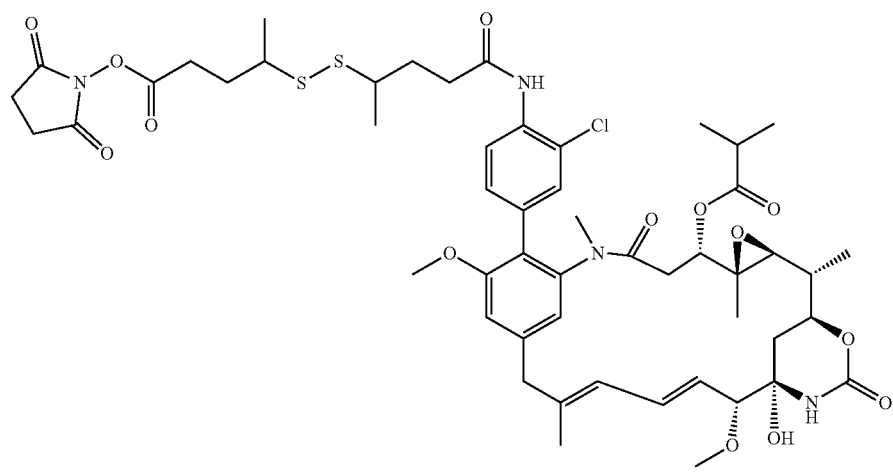

70

Step 1: Synthesis of Compound 71.

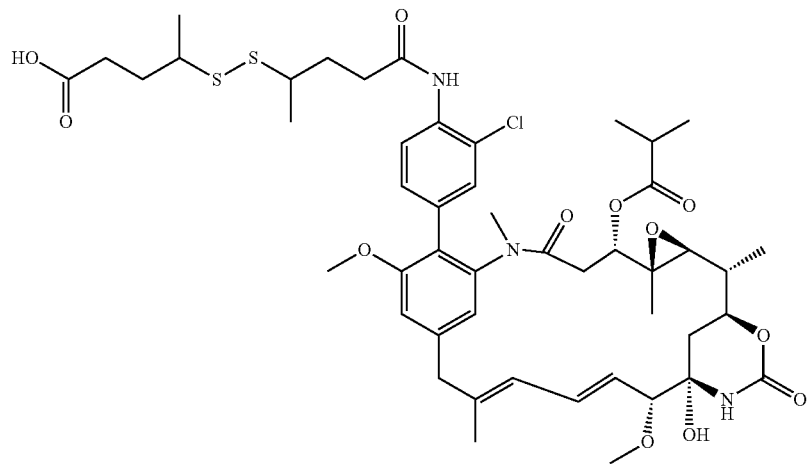

71

A solution of compound 18 (18 mg) and compound 7 (19 mg) in anhydrous DMF (1 mL) was stirred under an argon atmosphere at room temperature for 18 h. The reaction solution was then diluted with water (1 mL) and purified by reverse phase C-18 column chromatography eluting with buffer A (v/v): water:0.05% acetic acid and buffer B (v/v): acetonitrile:0.05% acetic acid (70:30 v/v to 10:90 v/v). The desired fractions were combined, concentrated in vacuo and lyophilised to give compound 71 as a white solid (12 mg). NMR (500 MHz; CDCl$_3$): δ 8.41 (s, 1H), 7.70 (s, 1H), 7.12 (s, 1H), 7.04 (d, J=7.3 Hz, 1H), 6.87 (dd, J=10.8, 5.9 Hz, 2H), 6.48 (dd, J=15.2, 10.9 Hz, 1H), 6.31 (s, 1H), 6.19 (dd, J=11.0, 0.5 Hz, 1H), 5.47 (dd, J=15.4, 8.8 Hz, 1H), 4.84-4.81 (m, 1H), 4.32-4.28 (m, 1H), 3.82 (d, J=5.0 Hz, 3H), 3.56 (d, J=12.7 Hz, 1H), 3.52 (d, J=9.0 Hz, 1H), 3.37 (s, 3H), 3.28-3.21 (m, 2H), 3.00 (dd, J=10.0, 4.8 Hz, 1H), 2.91 (t, J=13.0 Hz, 1H), 2.73 (d, J=8.7 Hz, 3H), 2.67-2.56 (m, 4H), 2.44 (d, J=8.5 Hz, 1H), 2.23 (dd, J=13.8, 3.1 Hz, 1H), 2.16 (dt, J=12.7, 6.6 Hz, 1H), 2.03 (ddt, J=25.3, 12.2, 6.5 Hz, 4H), 1.50 (d, J=6.7 Hz, 3H), 1.45 (d, J=6.7 Hz, 3H), 1.36 (dt, J=6.9, 3.6 Hz, 1H), 1.31 (q, J=6.1 Hz, 5H), 1.25 (dt, J=7.5, 4.1 Hz, 4H), 1.20 (d, J=6.7 Hz, 3H), 0.93 (s, 3H). LC/MS: (ES+) [M+H]$^+$ (974, 100%), [M+Na]$^+$ (996, 45%)

Step 2: Synthesis of Reagent 70.

A mixture of compound 71 (11 mg), EDC.HCl (15 mg) and N-hydroxysuccinimide (10 mg) in anhydrous dichloromethane (3 mL) was stirred under an argon atmosphere at room temperature for 72 h. The reaction mixture was then concentrated in vacuo and the residue dissolved in dichloromethane:acetonitrile (2 mL, 1:1 v/v) before purification by normal phase chromatography eluting with dichloromethane:acetonitrile (100:0 v/v to 0:100 v/v). The desired fractions were combined and the solvent was removed in vacuo to give reagent 70 as a white solid (12 mg). $^1$H NMR (500 MHz; CDCl$_3$): δ 8.41 (d, J=7.5 Hz, 1H), 7.79-7.70 (m, 1H), 7.12 (s, 1H), 7.06-7.04 (m, 1H), 6.86 (d, J=11.8 Hz, 2H), 6.48 (dd, J=15.4, 11.0 Hz, 1H), 6.19 (d, J=14.5 Hz, 2H), 5.49-5.45 (m, 1H), 4.83 (dd, J=11.7, 2.6 Hz, 1H), 4.30 (t, J=11.2 Hz, 1H), 3.81 (s, 3H), 3.56 (d, J=12.8 Hz, 1H), 3.52 (d, J=8.8 Hz, 1H), 3.37 (s, 3H), 3.27 (d, J=12.5 Hz, 2H), 3.00 (d, J=9.8 Hz, 2H), 2.93 (dd, J=13.0, 4.8 Hz, 2H), 2.87-2.79 (m, 7H), 2.72 (d, J=3.3 Hz, 3H), 2.62 (tt, J=13.4, 6.5 Hz, 3H), 2.23 (d, J=14.2 Hz, 1H), 2.07 (dddd, J=31.6, 23.4, 16.2, 7.7 Hz, 4H), 1.74 (s, 3H), 1.67 (d, J=13.6 Hz, 1H), 1.50 (d, J=6.7 Hz, 1H), 1.47 (d, J=6.7 Hz, 1H), 1.37 (dd, J=6.8, 1.7 Hz, 2H), 1.34 (d, J=6.9 Hz, 2H), 1.31 (d, J=6.3 Hz, 3H), 1.26 (q, J=8.3 Hz, 5H), 1.20 (d, J=6.7 Hz, 3H), 0.94 (s, 3H). LC/MS: (ES+) [M+H]$^+$ (1071, 100%), [M+Na]$^+$ (1093, 80%).

Example 28: Preparation of Conjugation Reagent 72 Comprising a Maytansinoid Cytotoxic Payload Step 1: Synthesis of Compound 73.

To a solution of Fmoc-Lys(Boc)-OH (470 mg) in anhydrous DMF (5 mL) at 0° C. was added HATU (1.4 g). To this was added a solution of NH$_2$—PEG(24u)-OMe (1 g) and NMM (340 µL) in anhydrous DMF (5 mL) at 0° C. before the solution was allowed to warm to room temperature and was stirred for 1 h. The reaction mixture was then concentrated in vacuo and purified by reverse phase C18-column chromatography, eluting with buffer A (v/v): water:0.05% trifluoroacetic acid and buffer B (v/v): acetonitrile:0.05% trifluoroacetic acid (95:5 v/v to 0:100 v/v). The organic solvent was removed in vacuo and the aqueous solvent removed by lyophilisation to give Fmoc-Lys(Boc)-[PEG (24u)-OMe]. LC/MS: (ES+) [M+Na]$^+$ (1560, 100%), [M+H]$^+$ (1539, 80%). To a solution of the Fmoc-Lys(Boc)-[PEG(24u)-OMe] in DMF (10 mL) was added piperidine (0.9 mL) and the solution was stirred for 10 min at room temperature. The reaction solution was concentrated in vacuo and purified by reverse phase C18-column chromatography, eluting with buffer A (v/v): water:0.05% trifluoroacetic acid and buffer B (v/v): acetonitrile:0.05% trifluoroacetic acid (95:5 v/v to 0:100 v/v). The organic solvent was removed in vacuo and the aqueous solvent removed by lyophilisation to give compound 73 as a white solid (1 g). LC/MS: (ES+) [M+H]$^+$ (1316, 10%), [M+2H-Boc]$^{2+}$ (609, 100%).

Step 2: Synthesis of Compound 74.

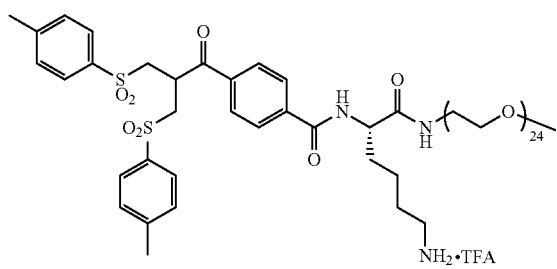

74

To a solution of compound 36 (420 mg) in anhydrous DMF (2 mL) was added a solution of compound 73 (1 g) and NMM (92 µL) in anhydrous DMF (3 mL). After stirring for 2.5 at room temperature, the reaction mixture was concentrated in vacuo and purified by reverse phase C18-column chromatography, eluting with buffer A (v/v): water:0.05% trifluoroacetic acid and buffer B (v/v): acetonitrile:0.05% trifluoroacetic acid (95:5 v/v to 0:100 v/v). The organic solvent was removed in vacuo and the aqueous solvent removed by lyophilisation to give bis-tolylsulfonyl-propanoyl-benzamide-L-Lys-[Boc]-[PEG(24u)-OMe] as a white solid (0.84 g). LC/MS: (ES+) [M+2H-Boc]$^{2+}$ (850, 95%). Bis-tolylsulfonyl-propanoyl-benzamide-L-Lys-[Boc]-[PEG(24u)-OMe] (0.84 g) was then dissolved in formic acid (3 mL) and the solution stirred at room temperature for 3 h. The volatiles were removed in vacuo and the residue washed with toluene (3×6 mL) before the residue was dried in vacuo and purified by reverse phase C18-column chromatography, eluting with buffer A (v/v): water: 0.05% trifluoroacetic acid and buffer B (v/v): acetonitrile: 0.05% trifluoroacetic acid (95:5 v/v to 0:100 v/v). The organic solvent was removed in vacuo and the aqueous solvent removed by lyophilisation to give compound 74 as a white solid (0.59 g). LC/MS: (ES+) [M+H]$^+$ (1699, 5%), [M+2H]$^{2+}$ (850, 100%).

Step 3: Synthesis of Reagent 72.

To a solution of compound 74 (52 mg) in anhydrous DMF (0.9 mL) was added reagent 25 (21 mg) followed by NMM (9 µL) and the mixture was stirred at room temperature. Additional quantities of NMM (2×9 µL) were added after 2 and 4 h and then after 6 h, the reaction solution was stored at −20° C. for a further 16 h. The reaction solution was then concentrated in vacuo, the residue dissolved in acetonitrile (400 µL) and then purified by reverse phase C18-column chromatography, eluting with buffer A (v/v): water:0.05% trifluoroacetic acid and buffer B (v/v): acetonitrile:0.05% trifluoroacetic acid (70:30 v/v to 0:100 v/v). The desired fractions were combined and lyophilised to give reagent 72 as a white solid (17 mg). MS: (ES+) [M+2Na]$^{2+}$ (1333, 10%), [M+3H]$^{3+}$ (874, 100%), [M+4H]$^{4+}$ (656, 30%).

Example 29: Preparation of Conjugation Reagent 75 Comprising a Maytansinoid Cytotoxic Payload

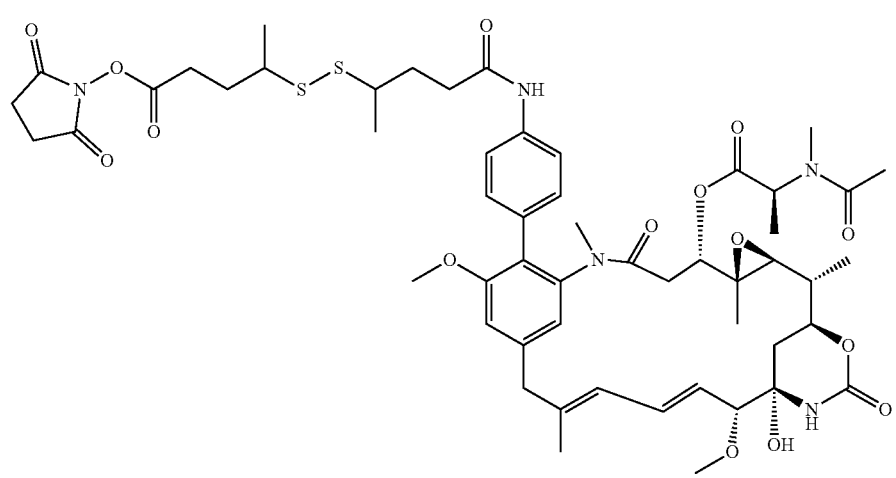

75

Step 1: Synthesis of Compound 76.

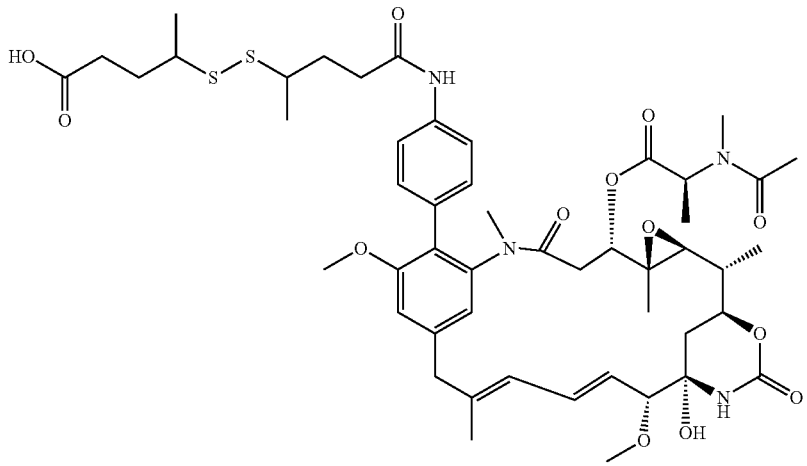

A mixture of compound 34 (40 mg) and 4-mercaptopentanoic acid (27 mg) in DMF (5 mL) was stirred at room temperature for 16 h. The reaction mixture was then directly purified by reverse phase C-18 column chromatography eluting with buffer A (v/v): water:0.1% acetic acid and buffer B (v/v): acetonitrile:0.1% acetic acid (100:0 v/v to 0:100 v/v). The desired fractions were combined and lyophilised to give compound 76 as a white solid (36 mg). LC/MS: (ES+) $[M+H]^+$ (998, 100%), $[M+2H]^{2+}$ (499, 20%).

Step 2: Synthesis of Reagent 75.

Reagent 75 was synthesised in an analogous way to reagent 25 of Example 12 using compound 76 instead of compound 26. Reagent 75 was isolated as a white solid. $^1$H NMR (500 MHz; CDCl$_3$) δ 7.76-7.70 (m, 1H), 7.58-7.56 (m, 2H), 7.08-7.06 (m, 2H), 6.84 (d, J=0.4 Hz, 1H), 6.72-6.68 (m, 2H), 6.46 (dd, J=15.3, 11.3 Hz, 1H), 6.25 (s, 1H), 5.72-5.67 (m, 1H), 5.36-5.32 (m, 1H), 4.82-4.79 (m, 1H), 4.30 (td, J=11.2, 1.4 Hz, 1H), 3.81 (s, 3H), 3.70 (d, J=12.9 Hz, 1H), 3.52 (d, J=9.1 Hz, 1H), 3.37 (s, 3H), 3.18-3.15 (m, 1H), 3.09-3.02 (m, 2H), 2.96-2.73 (m, 6H), 2.66 (s, 3H), 2.54-2.51 (m, 2H), 2.28-2.24 (m, 1H), 2.15-1.95 (m, 6H), 1.69 (s, 3H), 1.66 (d, J=0.4 Hz, 1H), 1.53-1.47 (m, 1H), 1.37 (d, J=6.7 Hz, 3H), 1.34-1.25 (m, 13H), 0.92 (s, 3H). LC/MS: (ES+) $[M+H]^+$ (1094, 100%).

Example 30: Preparation of Conjugation Reagent 77 (Comparator) Comprising a Maytansinoid Cytotoxic Payload

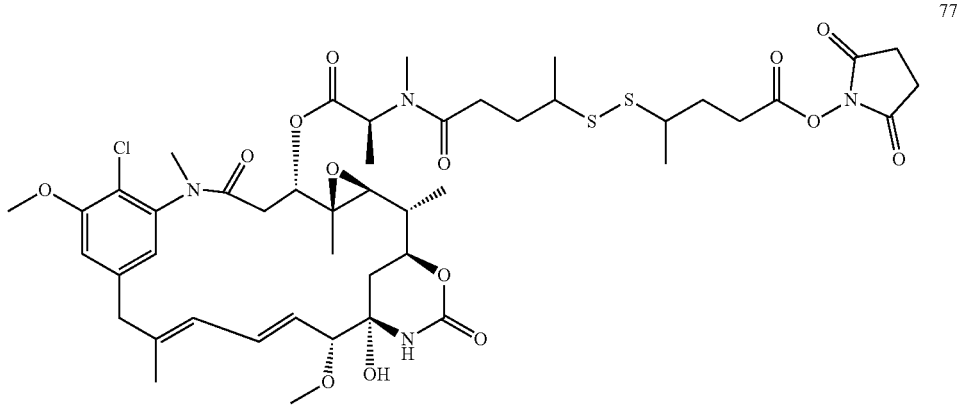 [SMILES: COc1cc2cc(c1Cl)N(C)C(=O)C[C@H](OC(=O)[C@H](C)N(C)C(=O)CCC(C)SSC(C)CCC(=O)ON1C(=O)CCC1=O)[C@]1(C)O[C@H]1[C@H](C)[C@@H]1C[C@@](O)(NC(=O)O1)[C@H](OC)/C=C/C=C(\C)C2]

Step 1: Synthesis of Compound 78.

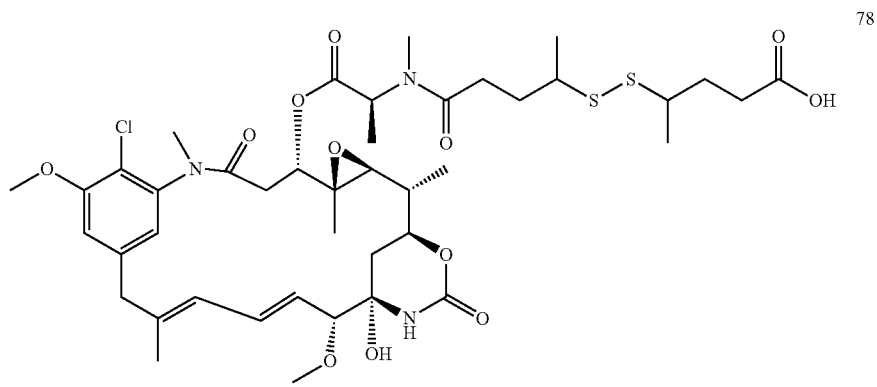 [SMILES: COc1cc2cc(c1Cl)N(C)C(=O)C[C@H](OC(=O)[C@H](C)N(C)C(=O)CCC(C)SSC(C)CCC(=O)O)[C@]1(C)O[C@H]1[C@H](C)[C@@H]1C[C@@](O)(NC(=O)O1)[C@H](OC)/C=C/C=C(\C)C2]

Compound 78 was synthesised in an analogous way to compound 71 of Example 27 using N2'-deacetyl-N2'-(4-mercapto-1-oxopentyl)-maytansine (available from BOC Sciences) instead of compound 18. Compound 78 was isolated as a white solid. $^1$H NMR (500 MHz; CDCl$_3$): δ 6.83 (s, 1H), 6.69-6.67 (m, 1H), 6.42 (ddd, J=14.9, 11.3, 3.4 Hz, 1H), 6.32 (d, J=6.4 Hz, 1H), 5.69-5.62 (m, 1H), 4.92-4.86 (m, 1H), 4.32 (quintet, J=9.8 Hz, 1H), 3.99 (s, 3H), 3.62 (ddd, J=20.7, 13.1, 7.4 Hz, 1H), 3.48 (td, J=10.4, 4.2 Hz, 1H), 3.35 (d, J=2.8 Hz, 3H), 3.21 (s, 3H), 3.17-3.12 (m, 1H), 3.01-2.95 (m, 2H), 2.91 (dd, J=13.8, 8.8 Hz, 2H), 2.84 (td, J=14.1, 6.7 Hz, 2H), 2.67-2.60 (m, 2H), 2.55-2.36 (m, 4H), 2.20 (dd, J=14.4, 2.6 Hz, 1H), 1.95 (td, J=13.2, 6.9 Hz, 2H), 1.81 (dt, J=20.0, 5.7 Hz, 2H), 1.73 (dd, J=19.2, 14.2 Hz, 1H), 1.65 (s, 3H), 1.48-1.45 (m, 2H), 1.39 (dd, J=12.6, 6.9 Hz, 2H), 1.34 (dd, J=9.0, 7.0 Hz, 2H), 1.32-1.25 (m, 12H), 0.82 (dd, J=11.9, 5.7 Hz, 3H). LC/MS: (ES+) [M–H$_2$O+H]$^+$ (880, 100%), [M+H]$^+$ (898, 15%), [M+Na]$^+$ (920, 60%).

Step 2: Synthesis of Reagent 77.

Reagent 77 was synthesised in an analogous way to reagent 25 of Example 12 using compound 78 instead of compound 26. Reagent 77 was isolated as a white solid. $^1$H NMR (500 MHz; CDCl$_3$): δ 6.86-6.83 (m, 1H), 6.75 (t, J=8.8 Hz, 1H), 6.64 (d, J=4.8 Hz, 1H), 6.43 (dd, J=15.3, 11.2 Hz, 1H), 6.20 (s, 1H), 5.67 (ddd, J=15.0, 9.4, 5.2 Hz, 1H), 5.42 (q, J=6.7 Hz, 1H), 4.78 (dd, J=12.0, 2.7 Hz, 1H), 4.27 (t, J=11.3 Hz, 1H), 3.98 (s, 3H), 3.65 (d, J=12.7 Hz, 1H), 3.50 (d, J=9.0 Hz, 1H), 3.35 (s, 3H), 3.22 (s, 3H), 3.13 (t, J=10.2 Hz, 1H), 3.04 (d, J=9.7 Hz, 1H), 2.85 (d, J=3.4 Hz, 9H), 2.72 (t, J=6.9 Hz, 2H), 2.61 (t, J=13.2 Hz, 1H), 2.55-2.49 (m, 1H), 2.46-2.35 (m, 1H), 2.17 (dd, J=14.3, 2.4 Hz, 1H), 2.04-1.83 (m, 4H), 1.64 (s, 3H), 1.57 (d, J=13.6 Hz, 1H), 1.51 (s, 2H), 1.48-1.44 (m, 1H), 1.30-1.23 (m, 14H), 0.80 (s, 3H). LC/MS: (ES+) [M–H$_2$O+H]$^+$ (977, 100%), [M+H]$^+$ (995, 15%), [M+Na]$^+$ (1017, 55%).

Example 31: Preparation of Maytansinoid Compound 79

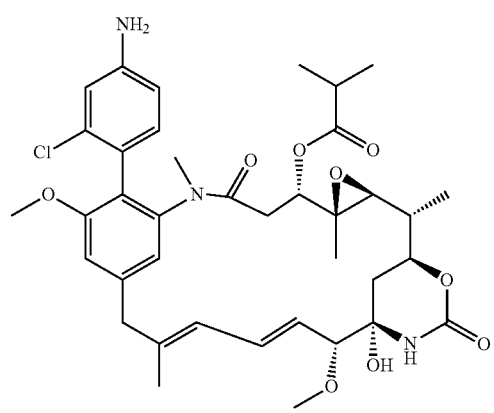

Compound 79, which was synthesised as a mixture of atropisomers, was prepared in a similar way to compound 4 of Example 3. Briefly, 4-amino-2-chlorophenylboronic acid pinacol ester (66 mg), tripotassium phosphate (148 mg), SPhos Pd G3 (13.6 mg) and AP3 (100 mg) were sequentially added to an argon purged reaction vessel. The vessel was then sealed and the solids purged with argon (4×evacuation/purge cycles). THF (1.2 mL) and water (120 μL), which had been rigorously deoxygenated by purging with argon, were then added and the reaction mixture was stirred at room temperature for 12 h. Analysis of the crude reaction mixture by LC/MS identified two peaks with the expected molecular mass for compound 79. The two peaks resolved at 2.81 and 3.00 min correspond to two atropisomer species. Henceforth, the atropisomers eluting at 2.81 and 3.00 min will be referred to as compounds 80 and 81, respectively.

Separation of the atropisomers was achieved by reverse phase preparative HPLC. Firstly, the crude reaction mixture was diluted with ethyl acetate (40 mL) and then washed with brine (20 mL). The organic layer was separated and concentrated in vacuo and the residue dissolved in DMF (4 mL). Atropisomers 80 and 81 were separated by reverse phase preparative HPLC using a Luna C18(2) column (250 mm L×50 mm ID, 5 μm) eluting with buffer A (v/v): water:0.05% acetic acid and buffer B (v/v): acetonitrile:0.05% acetic acid (90:10 v/v to 10:90 v/v, 35 min, room temperature). Fractions corresponding to the two atropisomers (as confirmed by LC/MS) were separated and lyophilised to give compounds 80 and 81 as white solids. Each compound was then further purified by normal phase chromatography eluting with dichloromethane:acetone (100:0 v/v to 50:50 v/v) to give compound 80 (15 mg) and compound 81 (10 mg) as white solids. The HPLC chromatograms of compounds 80 and 81 following normal phase purification indicate that both compounds achieved a purity >96% by peak area.

The stability of the atropisomers was investigated by heating solutions of compounds 80 and 81 in DMSO at 50° C. for 1 h. After heating for 1 h, the compounds were analysed by HPLC and no changes were observed from the HPLC chromatograms of the pre-heated samples, indicating both atropisomers are stable and do not interconvert at the indicated elevated temperature.

Characterisation data for compound 80: $^1$H NMR (500 MHz; CDCl$_3$) δ 6.92 (d, J=8.2 Hz, 1H), 6.84 (s, 2H), 6.73 (d, J=2.1 Hz, 1H), 6.57 (dd, J=8.2, 2.2 Hz, 1H), 6.51-6.45 (m, 1H), 6.21 (s, 1H), 6.18-6.16 (m, 1H), 5.47-5.42 (m, 1H), 4.76-4.74 (m, 1H), 4.30-4.25 (m, 1H), 3.81 (s, 3H), 3.55 (d, J=12.6 Hz, 1H), 3.51 (d, J=8.8 Hz, 1H), 3.36 (s, 3H), 3.28 (d, J=12.6 Hz, 1H), 3.01 (s, 1H), 2.94 (s, 3H), 2.87 (t, J=13.3 Hz, 1H), 2.64-2.59 (m, 1H), 2.19-2.15 (m, 1H), 1.77 (s, 3H), 1.66-1.63 (m, 1H), 1.50-1.45 (m, 1H), 1.29-1.24 (m, 6H), 1.19 (d, J=6.7 Hz, 3H), 0.87 (s, 3H). LC/MS: retention time 2.81 min (Acquity UPLC BEH C18 1.7 μm, 2.1×50 mm column, eluting with water (0.05% acetic acid):acetonitrile (0.05% acetic acid) (95:5 v/v to 5:95 v/v), 5 min gradient, 0.6 mL/min, room temperature), (ES+) [M+H]$^+$ (726, 100%).

Characterisation data for compound 81: $^1$H NMR (500 MHz; CDCl$_3$) δ 6.89 (s, 1H), 6.84 (s, 1H), 6.77 (d, J=2.1 Hz, 1H), 6.67 (d, J=8.2 Hz, 1H), 6.57 (dd, J=8.2, 2.1 Hz, 1H), 6.51-6.46 (m, 1H), 6.27 (s, 1H), 6.19 (d, J=11.1 Hz, 1H), 5.47 (dd, J=15.3, 9.0 Hz, 1H), 4.84-4.82 (m, 1H), 4.32-4.27 (m, 1H), 3.84 (s, 3H), 3.58 (d, J=13.1 Hz, 1H), 3.52 (d, J=8.9 Hz, 1H), 3.37 (s, 3H), 3.26 (d, J=13.1 Hz, 1H), 3.02-2.91 (m, 2H), 2.72 (s, 3H), 2.67-2.58 (m, 1H), 2.23-2.21 (m, 1H), 1.74 (s, 3H), 1.68 (d, J=13.2 Hz, 1H), 1.53-1.47 (m, 2H), 1.30 (d, J=6.3 Hz, 3H), 1.28-1.24 (m, 4H), 1.20 (d, J=6.7 Hz, 3H), 0.94 (s, 3H). LC/MS: retention time 3.00 min, (ES+) [M+H]$^+$ (726, 100%).

The invention includes the individual atropisomers of the compound of formula 79. For example, it includes the atropisomer having a retention time of 2.81 minutes when analysed by LC/MS under the conditions indicated above in Example 31, and also includes the atropisomer having a retention time of 3.00 minutes when analysed by LC/MS under the conditions indicated above in Example 31.

Using a combination of 2D NMR (ROESY) spectroscopy and molecular modelling studies, it is proposed that compounds 80 and 81 have the following structures:

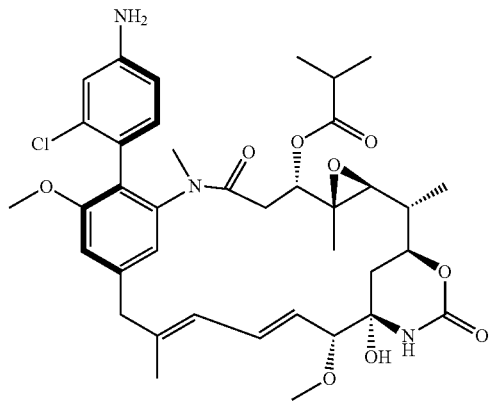

80

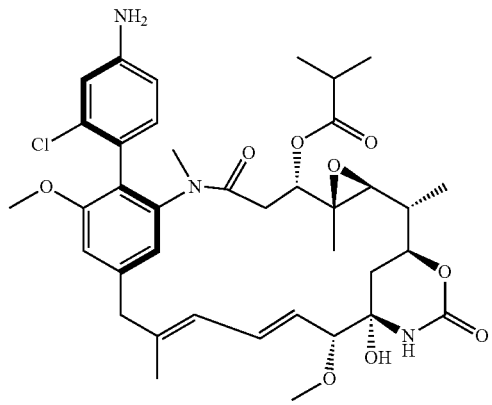

81

Example 32: In Vitro Potency Assay of Compounds in SK-BR-3 Cell Lines

Loss of tumour cell viability following treatment with compounds of the invention was tested by growing SK-BR-3 cell lines in the presence of increasing concentrations of compounds of the invention and quantifying the loss of proliferation or metabolic activity as described in Example 2. The average IC$_{50}$ values for compounds of the invention are shown in Table 6 and the assay concentrations are specified in Table 7.

TABLE 6

| Compound | Average IC$_{50}$ (nM) SK-BR-3 Cell line |
| --- | --- |
| 9 | 7.4 (n = 2) |
| 12 | 4.2 (n = 2) |
| 15 | 5.4 (n = 2) |
| 21 | 1.7 (n = 2) |
| 23 | 4.2 (n = 2) |
| 32 | 5.5 (n = 2) |
| 53 | 11.2 (n = 2) |
| 54 | 2.9 (n = 3) |
| 55 | 0.9 (n = 3) |
| 56 | 17.0 (n = 2) |
| 57 | 3.6 (n = 2) |
| 58 | 0.5 (n = 3) |
| 59 | 3.9 (n = 2) |
| 60 | 1.3 (n = 3) |
| 61 | 6.0 (n = 2) |
| 62 | 1.4 (n = 3) |
| 63 | 2.8 (n = 2) |
| 64 | 4.9 (n = 3) |

TABLE 6-continued

| Compound | Average IC$_{50}$ (nM) SK-BR-3 Cell line |
|---|---|
| 80 | 3.6 (n = 3) |
| 81 | 0.9 (n = 3) |
| 31 (comparator) | 33.4 (n = 3) |

TABLE 7

| Cell line | Compound | Concentration range |
|---|---|---|
| SK-BR-3 | 9 | 200 nM-91 pM |
| SK-BR-3 | 12 | 200 nM-91 pM |
| SK-BR-3 | 15 | 200 nM-91 pM |
| SK-BR-3 | 21 | 200 nM-2.6 pM |
| SK-BR-3 | 23 | 200 nM-2.6 pM |
| SK-BR-3 | 32 | 500 nM-6.4 pM |
| SK-BR-3 | 53 | 300 nM-137 pM |
| SK-BR-3 | 54 | 800 nM-0.4 pM |
| SK-BR-3 | 55 | 800 nM-0.4 pM |
| SK-BR-3 | 56 | 1000 nM-61 pM |
| SK-BR-3 | 57 | 500 nM-6.4 pM |
| SK-BR-3 | 58 | 100 nM-6.1 pM |
| SK-BR-3 | 59 | 1000 nM-3.6 pM |
| SK-BR-3 | 60 | 700 nM-0.9 pM |
| SK-BR-3 | 61 | 1000 nM-3.6 pM |
| SK-BR-3 | 62 | 100 nM-1.3 pM |
| SK-BR-3 | 63 | 800 nM-2.9 pM |
| SK-BR-3 | 64 | 200 nM-12 pM |
| SK-BR-3 | 80 | 200 nM-12 pM |
| SK-BR-3 | 81 | 100 nM-1.3 pM |
| SK-BR-3 | 31 (comparator) | 1000 nM-457 pM |

These data show that compounds of the invention, which contain a biphenyl moiety, unexpectedly have lower IC$_{50}$ values than the allylamine-containing comparator.

Example 33: Conjugation of Reagents 35, 47, 69 and 72 to Trastuzumab to Produce Antibody Drug Conjugates (ADCs) 82, 83, 84 and 85 Respectively, with DAR 4

Conjugation reagents 35, 47, 69 and 72 were conjugated to Trastuzumab giving rise to ADCs 82, 83, 84 and 85 using methods analogous to those described in WO2014064423 and WO2014064424.

Briefly, Trastuzumab (5-7.4 mg/mL in 20 mM sodium phosphate, 150 mM NaCl, 20 mM EDTA pH 7.5) was heated to 40° C. in a heating block for 15 min. 5 mM TCEP solution (6 eq. per mAb) was added to the mAb solution, mixed gently and incubated at 40° C. for 1 h before being allowed to cool to 22° C.

For conjugations using reagents 35, 47 and 69, the reduced mAb solution was then diluted to 4.4 mg/mL with 20 mM sodium phosphate, 150 mM NaCl, 20 mM EDTA, pH 7.5. Conjugation reagents 35, 47 and 69 were dissolved in DMF to give 1.5 mM solutions. Conjugation reagent (5.6 eq. per mAb) was added to the mAb solutions to give final antibody concentrations of 4.0 mg/mL. For the conjugation using reagent 72, the reagent was dissolved in propylene glycol:DMF (3:1 v/v) to give a 0.75 mM solution. Reagent 72 (5.6 eq. per mAb) was then added to the reduced mAb solution to give a final antibody concentration of 4.0 mg/mL.

Each conjugation reaction solution was then mixed gently and incubated at 22° C. for 18-21 h. The crude reaction solutions were then mixed with equal volumes of 50 mM sodium phosphate, 4 M NaCl, pH 7 and the resulting solutions were loaded onto a ToyoPearl Phenyl-650S HIC column equilibrated with 50 mM sodium phosphate, 2 M NaCl, pH 7. Each ADC was eluted from the column with a gradient of 50 mM sodium phosphate, pH 7 (20% isopropanol). Fractions containing DAR 4 ADC were pooled and concentrated. The concentrated sample was buffer exchanged into PBS, pH 7.1-7.5, and sterile filtered (0.22 μm PVDF membranes). DAR assignments were based on A248/A280 absorption ratios. The average DAR of ADCs 82, 83, 84 and 85 were calculated from the relative peak areas of individual DAR species following HIC analysis at 280 nm.

Example 34: Conjugation of Reagent 41 to Brentuximab to Produce Antibody Drug Conjugate (ADC) 86 with DAR 4

Conjugation reagent 41 was conjugated to Brentuximab giving rise to ADC 86 using a similar method to that described in Example 33. Briefly, Brentuximab (8.5 mg/mL in 20 mM sodium phosphate, 150 mM NaCl, 20 mM EDTA, pH 7.5) was heated to 40° C. in a heating block for 15 min. TCEP (6 eq. per mAb) was added to the mAb solution, mixed gently and incubated at 40° C. for 1 h before being allowed to cool to 22° C. Conjugation reagent 41 was dissolved in DMF to give a 1.6 mM solution. The reduced mAb solution was diluted to 6.7 mg/mL with 20 mM sodium phosphate, 150 mM NaCl, 20 mM EDTA, pH 7.5) followed by the addition of propylene glycol, resulting in a final reduced mAb solution concentration of 4.4 mg/mL. Conjugation reagent (6 eq. per mAb) was added to the mAb solution to give a final antibody concentration of 4 mg/mL. The reaction solution was mixed gently and incubated at 22° C. for 24 h. After this time, the reaction solution was treated with 50 mM N-acetyl-L-cysteine (20 eq. over reagent) at 22° C. for 30 min. The crude reaction solution was then mixed with an equal volume of 50 mM sodium phosphate, 4 M NaCl, pH 7 and the resulting solution was loaded onto a ToyoPearl Phenyl-650S HIC column equilibrated with 50 mM sodium phosphate, 2 M NaCl, pH 7. The ADC was eluted from the column with a gradient of 50 mM sodium phosphate, pH 7 (20% isopropanol). Fractions containing DAR 4 ADC were pooled and concentrated (Vivaspin 20, 10 kDa PES membrane). The concentrated sample was buffer exchanged into DPBS, pH 7.1-7.5, and sterile filtered (0.22 μm PVDF membrane). The ADC was further purified using a Hydroxyapatite Foresight CHT column equilibrated with 10 mM sodium phosphate, pH 6.7. The ADC was eluted from the column with a gradient of 10 mM sodium phosphate, 2 M NaCl, pH 6.7. Fractions containing ADC were pooled and concentrated (Vivaspin 20, 30 kDa PES membrane) and the concentrated sample was buffer exchanged into DPBS, pH 7.1-7.5 and sterile filtered (0.22 μm PVDF membrane). The DAR of the conjugate was determined using the method described in Example 33.

Example 35: Conjugation of Reagent 50 to Trastuzumab to Produce Antibody Drug Conjugate (ADC) 87

Conjugation reagent 50 was conjugated to Trastuzumab, giving rise to ADC 87. Briefly, reagent 50 was dissolved in DMSO to give a 10 mM stock solution. Trastuzumab in 100 mM HEPES buffer, 1 mM EDTA, pH 7.0 (5 mg/mL mAb concentration), was reduced with TCEP (2.2 eq. per mAb) at 37° C. for 2 h. The reduced mAb solution was allowed to cool to 25° C. and was then diluted with DMSO (10% v/v). Conjugation reagent 50 (10 eq. per mAb) was then added to the reduced mAb solution and the reaction mixture was mixed gently and incubated at 25° C. for 30 min. Excess reagent 50 was quenched by incubating the reaction solution with N-acetyl cysteine (10 eq. per mAb) at 25° C. for 30 min. Activated charcoal powder (70% w/w of mAb) was then added to the reaction solution which was gently agitated for 30 min at room temperature to remove unreacted drug related species. The reaction mixture was then filtered (0.22 µm PES membrane) and the purified sample was buffer exchanged into 10 mM succinic acid, 6% w/v trehalose, 0.01% v/v Tween 20, pH 5.5 using PD-10 desalting columns. An average DAR of 4 was assigned to conjugate 87 using the method described in Example 33.

Example 36: Conjugation of Reagents 70, 75 and 77 (Comparator) to Trastuzumab to Produce Antibody Drug Conjugates (ADCs) 88, 89 and 90 (Comparator), Respectively Conjugation reagents 70, 75 and 77 (comparator) were conjugated to Trastuzumab giving rise to ADCs 88, 89 and 90 (comparator), respectively, using the following general conjugation protocol. Briefly, the reagents were dissolved in DMF to give 1.8-4.0 mM stock solutions. To a solution of Trastuzumab in 20 mM sodium phosphate, 150 mM NaCl, 20 mM EDTA, pH 7.5 was added reagent stock solution (5-20 eq. per mAb, either as a single addition or as multiple aliquots throughout the incubation period) to give a final antibody concentration of 3.0-4.0 mg/mL (containing DMF 10% v/v). The reaction solutions were incubated at 22° C. for 1-4 h.

ADCs 88 and 89 were purified by preparative SEC chromatography using a HiLoad 16/600 Superdex 200 pg column and isocratic elution using PBS (15% isopropanol) as eluent. ADC 90 (comparator) was purified using a Foresight CHT hydroxyapatite column equilibrated with 10 mM sodium phosphate, pH 6.7 and the ADC was eluted from the column with a gradient of 10 mM sodium phosphate, 2 M sodium chloride, pH 6.7.

After column chromatography, the desired ADC containing fractions were pooled and concentrated. The concentrated samples were buffer exchanged into PBS, and sterile filtered. DAR assignments were calculated from the relative peak intensities of the individual DAR species following mass spectrometry. Average DARs of 2.0, 3.2 and 3.1 were calculated for ADCs 88, 89 and 90 (comparator), respectively.

Example 37: Analysis of ADCs by In Vitro Cell Viability Assay

Loss of tumour cell viability following treatment with ADCs incorporating maytansinoids of the invention was tested by growing cell lines in the presence of increasing concentrations of ADCs and quantifying the loss of proliferation or metabolic activity as described in Example 2. The average $IC_{50}$ values for ADCs incorporating the maytansinoids of the invention are shown in Table 8 and the assay concentrations are specified in Table 9.

TABLE 8

| Compound | Average $IC_{50}$ (nM) |
|---|---|
| 29 | 0.05 (n = 4) |
| 30 | 0.08 (n = 2) |
| 82 | 0.18 (n = 2) |
| 83 | 0.18 (n = 3) |
| 84 | 0.14 (n = 2) |
| 85 | 0.26 (n = 2) |
| 86 | 0.11 (n = 2) |
| 87 | 0.17 (n = 2) |
| 88 | 0.08 (n = 2) |
| 89 | 0.10 (n = 2) |

TABLE 9

| Cell line | Compound | Concentration range |
|---|---|---|
| SK-BR-3 | 29 | 2 nM-3.2 pM |
| SK-BR-3 | 30 | 10 nM-0.6 pM |
| SK-BR-3 | 82 | 10 nM-4.6 pM |
| SK-BR-3 | 83 | 20 nM-1.2 pM |
| SK-BR-3 | 84 | 10 nM-0.6 pM |
| SK-BR-3 | 85 | 50 nM-22.9 pM |
| Karpas-299 | 86 | 50 nM-0.18 pM |
| SK-BR-3 | 87 | 1000 nM-3.6 pM |
| SK-BR-3 | 88 | 10 nM-0.6 pM |
| SK-BR-3 | 89 | 10 nM-0.6 pM |

The $IC_{50}$ values obtained show that ADCs incorporating the novel maytansinoids of the invention have potent cell killing properties in vitro.

Example 38: Stability of Compounds 26 and 78 (Comparator) in Mouse Serum

Solutions of compounds 26 and 78 (comparator) in a 50/50 v/v mixture of DMF:buffer solution (20 mM sodium phosphate, 150 mM sodium chloride, 20 mM EDTA, pH 7.5) (0.5 mg/mL) were diluted to 0.05 mg/mL in mouse serum (90% (v/v) serum content). An aliquot of each sample corresponding to the '0' time point was immediately frozen at −80° C., while the remaining sample was incubated at 37° C. for 7 d. Additional aliquots were taken after 4 and 7 d and frozen at −80° C. Prior to analysis, the samples were removed from the freezer and maytansinoid-related species were extracted from the serum by protein precipitation. Protein precipitation was performed by adding acetonitrile (75% v/v) to each time-point aliquot, and after gentle mixing, allowing the mixtures to stand at 4° C. for 2 h. The precipitated protein was then separated by centrifugation (1400×g, 30 min, 4° C.) and the supernatant containing the extracted maytansinoid-related species were analysed by LC-Orbitrap-MS.

Reverse Phase Orbitrap-MS Analysis.

The samples were further diluted with water resulting in a 15% v/v acetonitrile solution. An aliquot (2.5 µL) of each solution was then injected onto a nano-liquid chromatography MS system, consisting of a Dionex ULTIMATE 3000 UPLC fitted with a PepMap C18 column (0.075×150 mm), coupled online to an Orbitrap-MS instrument operated in ES positive mode at 75K resolution using lock mass. Buffer A consisted of 100% water and buffer B of 100% acetonitrile, both containing 0.1% formic acid, and a gradient from 15-80% B was performed at a flow rate of 0.3 µL/min over 60 min. Data analysis was performed manually by analysing for potential degradation products using a Thermo Xcalibur Qual Browser software tool.

Figure 4A:
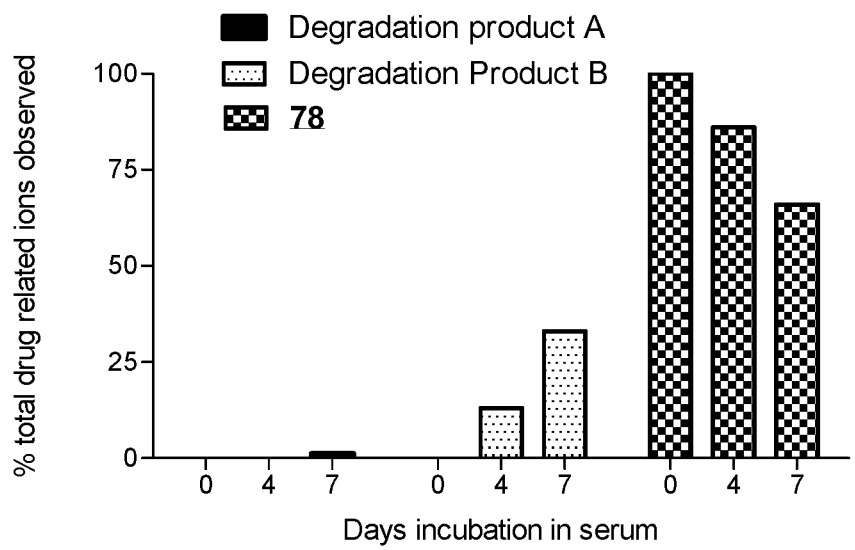
FIG. 4 shows the results of the mouse serum study of Example 38, showing plots of drug-related ions over time for compounds 26 and 78, and demonstrating that significant degradation of compound 78 took place in mouse serum after 7 days at 37° C., whereas no comparable degradation products were observed for compound 26.
Figure 4B:
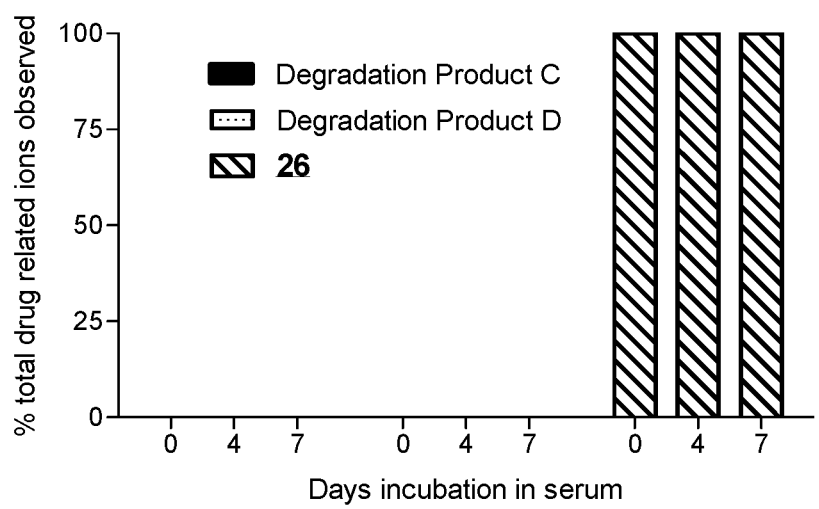

FIG. 4a shows that after both 4 and 7 days at 37° C. in mouse serum, significant degradation of compound 78 (comparator) has occurred, with peaks corresponding to degradation products A and B detectable by reverse phase Orbitrap-MS analysis. The amount of degradation product B in particular, is increased from day 4 to day 7. In contrast, in FIG. 4b, no degradation products equivalent to A and B (designated C and D below) were observed for compound 26 following 7 days incubation. These data are consistent with compound 26 having improved stability versus compound 78 (comparator). The structures of compound 78 and fragments A and B are shown below.

135
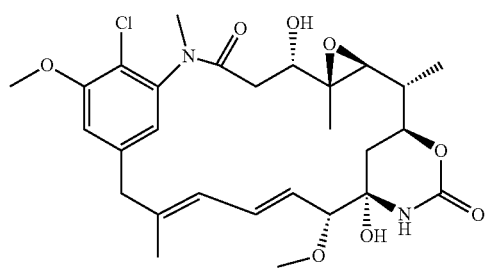
A
136
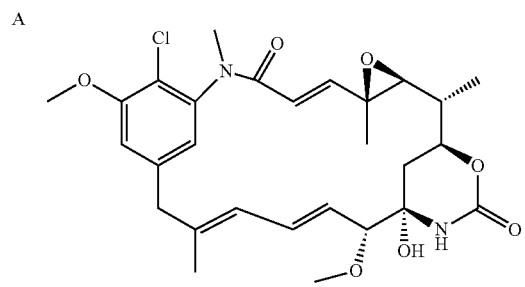
B
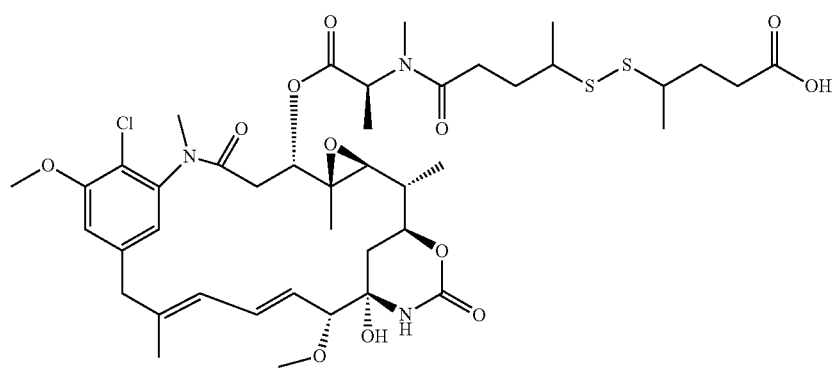
The structures of compound 26 and fragments C and D are shown below.
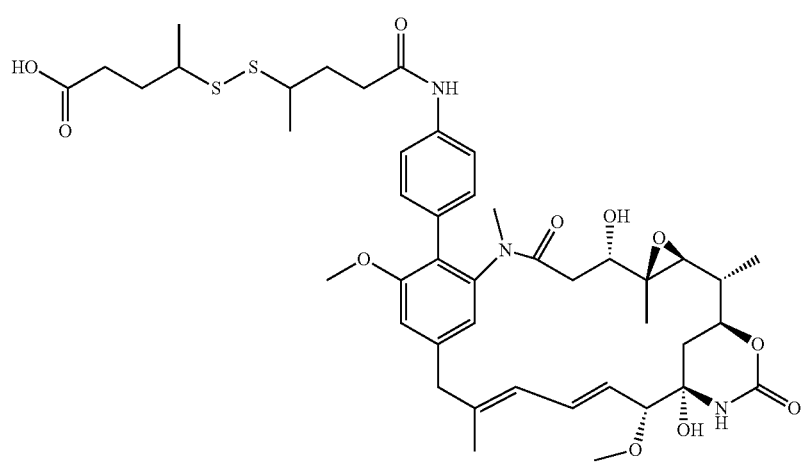
C

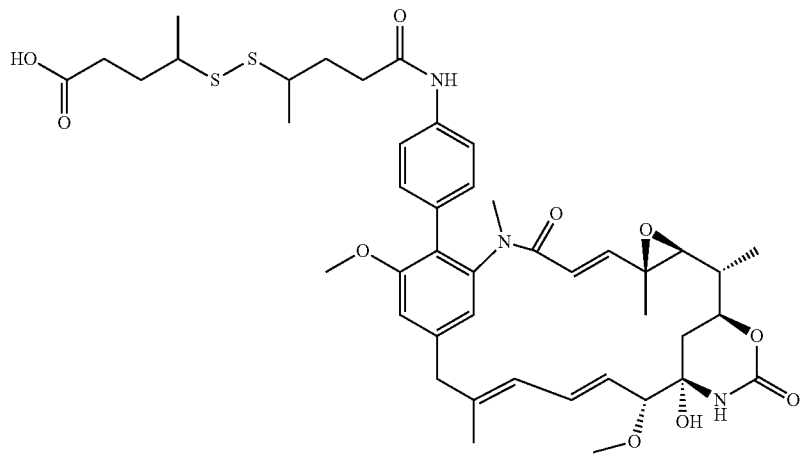

26

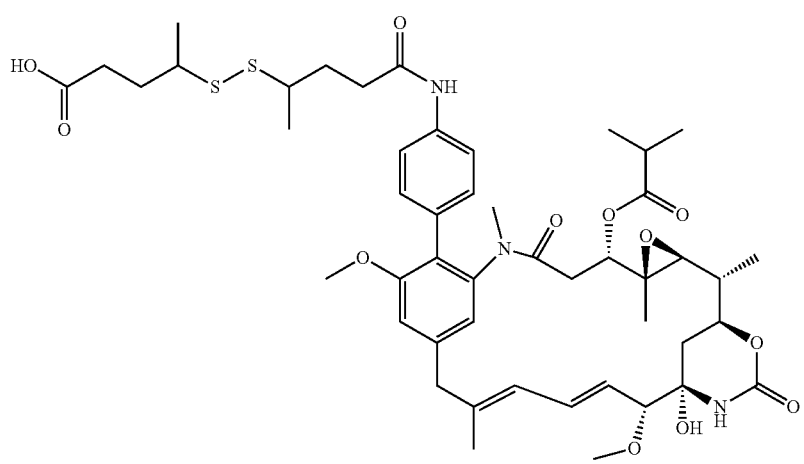

D

The invention claimed is:

1. A compound of the general formula I or a salt thereof:

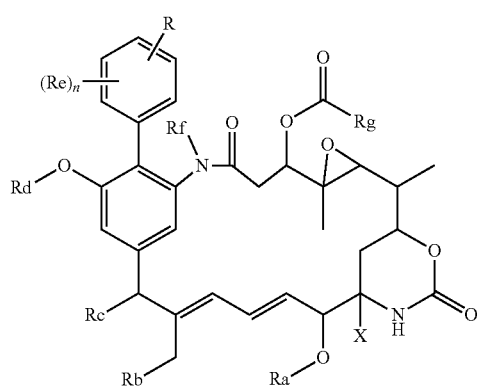

(I)

in which R represents a group —Y—OH, —Y—O—R$^x$, —Y—SH, —Y—S—R$^x$, —Y—S(O)$_2$NH—R$^x$, —Y—NHS(O)$_2$—R$^x$, —Y—C(O)H, —Y—CO$_2$H, —Y—C(O)—R$^x$, —Y—C(O)NH—R$^x$, —Y—NHC(O)—R$^x$, —Y—NHR$^y$, —Y—NR$^x$R$^y$, —Y—NR$^y$—NHR$^z$, —Y—CR$^y$=NOH, —Y—C(NH$_2$)=NOH, —Y—C(O)NH$_2$, —Y—C(O)NH—NH$_2$, or —Y—S(O)$_2$NH$_2$, in which either Y is not present or Y represents a C$_{1-6}$alkylene, C$_{2-6}$alkenylene, C$_{2-6}$alkynylene or C$_{1-6}$alkyleneoxy group which may be interrupted by an oxygen atom and/or which may optionally be substituted by —OH or —OC$_{1-4}$alkyl, or Y represents a phenylene or C$_{5-10}$heteroarylene group;

R$^x$ represents a C$_{1-6}$alkyl, C$_{2-6}$alkenyl, C$_{2-6}$alkynyl, phenyl, C$_{5-10}$heteroaryl or benzyl group which is substituted by —OH, —SH, —NHR$^y$, or —CO$_2$H;

each of R$^y$ and R$^z$ independently represents a hydrogen atom, a C$_{1-4}$alkyl group, phenyl, C$_{5-10}$heteroaryl or a benzyl group;

X represents OH, OC$_{1-4}$alkyl, SH, S$_{1-4}$alkyl, or CN;

Ra represents a hydrogen atom or a C$_{1-4}$alkyl group;

Rb represents hydrogen, OH, C$_{1-4}$alkoxy or C$_{1-4}$alkylC(O)O—;

Rc represents hydrogen, OH, C$_{1-4}$alkoxy or C$_{1-4}$alkylC(O)O—;

Rd represents a C$_{1-4}$alkyl group;

each Re independently represents a halogen atom, an optionally substituted C$_{1-6}$alkyl, C$_{2-6}$alkenyl, C$_{2-6}$alkynyl or C$_{1-6}$alkoxy group each of which may be optionally interrupted by an oxygen atom, an optionally substituted phenyl or C$_{5-10}$heteroaryl group, —OH, —CO$_2$R$^v$, —C(O)NR'R$^w$, —NR$^y$C(O)R$^w$, NR'R$^w$, —S(O)—R$^v$, S(O)$_2$—R$^v$, —S(O)$_2$NR'R$^w$, a —CN group, or a —NO$_2$ group; R$^v$ and R$^w$ are each independently selected from the group consisting of hydrogen, phenyl, benzyl, and an optionally substituted C$_{1-6}$alkyl, $C_{2-6}$alkenyl or $C_{2-6}$alkynyl group each of which may be optionally interrupted by an oxygen atom; and n is 0, 1, 2, 3 or 4;

Rf represents a hydrogen atom or a $C_{1-4}$alkyl group; and

Rg represents a hydrogen atom or an optionally substituted alkyl, cycloalkyl, alkenyl, alkynyl, aryl, or heteroaryl group.

2. The compound as claimed in claim 1, wherein R is an —OH, —NH$_2$, —SH, —CONH$_2$, —SO$_2$NH$_2$, —CO$_2$H, CH$_2$OH, or —NHC(O)—$C_{1-6}$alkylene-SH group.

3. The compound as claimed in claim 1, wherein R is a —NHC(O)—$C_{1-6}$alkyl which alkyl is substituted by —SH.

4. The compound as claimed in claim 1, wherein any Re group present is selected from the group consisting of a halogen atom, a methoxy group, a —CN group or a —NO$_2$ group; and/or wherein Rg represents $C_{1-4}$alkyl which is unsubstituted or substituted by N(R$^i$)(R$^{ii}$); R$^i$ represents a $C_{1-4}$alkyl group; and R$^{ii}$ represents a —C(O)—$C_{1-6}$alkyl group.

5. The compound as claimed in claim 1, wherein R represents a group —Y—OH, —Y—O—R$^x$, —Y—SH, —Y—CO$_2$H, —Y—NHR$^y$, —Y—NR$^y$—NHR$^z$, or —Y—CR$^y$=NOH, in which either Y is not present or Y represents a $C_{1-6}$alkylene or $C_{1-6}$alkyleneoxy group either of which may be interrupted by an oxygen atom, R$^x$ represents a $C_{1-4}$alkyl group substituted by —OH, —SH, —NHR$^y$, or —CO$_2$H, and each of R$^y$ and R$^z$ independently represents a hydrogen atom or a $C_{1-4}$alkyl group; X represents OH, OC$_{1-4}$alkyl, SH, S$_{1-4}$alkyl, or CN; Ra represents a hydrogen atom or a $C_{1-4}$alkyl group; Rb represents hydrogen, OH, $C_{1-4}$alkoxy or $C_{1-4}$alkylC(O)O—; Rc represents hydrogen, OH, $C_{1-4}$alkoxy or $C_{1-4}$alkylC(O)O—; Rd represents a $C_{1-4}$alkyl group; each Re independently represents a halogen atom, a CF$_3$ group, or a $C_{1-4}$alkyl or $C_{1-4}$alkoxy group, and n is 0, 1, 2, 3 or 4; Rf represents a hydrogen atom or a $C_{1-4}$alkyl group; and Rg represents a hydrogen atom or an optionally substituted alkyl, cycloalkyl, alkenyl, alkynyl, aryl, or heteroaryl group.

6. The compound as claimed in claim 1, in which:
i) Y is not present, or in which Y represents a $C_{1-4}$alkylene or $C_{1-4}$alkyleneoxy group, which may be interrupted by an oxygen atom; and/or
ii) R is an —OH, —NH$_2$, —CONH$_2$ or —CO$_2$H group, or a $C_{1-4}$alkylene group substituted by an —OH, —NH$_2$, —CONH$_2$ or —CO$_2$H group; and/or R is in the 3- or 4-position of the phenyl ring; and/or
iii) any Re group present is a halogen atom or a methyl or methoxy group; and/or
iv) n is 0, 1 or 2; and/or
v) X represents OH; and/or
vi) Ra represents $C_{1-4}$alkyl; Rb represents hydrogen; Rc represents hydrogen or methoxy; Rd represents $C_{1-4}$alkyl; Re represents chlorine or hydrogen; Rf represents $C_{1-4}$alkyl; and Rg represents $C_{1-4}$alkyl.

7. The compound as claimed in claim 1, which is a compound of the general formula Ia or a salt thereof:

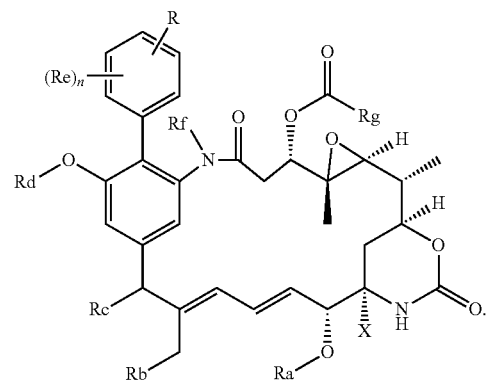

(Ia)

8. The compound as claimed in claim 1, which is a compound of the general formula Ib or a salt thereof:

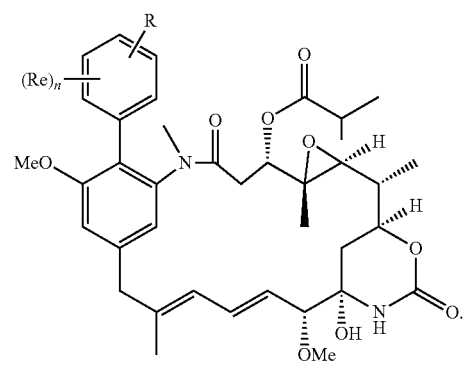

(Ib)

9. A conjugate comprising the compound as claimed in claim 1 linked to a binding protein via a linker, said linker being connected to said compound via the group R of the general formula I;
wherein:
i) the linker includes the group —S—$C_{1-6}$alkylene-; and/or
ii) the binding protein is a full length antibody or an antibody fragment comprising an antigen-binding region of the full length antibody.

10. The conjugate as claimed in claim 9, wherein the binding protein is IgG1 or IgG4 or a fragment of IgG1 or IgG4.

11. The conjugate as claimed in claim 9, which includes a portion:

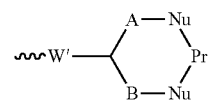

in which W' represents an electron withdrawing group or a group obtained by reduction of an electron withdrawing group, each of A and B independently represents a $C_{1-5}$alkylene or alkenylene chain, and Pr represents said binding protein bonded to A and B via nucleophiles Nu; or includes a portion:

~W'—(CH=CH)$_p$—(CH$_2$)$_2$-Nu-Pr in which W' represents an electron withdrawing group or a group obtained by reduction of an electron withdrawing group, p is 0 or an integer from 1 to 4, and Pr represents said binding protein bonded to the rest of the molecule via a nucleophile Nu.

12. The conjugate as claimed in claim 9, which includes a portion:

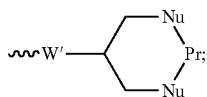

or which includes a portion:

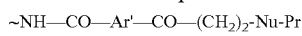

in which Ar' represents an optionally substituted aryl group.

13. The conjugate as claimed in claim 9, in which each Nu represents a sulfur atom present in a cysteine residue in the binding protein Pr; or in which each Nu represents an imidazole group present in a polyhistidine tag attached to the binding protein.

14. The conjugate as claimed in claim 9, in which:
   i) the linker includes a pendant polyethylene glycol chain which has a terminal end group of formula —$CH_2CH_2OR''$ in which R'' represents a hydrogen atom, an alkyl group, or an optionally substituted aryl group; or
   ii) at least two ~($CH_2$—$CH_2$—O—)~ units within a ring; and/or
   iii) the linker includes a peptidyl group comprising at least two naturally-occurring alpha amino acids.

15. The conjugate as claimed in claim 9, wherein the linker includes the sequence Val-Cit-PAB or Val-Ala.

16. A conjugating reagent comprising the compound as claimed in claim 1, attached via a linker to at least one functional group capable of reacting with a binding protein, said linker being connected to said compound via the group R of the general formula I; and wherein:
   i) the conjugating reagent includes a portion

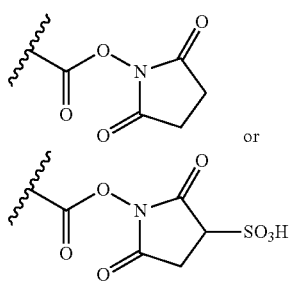

or a salt thereof; or
   ii) the conjugating reagent includes a portion:

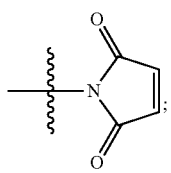 [SMILES: *N1C(=O)C=CC1=O]

or
   iii) the functional group of the conjugating reagent has the formula:

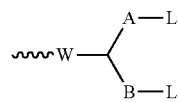

in which W represents an electron-withdrawing group; each of A and B independently represents a $C_{1-5}$alkylene or alkenylene chain; and either each L independently represents a leaving group, or both Ls together represent a leaving group; or

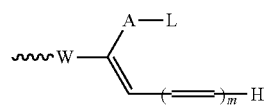

in which W and A have the meanings given above, L represents a leaving group, and m is 0 to 4; or ~W—(CH=CH)$_p$—(CH$_2$)$_2$-L or ~W—(CH=CH)$_p$—CH=CH$_2$ in which W represents an electron withdrawing group, p represents 0 or an integer of from 1 to 4, and L represents a leaving group.

17. The conjugating reagent as claimed in claim 16, in which said functional group has the formula:

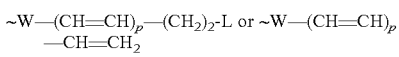

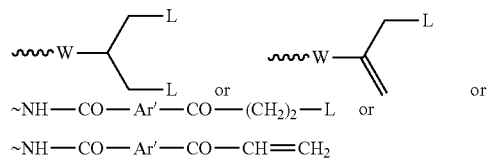

in which Ar' represents an optionally substituted aryl group.

18. The conjugating reagent as claimed in claim 16, in which:
   i) the or each leaving group includes a portion —(CH$_2$CH$_2$O)$_q$— in which q is a number of six or more; or
   ii) the linker
      a) includes a pendant polyethylene glycol chain which has a terminal end group of formula —CH$_2$CH$_2$OR'' in which R'' represents a hydrogen atom, an alkyl group, or an optionally substituted aryl group; or
      b) has at least two ~(CH$_2$—CH$_2$—O—)~ units within a ring; and/or
      c) includes a peptidyl group comprising at least two naturally-occurring alpha amino acids.

19. A pharmaceutical composition comprising the compound as claimed in claim 1, or a conjugate comprising the compound of claim 1, together with a pharmaceutically acceptable carrier, optionally together with an additional therapeutic agent.

20. A process for the preparation of a compound of the general formula I or a salt thereof as claimed in claim 1, which comprises reacting a compound of the general formula:

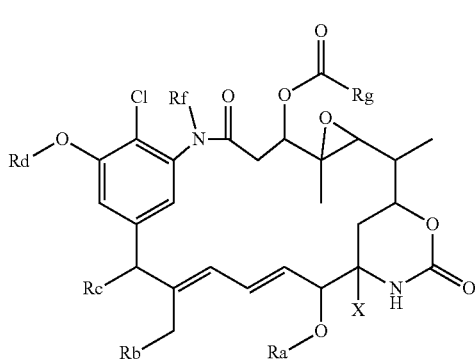
(II)

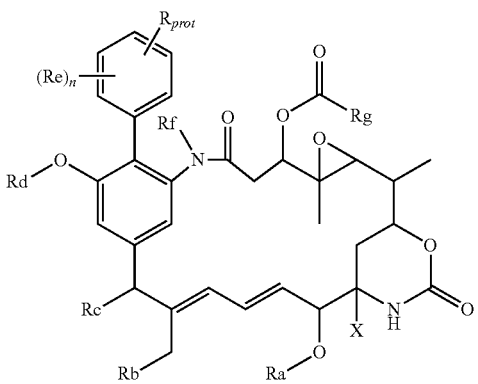

with an aryl-organometallic reagent in which the aryl moiety is a phenyl group substituted by $(Re)_n$ and by R or a protected version of R, the reaction being carried out in the presence of a transition metal catalyst;

wherein, optionally, the aryl-organometallic reagent is an aryl-boronic acid or aryl-boronate ester, and in which the reaction is carried out in the presence of a palladium catalyst in the presence of water and in the absence or substantial absence of oxygen.

21. The process as claimed in claim 20, wherein R represents a group —Y—OH, —Y—O—$R^x$, —Y—SH, —Y—S—$R^x$, —Y—$CO_2H$, —Y—CO—$R^x$, —Y—$NHR^y$, —Y—$NR^y$—$NHR^z$, or —Y—$CR^y$=NOH, in which either Y is not present or Y represents a $C_{1-6}$alkylene or $C_{1-6}$alkyleneoxy group either of which may be interrupted by an oxygen atom, $R^x$ represents a $C_{1-4}$alkyl group substituted by —OH, —SH, —$NHR^y$, or —$CO_2H$, and each of $R^y$ and $R^z$ independently represents a hydrogen atom or a $C_{1-4}$alkyl group; X represents OH, $OC_{1-4}$alkyl, SH, $S_{1-4}$alkyl, or CN; Ra represents a hydrogen atom or a $C_{1-4}$alkyl group; Rb represents hydrogen, OH, $C_{1-4}$alkoxy or $C_{1-4}$alkylC(O)O—; Rc represents hydrogen, OH, $C_{1-4}$alkoxy or $C_{1-4}$alkylC(O)O—; Rd represents a $C_{1-4}$alkyl group; each Re independently represents a halogen atom, a $CF_3$ group, or a $C_{1-4}$alkyl or $C_{1-4}$alkoxy group, and n is 0, 1, 2, 3 or 4; Rf represents a hydrogen atom or a $C_{1-4}$alkyl group; and Rg represents a hydrogen atom or an optionally substituted alkyl, cycloalkyl, alkenyl, alkynyl, aryl, or heteroaryl group.

22. The process as claimed in claim 20, in which the aryl-organometallic reagent is a boronic acid of the general formula:

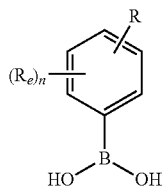
(III)

or a protected version thereof and the reaction is carried out in the presence of a palladium catalyst.

23. An intermediate useful for preparing a compound of the general formula I or a salt thereof as claimed in claim 1, which has the general formula and $R_{prot}$ is the group R of the general formula I carrying a protecting group; or a salt thereof;

wherein optionally, R includes an —OH or —SH group and the protecting group is a silyl group, an acyl group, or an arylmethyl group; R includes a —$CO_2H$ group and the protecting group is methyl, ethyl, t-butyl, benzyl, p-methoxybenzyl, 9-fluorenylmethyl, trimethylsilyl, t-butyldimethylsilyl, or diphenylmethyl; or R includes an —NHR', —NHR" or —NHR'" group and the protecting group is t-butoxycarbonyl, trityl, benzyloxycarbonyl, 9-fluorenylmethoxycarbonyl, formyl, trimethylsilyl, or t-butyldimethylsilyl.

24. A compound as claimed in claim 1, wherein R is selected from —Y—OH, —Y—SH, —Y—$S(O)_2NH$—$R^x$, —Y—$NHS(O)_2$—$R^x$, —Y—$CO_2H$, —Y—C(O)NH—$R^x$, —Y—NHC(O)—$R^x$, —Y—$NHR^y$ or —Y—$S(O)_2NH_2$, in which either Y is not present or Y represents a $C_{1-6}$alkylene, and wherein $R^x$ represents a $C_{1-6}$alkyl which is substituted by —OH, —SH, —$NH_2$ or —$CO_2H$; and $R^y$ represents a hydrogen atom or a $C_{1-4}$alkyl group.

25. A compound as claimed in claim 1, wherein R represents a group selected from —Y—SH, —Y—$S(O)_2$NH—$R^x$, —Y—$NHS(O)_2$—$R^x$, —Y—C(O)NH—$R^x$, —Y—NHC(O)—$R^x$, or —Y—$S(O)_2NH_2$, wherein $R^x$ represents a $C_{1-6}$alkyl which is substituted by —OH, —SH, —$NH_2$ or —$CO_2H$.

26. A compound as claimed in claim 1, wherein R represents —Y—NHC(O)—$R^x$, wherein Y is absent and $R^x$ represents a $C_{1-6}$alkyl which is substituted by —OH, —SH, —$NH_2$ or —$CO_2H$.

27. A compound as claimed in claim 1, wherein Rd is methyl.

28. A compound as claimed in claim 1, wherein X represents OH.

29. A compound as claimed in claim 1, wherein Ra represents a $C_{1-4}$alkyl group and Rb represents hydrogen.

30. A compound as claimed in claim 1, wherein Rc represents hydrogen or methoxy.

31. A compound as claimed in claim 1, wherein each Re independently represents a halogen atom, a $CF_3$ group, a $C_{1-4}$alkyl group, a $C_{1-4}$alkoxy group, a —CN group, or a $NO_2$ group, and wherein n is 0, 1 or 2.

32. A compound as claimed in claim 1, wherein Rg represents $C_{1-4}$alkyl which is unsubstituted or substituted by $N(R^i)(R^{ii})$, and wherein $R^i$ represents a $C_{1-4}$alkyl group, and $R^{ii}$ represents a —C(O)—$C_{1-6}$alkyl group.

* * * * *

UNITED STATES PATENT AND TRADEMARK OFFICE
CERTIFICATE OF CORRECTION

PATENT NO. : 10,654,873 B2  
APPLICATION NO. : 16/332797  
DATED : May 19, 2020  
INVENTOR(S) : Jain et al.

Page 1 of 1

It is certified that error appears in the above-identified patent and that said Letters Patent is hereby corrected as shown below:

In the Claims

Claim 1, Column 138, Line 63, "-NR$^y$C(O)R$^w$, NR$^v$R$^w$" should read -- -NR$^v$C(O)R$^w$, NR$^v$R$^w$, -SR$^v$, --

Claim 5, Column 139, Line 26, "-Y-CO$_2$H, -Y-NHR$^y$," should read -- -Y-S-R$^x$, -Y-CO$_2$H, -Y-CO-R$^x$, -Y-NHR$^y$, --

Signed and Sealed this  
Third Day of November, 2020

Andrei Iancu  
*Director of the United States Patent and Trademark Office*